(12) United States Patent
Picataggio et al.

(10) Patent No.: US 7,459,546 B2
(45) Date of Patent: Dec. 2, 2008

(54) GLYCERALDEHYDE-3-PHOSPHATE DEHYDROGENASE AND PHOSPHOGLYCERATE MUTASE REGULATORY SEQUENCES FOR GENE EXPRESSION IN OLEAGINOUS YEAST

(75) Inventors: Stephen K. Picataggio, Landenberg, PA (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 359 days.

(21) Appl. No.: 11/183,664

(22) Filed: Jul. 18, 2005

(65) Prior Publication Data
US 2006/0019297 A1    Jan. 26, 2006

Related U.S. Application Data

(63) Continuation-in-part of application No. 10/869,630, filed on Jun. 16, 2004, now Pat. No. 7,259,255.

(60) Provisional application No. 60/482,263, filed on Jun. 25, 2003.

(51) Int. Cl.
- *C07H 21/04* (2006.01)
- *C12N 12/81* (2006.01)
- *C12N 1/00* (2006.01)

(52) U.S. Cl. .................. 536/24.1; 435/320.1; 435/69.1; 435/255.1

(58) Field of Classification Search .................. None
See application file for complete search history.

(56) References Cited

U.S. PATENT DOCUMENTS

| | | | |
|---|---|---|---|
| 4,937,189 A | 6/1990 | Davidow et al. | |
| 6,265,185 B1 | 7/2001 | Muller et al. | |
| 6,451,565 B1 | 9/2002 | Rabenhorst et al. | |
| 7,267,976 B2 * | 9/2007 | Yadav et al. | 435/254.2 |
| 2005/0136519 A1 | 6/2005 | Picataggio et al. | |

FOREIGN PATENT DOCUMENTS

| | | |
|---|---|---|
| DE | 279627 | 5/1990 |
| EP | 0005277 B1 | 1/1982 |
| EP | 220864 | 3/1993 |
| EP | 832258 | 4/2002 |
| WO | WO 01/83773 A1 | 11/2001 |
| WO | WO 01/88144 A1 | 11/2001 |

OTHER PUBLICATIONS

Ratledge, Microbial Oils and Fats: An Assessment of Their Commercial Potential, C., Prog. Ind. Microbiol. vol. 16: pp. 119-206, 1982.
Bitter, Expression of Heterologous Genes in *Saccharomyces cerevisiae* From Vectors Utilizing the Glyceraldehydes-3-Phosphate Dehydrogenase Gene Promoter, G.A. et al., Gene 32(3): pp. 263-274, 1984.
Rodicio et al., Transcriptional Control of Yeast Phosphoglycerate Mutase-Encoding Gene, Gene, vol. 125(2):125-133, 1993.
Blanchin-Roland et al., Two Upstream Activation Sequences Control the Expression of the XPR2 Gene in the Yeast *Yarrowia lipolytica*, Mol. Cell Biol., vol. 14(1); pp. 327-338, 1994.

* cited by examiner

*Primary Examiner*—Maria Marvich

(57) ABSTRACT

The regulatory sequences associated with the *Yarrowia lipolytica* glyceraldehyde-3-phosphate dehydrogenase (gpd) and phosphoglycerate mutase (gpm) genes have been found to be particularly effective for the expression of heterologous genes in oleaginous yeast. The promoter regions of the invention, intron and enhancer have been shown to drive high-level expression of genes involved in the production of ω-3 and ω-6 fatty acids.

2 Claims, 19 Drawing Sheets

FIG. 1A

A: *Saccharomyces cerevisiae* (SEQ ID NO:1; GenBank Accession No. CAA24607)
B: *Schizosaccharomyces pombe* (SEQ ID NO:2; GenBank Accession No. NP_595236)
C: *Aspergillus oryzae* (SEQ ID NO:3; GenBank Accession No. AAK08065)
D: *Paralichthys olivaceus* (SEQ ID NO:4; GenBank Accession No. BAA88638)
E: *Xenopus laevis* (SEQ ID NO:5; GenBank Accession No. P51469)
F: *Gallus gallus* (SEQ ID NO:6; GenBank Accession No. DECHG3)

```
     1 MPKLVLVRHGQSEWNEKNLFTGWDVKLSARGCCEAARAGELLKEKKYP      A
     1 MPKIIILTRHGQSDWNEKNLFTGWDVKLSELGHTEAKRAGTLLKESGIKP      B

51 DVLYTSKLSRAIQTANIATEKADRIWIPVNRSWRLNERHYCELQGKDME      A
    51 QILYTSELSRAIQTANIALDEADRLWIPTKRSWRLNERHYGALQGKEAA      B

101 TIKKFGEEKFLTYRRSFDVPPPPIDASSFSQKGDERKYVLPNVLPS       A
   101 TLAEYCEEQFQIWRRSFDVPPPPIADDRWSCYNDERYQFIEKDILRTE     B

151 SIALVIDRLLPVWQDVIAKDLISGKTVMIAAHGNSLRGLVKHLEGISPAI   A
   151 SIKLVIDRLLPYYNSDIVFDIRAGKTVLIAAHGNSLFALVKHLDGISDE    B

201 IAKLNIPTGIPLVELDENLKPSKPSYYLDPEAAAAGAAAVANQGK       A
   201 LAALNIPTGIPLVIRP.                                    B
```

A: *Saccharomyces cerevisiae* (SEQ ID NO:13; GenBank Accession No. NP_012770)
B: *Yarrowia lipolytica* (SEQ ID NO:16)

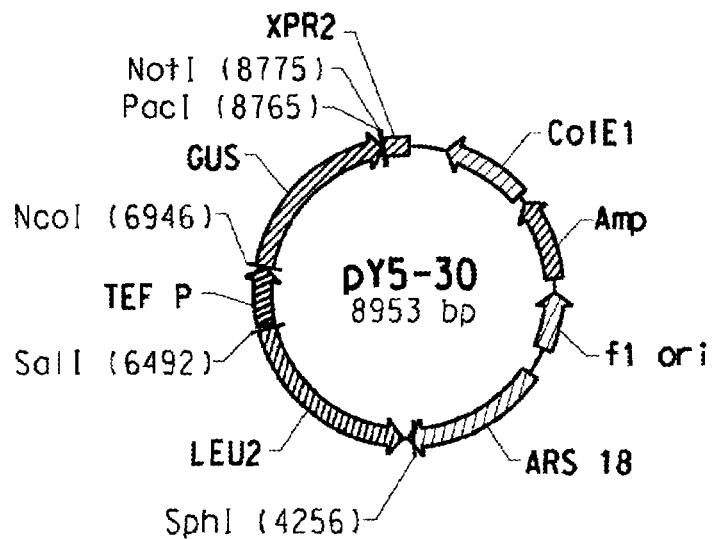
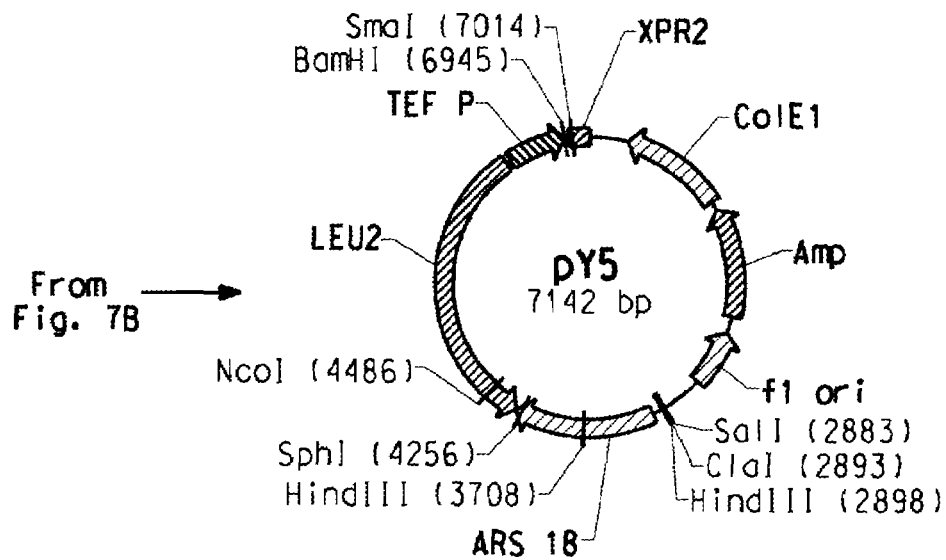
FIG. 7C

FBAIN   GPDIN   GPM   GPM::   TEF
                      GPDIN

SEQUENCE LISTING

<160> NUMBER OF SEQ ID NOS: 97

<210> SEQ ID NO 1
<211> LENGTH: 332
<212> TYPE: PRT
<213> ORGANISM: Sacchromyces cerevisiae (Genbank Accession No. CAA24607)

<400> SEQUENCE: 1

```
Met Val Arg Val Ala Ile Asn Gly Phe Gly Arg Ile Gly Arg Leu Val
1               5                   10                  15

Met Arg Ile Ala Leu Ser Arg Pro Asn Val Glu Val Val Ala Leu Asn
            20                  25                  30

Asp Pro Phe Ile Thr Asn Asp Tyr Ala Ala Tyr Met Phe Lys Tyr Asp
        35                  40                  45

Ser Thr His Gly Arg Tyr Ala Gly Glu Val Ser His Asp Asp Lys His
    50                  55                  60

Ile Ile Val Asp Gly Lys Lys Ile Ala Thr Tyr Gln Glu Arg Asp Pro
65                  70                  75                  80

Ala Asn Leu Pro Trp Gly Ser Ser Asn Val Asp Ile Ala Ile Asp Ser
                85                  90                  95

Thr Gly Val Phe Lys Glu Leu Asp Thr Ala Gln Lys His Ile Asp Ala
            100                 105                 110

Gly Ala Lys Lys Val Val Ile Thr Ala Pro Ser Ser Thr Ala Pro Met
        115                 120                 125

Phe Val Met Gly Val Asn Glu Val Lys Tyr Thr Ser Asp Leu Lys Ile
    130                 135                 140

Val Ser Asn Ala Ser Cys Thr Thr Asn Cys Leu Ala Pro Leu Ala Lys
```

-continued

```
            145                 150                 155                 160
Val Ile Asn Asp Ala Phe Gly Ile Glu Glu Gly Leu Met Thr Thr Val
                165                 170                 175

His Ser Leu Thr Ala Thr Gln Lys Thr Val Asp Gly Pro Ser His Lys
            180                 185                 190

Asp Trp Arg Gly Gly Arg Thr Ala Ser Gly Asn Ile Ile Pro Ser Ser
        195                 200                 205

Thr Gly Ala Ala Lys Ala Val Gly Lys Val Leu Pro Glu Leu Gln Gly
    210                 215                 220

Lys Leu Thr Gly Met Ala Phe Arg Val Pro Thr Val Asp Val Ser Val
225                 230                 235                 240

Val Asp Leu Thr Val Lys Leu Asp Lys Glu Thr Thr Tyr Asp Glu Ile
                245                 250                 255

Lys Lys Val Val Lys Ala Ala Ala Glu Gly Lys Leu Lys Gly Val Leu
            260                 265                 270

Gly Tyr Thr Glu Asp Ala Val Val Ser Ser Asp Phe Leu Gly Asp Ser
        275                 280                 285

His Ser Ser Ile Phe Asp Ala Ser Ala Gly Ile Gln Leu Ser Pro Lys
    290                 295                 300

Phe Val Lys Leu Val Ser Trp Tyr Asp Asn Glu Tyr Gly Tyr Ser Thr
305                 310                 315                 320

Arg Val Val Asp Leu Val Glu His Ile Ala Lys Ala
                325                 330
```

<210> SEQ ID NO 2
<211> LENGTH: 335
<212> TYPE: PRT
<213> ORGANISM: Schizosaccharomyces pombe (Genbank Accession No. NP_595236)

<400> SEQUENCE: 2

```
Met Ala Ile Pro Lys Val Gly Ile Asn Gly Phe Gly Arg Ile Gly Arg
1               5                   10                  15

Ile Val Leu Arg Asn Ala Ile Leu Thr Gly Lys Ile Gln Val Val Ala
            20                  25                  30

Val Asn Asp Pro Phe Ile Asp Leu Asp Tyr Met Ala Tyr Met Phe Lys
        35                  40                  45

Tyr Asp Ser Thr His Gly Arg Phe Glu Gly Ser Val Glu Thr Lys Gly
    50                  55                  60

Gly Lys Leu Val Ile Asp Gly His Ser Ile Asp Val His Asn Glu Arg
65                  70                  75                  80

Asp Pro Ala Asn Ile Lys Trp Ser Ala Ser Gly Ala Glu Tyr Val Ile
                85                  90                  95

Glu Ser Thr Gly Val Phe Thr Thr Lys Glu Thr Ala Ser Ala His Leu
            100                 105                 110

Lys Gly Gly Ala Lys Arg Val Ile Ile Ser Ala Pro Ser Lys Asp Ala
        115                 120                 125

Pro Met Phe Val Val Gly Val Asn Leu Glu Lys Phe Asn Pro Ser Glu
    130                 135                 140

Lys Val Ile Ser Asn Ala Ser Cys Thr Thr Asn Cys Leu Ala Pro Leu
145                 150                 155                 160

Ala Lys Val Ile Asn Asp Thr Phe Gly Ile Glu Glu Gly Leu Met Thr
                165                 170                 175

Thr Val His Ala Thr Thr Ala Thr Gln Lys Thr Val Asp Gly Pro Ser
            180                 185                 190
```

-continued

```
Lys Lys Asp Trp Arg Gly Gly Arg Gly Ala Ser Ala Asn Ile Ile Pro
            195                 200                 205

Ser Ser Thr Gly Ala Ala Lys Ala Val Gly Lys Val Ile Pro Ala Leu
    210                 215                 220

Asn Gly Lys Leu Thr Gly Met Ala Phe Arg Val Pro Thr Pro Asp Val
225                 230                 235                 240

Ser Val Val Asp Leu Thr Val Lys Leu Ala Lys Pro Thr Asn Tyr Glu
                245                 250                 255

Asp Ile Lys Ala Ala Ile Lys Ala Ala Ser Glu Gly Pro Met Lys Gly
            260                 265                 270

Val Leu Gly Tyr Thr Glu Asp Ser Val Val Ser Thr Asp Phe Cys Gly
        275                 280                 285

Asp Asn His Ser Ser Ile Phe Asp Ala Ser Ala Gly Ile Gln Leu Ser
    290                 295                 300

Pro Gln Phe Val Lys Leu Val Ser Trp Tyr Asp Asn Glu Trp Gly Tyr
305                 310                 315                 320

Ser His Arg Val Val Asp Leu Val Ala Tyr Thr Ala Ser Lys Asp
                325                 330                 335

<210> SEQ ID NO 3
<211> LENGTH: 338
<212> TYPE: PRT
<213> ORGANISM: Aspergillus oryzae (Genbank Accession No. AAK08065)

<400> SEQUENCE: 3

Met Ala Thr Pro Lys Val Gly Ile Asn Gly Phe Gly Arg Ile Gly Arg
1               5                   10                  15

Ile Val Phe Arg Asn Ala Ile Ala Ser Gly Asp Val Asp Val Val Ala
            20                  25                  30

Val Asn Asp Pro Phe Ile Glu Thr His Tyr Ala Ala Tyr Met Leu Lys
        35                  40                  45

Tyr Asp Ser Thr His Gly Arg Phe Gln Gly Thr Ile Glu Thr Tyr Asp
    50                  55                  60

Glu Gly Leu Ile Val Asn Gly Lys Lys Ile Arg Phe Phe Ala Glu Arg
65                  70                  75                  80

Asp Pro Ala Ala Ile Pro Trp Gly Ser Ala Gly Ala Ala Tyr Ile Val
                85                  90                  95

Glu Ser Thr Gly Val Phe Thr Thr Glu Lys Ala Ser Ala His Leu
            100                 105                 110

Lys Gly Gly Ala Lys Lys Val Ile Ile Ser Ala Pro Ser Ala Asp Ala
        115                 120                 125

Pro Met Phe Val Met Gly Val Asn Asn Lys Glu Tyr Lys Thr Asp Ile
    130                 135                 140

Asn Val Leu Ser Asn Ala Ser Cys Thr Thr Asn Cys Leu Ala Pro Leu
145                 150                 155                 160

Ala Lys Val Ile Asn Asp Asn Phe Gly Leu Val Glu Gly Leu Met Thr
                165                 170                 175

Thr Val His Ser Tyr Thr Ala Thr Gln Lys Thr Val Asp Ala Pro Ser
            180                 185                 190

Ala Lys Asp Trp Arg Gly Gly Arg Thr Ala Ala Gln Asn Ile Ile Pro
        195                 200                 205

Ser Ser Thr Gly Ala Ala Lys Ala Val Gly Lys Val Ile Pro Ser Leu
    210                 215                 220

Asn Gly Lys Leu Thr Gly Met Ser Met Arg Val Pro Thr Ala Asn Val
```

```
                225                 230                 235                 240
Ser Val Val Asp Leu Thr Cys Arg Thr Glu Lys Ala Val Thr Tyr Glu
                245                 250                 255

Asp Ile Lys Lys Thr Ile Lys Ala Ala Ser Glu Glu Gly Glu Leu Lys
                260                 265                 270

Gly Ile Leu Gly Tyr Thr Glu Asp Ile Val Ser Thr Asp Leu Ile
                275                 280                 285

Gly Asp Ala His Ser Ser Ile Phe Asp Ala Lys Ala Gly Ile Ala Leu
                290                 295                 300

Asn Glu His Phe Ile Lys Leu Val Ser Trp Tyr Asp Asn Glu Trp Gly
305                 310                 315                 320

Tyr Ser Arg Arg Val Val Asp Leu Ile Ala Tyr Ile Ser Lys Val Asp
                325                 330                 335

Gly Gln

<210> SEQ ID NO 4
<211> LENGTH: 333
<212> TYPE: PRT
<213> ORGANISM: Paralichthys olivaceus (Genbank Accession No. BAA88638)

<400> SEQUENCE: 4

Met Val Lys Val Gly Ile Asn Gly Phe Gly Arg Ile Gly Arg Leu Val
1               5                   10                  15

Thr Arg Ala Ala Phe Thr Ser Lys Lys Val Glu Ile Val Ala Ile Asn
                20                  25                  30

Asp Pro Phe Ile Asp Leu Glu Tyr Met Val Tyr Met Phe Lys Tyr Asp
                35                  40                  45

Ser Thr His Gly Arg Phe Lys Gly Glu Val Lys Ile Glu Gly Asp Lys
                50                  55                  60

Leu Val Ile Asp Gly His Lys Ile Thr Val Phe His Glu Arg Asp Pro
65              70                  75                  80

Thr Asn Ile Lys Trp Gly Asp Ala Gly Ala His Tyr Val Val Glu Ser
                85                  90                  95

Thr Gly Val Phe Thr Thr Ile Glu Lys Ala Ser Ala His Leu Lys Gly
                100                 105                 110

Gly Ala Lys Lys Val Ile Ile Ser Ala Pro Ser Ala Asp Ala Pro Met
                115                 120                 125

Phe Val Met Gly Val Asn His Glu Lys Tyr Asp Lys Ser Leu Gln Val
                130                 135                 140

Val Ser Asn Ala Ser Cys Thr Thr Asn Cys Leu Ala Pro Leu Ala Lys
145                 150                 155                 160

Val Ile Asn Asp Asn Phe Gly Ile Ile Glu Gly Leu Met Ser Thr Val
                165                 170                 175

His Ala Ile Thr Ala Thr Gln Lys Thr Val Asp Gly Pro Ser Gly Lys
                180                 185                 190

Leu Trp Arg Asp Gly Arg Gly Ala Ser Gln Asn Ile Ile Pro Ala Ser
                195                 200                 205

Thr Gly Ala Ala Lys Ala Val Gly Lys Val Ile Pro Glu Leu Asn Gly
                210                 215                 220

Lys Leu Thr Gly Met Ala Phe Arg Val Pro Thr Pro Asn Val Ser Val
225                 230                 235                 240

Val Asp Leu Thr Val Arg Leu Glu Lys Pro Ala Ser Tyr Glu Asn Ile
                245                 250                 255

Lys Lys Val Val Lys Ala Ala Ala Glu Gly Pro Met Lys Gly Tyr Leu
```

```
                    260                 265                 270
Ala Tyr Thr Glu His Gln Val Val Ser Thr Asp Phe Asn Gly Asp Thr
                275                 280                 285

His Ser Ser Ile Phe Asp Ala Gly Ala Gly Ile Ala Leu Asn Asp His
            290                 295                 300

Phe Val Lys Leu Val Ser Trp Tyr Asp Asn Glu Phe Ala Tyr Ser Asn
305                 310                 315                 320

Arg Val Cys Asp Leu Met Ala His Met Ala Ser Lys Glu
                325                 330
```

<210> SEQ ID NO 5
<211> LENGTH: 333
<212> TYPE: PRT
<213> ORGANISM: Xenopus laevis (Genbank Accession No. P51469)

<400> SEQUENCE: 5

```
Met Val Lys Val Gly Ile Asn Gly Phe Gly Cys Ile Gly Arg Leu Val
1               5                   10                  15

Thr Arg Ala Ala Phe Asp Ser Gly Lys Val Gln Val Val Ala Ile Asn
            20                  25                  30

Asp Pro Phe Ile Asp Leu Asp Tyr Met Val Tyr Met Phe Lys Tyr Asp
        35                  40                  45

Ser Thr His Gly Arg Phe Lys Gly Thr Val Lys Ala Glu Asn Gly Lys
    50                  55                  60

Leu Ile Ile Asn Asp Gln Val Ile Thr Val Phe Gln Glu Arg Asp Pro
65                  70                  75                  80

Ser Ser Ile Lys Trp Gly Asp Ala Gly Ala Val Tyr Val Val Glu Ser
                85                  90                  95

Thr Gly Val Phe Thr Thr Thr Glu Lys Ala Ser Leu His Leu Lys Gly
            100                 105                 110

Gly Ala Lys Arg Val Val Ile Ser Ala Pro Ser Ala Asp Ala Pro Met
        115                 120                 125

Phe Val Val Gly Val Asn His Glu Lys Tyr Glu Asn Ser Leu Lys Val
    130                 135                 140

Val Ser Asn Ala Ser Cys Thr Thr Asn Cys Leu Ala Pro Leu Ala Lys
145                 150                 155                 160

Val Ile Asn Asp Asn Phe Gly Ile Val Glu Gly Leu Met Thr Thr Val
                165                 170                 175

His Ala Phe Thr Ala Thr Gln Lys Thr Val Asp Gly Pro Ser Gly Lys
            180                 185                 190

Leu Trp Arg Asp Gly Arg Gly Ala Gly Gln Asn Ile Ile Pro Ala Ser
        195                 200                 205

Thr Gly Ala Ala Lys Ala Val Gly Lys Val Ile Pro Glu Leu Asn Gly
    210                 215                 220

Lys Ile Thr Gly Met Ala Phe Arg Val Pro Thr Pro Asn Val Ser Val
225                 230                 235                 240

Val Asp Leu Thr Cys Arg Leu Gln Lys Pro Ala Lys Tyr Asp Asp Ile
                245                 250                 255

Lys Ala Ala Ile Lys Thr Ala Ser Glu Gly Pro Met Lys Gly Ile Leu
            260                 265                 270

Gly Tyr Thr Gln Asp Gln Val Val Ser Thr Asp Phe Asn Gly Asp Thr
        275                 280                 285

His Ser Ser Ile Phe Asp Ala Asp Ala Gly Ile Ala Leu Asn Glu Asn
    290                 295                 300
```

Phe Val Lys Leu Val Ser Trp Tyr Asp Asn Glu Cys Gly Tyr Ser Asn
305                 310                 315                 320

Arg Val Val Asp Leu Val Cys His Met Ala Ser Lys Glu
                325                 330

<210> SEQ ID NO 6
<211> LENGTH: 333
<212> TYPE: PRT
<213> ORGANISM: Gallus gallus (Genbank Accession No. DECHG3)

<400> SEQUENCE: 6

Met Val Lys Val Gly Val Asn Gly Phe Gly Arg Ile Gly Arg Leu Val
1               5                   10                  15

Thr Arg Ala Ala Val Leu Ser Gly Lys Val Gln Val Val Ala Ile Asn
                20                  25                  30

Asp Pro Phe Ile Asp Leu Asn Tyr Met Val Tyr Met Phe Lys Tyr Asp
            35                  40                  45

Ser Thr His Gly His Phe Lys Gly Thr Val Lys Ala Glu Asn Gly Lys
        50                  55                  60

Leu Val Ile Asn Gly His Ala Ile Thr Ile Phe Gln Glu Arg Asp Pro
65                  70                  75                  80

Ser Asn Ile Lys Trp Ala Asp Ala Gly Ala Glu Tyr Val Val Glu Ser
                85                  90                  95

Thr Gly Val Phe Thr Thr Met Glu Lys Ala Gly Ala His Leu Lys Gly
            100                 105                 110

Gly Ala Lys Arg Val Ile Ile Ser Ala Pro Ser Ala Asp Ala Pro Met
        115                 120                 125

Phe Val Met Gly Val Asn His Glu Lys Tyr Asp Lys Ser Leu Lys Ile
    130                 135                 140

Val Ser Asn Ala Ser Cys Thr Thr Asn Cys Leu Ala Pro Leu Ala Lys
145                 150                 155                 160

Val Ile His Asp Asn Phe Gly Ile Val Glu Gly Leu Met Thr Thr Val
                165                 170                 175

His Ala Ile Thr Ala Thr Gln Lys Thr Val Asp Gly Pro Ser Gly Lys
            180                 185                 190

Leu Trp Arg Asp Gly Arg Gly Ala Ala Gln Asn Ile Ile Pro Ala Ser
        195                 200                 205

Thr Gly Ala Ala Lys Ala Val Gly Lys Val Ile Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Cys Arg Leu Glu Lys Pro Ala Lys Tyr Asp Asp Ile
                245                 250                 255

Lys Arg Val Val Lys Ala Ala Ala Asp Gly Pro Leu Lys Gly Ile Leu
            260                 265                 270

Gly Tyr Thr Glu Asp Gln Val Val Ser Cys Asp Phe Asn Gly Asp Ser
        275                 280                 285

His Ser Ser Thr Phe Asp Ala Gly Ala Gly Ile Ala Leu Asn Asp His
    290                 295                 300

Phe Val Lys Leu Val Ser Trp Tyr Asp Asn Glu Phe Gly Tyr Ser Asn
305                 310                 315                 320

Arg Val Val Asp Leu Met Val His Met Ala Ser Lys Glu
                325                 330

<210> SEQ ID NO 7

<210> SEQ ID NO 7
<211> LENGTH: 7
<212> TYPE: PRT
<213> ORGANISM: Artificial Sequence
<220> FEATURE:
<223> OTHER INFORMATION: Conserved protein motif in GPD

<400> SEQUENCE: 7

Lys Tyr Asp Ser Thr His Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Conserved protein motif in GPD

<400> SEQUENCE: 8

Thr Gly Ala Ala Lys Ala Val
1               5

<210> SEQ ID NO 9
<211> LENGTH: 20
<212> TYPE: DNA
<213> ORGANISM: Artificial Sequence
<220> FEATURE:
<223> OTHER INFORMATION: Degenerate primer YL193

<400> SEQUENCE: 9
aagtacgayt cbacycaygg                                              20

<210> SEQ ID NO 10
<211> LENGTH: 20
<212> TYPE: DNA
<213> ORGANISM: Artificial Sequence
<220> FEATURE:
<223> OTHER INFORMATION: Degenerate primer YL194

<400> SEQUENCE: 10
acrgccttrg crgcdccrgt                                              20

<210> SEQ ID NO 11
<211> LENGTH: 507
<212> TYPE: DNA
<213> ORGANISM: Yarrowia lipolytica

<400> SEQUENCE: 11
aagtacgact ccacccacgg ccgattcaag ggcaaggtcg aggccaagga cggcggtctg      60
atcatcgacg gcaagcacat ccaggtcttc ggtgagcgag acccctccaa catcccctgg     120
ggtaaggccg gtgccgacta cgttgtcgag tccaccggtg tcttcaccgg caaggaggct     180
gcctccgccc acctcaaggg tggtgccaag aaggtcatca tctccgcccc ctccggtgac     240
gcccccatgt tcgttgtcgg tgtcaacctc gacgcctaca gcccgacat gaccgtcatc     300
tccaacgctt cttgtaccac caactgtctg gctccccttg ccaaggttgt caacgacaag     360
tacggaatca ttgagggtct catgaccacc gtccactcca tcaccgccac ccagaagacc     420
gttgacggtc cttcccacaa ggactggcga ggtggccgaa ccgcctctgg taacatcatc     480
ccctcttcca ccggagccgc caaggct                                        507

<210> SEQ ID NO 12
<211> LENGTH: 169
<212> TYPE: PRT
<213> ORGANISM: Yarrowia lipolytica

<400> SEQUENCE: 12

```
Lys Tyr Asp Ser Thr His Gly Arg Phe Lys Gly Lys Val Glu Ala Lys
1               5                   10                  15

Asp Gly Gly Leu Ile Ile Asp Gly Lys His Ile Gln Val Phe Gly Glu
            20                  25                  30

Arg Asp Pro Ser Asn Ile Pro Trp Gly Lys Ala Gly Ala Asp Tyr Val
        35                  40                  45

Val Glu Ser Thr Gly Val Phe Thr Gly Lys Glu Ala Ala Ser Ala His
    50                  55                  60

Leu Lys Gly Gly Ala Lys Lys Val Ile Ile Ser Ala Pro Ser Gly Asp
65                  70                  75                  80

Ala Pro Met Phe Val Gly Val Asn Leu Asp Ala Tyr Lys Pro Asp
                85                  90                  95

Met Thr Val Ile Ser Asn Ala Ser Cys Thr Thr Asn Cys Leu Ala Pro
            100                 105                 110

Leu Ala Lys Val Val Asn Asp Lys Tyr Gly Ile Ile Glu Gly Leu Met
            115                 120                 125

Thr Thr Val His Ser Ile Thr Ala Thr Gln Lys Thr Val Asp Gly Pro
        130                 135                 140

Ser His Lys Asp Trp Arg Gly Gly Arg Thr Ala Ser Gly Asn Ile Ile
145                 150                 155                 160

Pro Ser Ser Thr Gly Ala Ala Lys Ala
                165
```

<210> SEQ ID NO 13
<211> LENGTH: 245
<212> TYPE: PRT
<213> ORGANISM: Saccharomyces cerevisiae (GenBank Accesssion No. NP_012770)

<400> SEQUENCE: 13

```
Met Pro Lys Leu Val Leu Val Arg His Gly Gln Ser Glu Trp Asn Glu
1               5                   10                  15

Lys Asn Leu Phe Thr Gly Trp Val Asp Val Lys Leu Ser Ala Lys Gly
            20                  25                  30

Gln Gln Glu Ala Ala Arg Ala Gly Glu Leu Leu Lys Glu Lys Lys Val
        35                  40                  45

Tyr Pro Asp Val Leu Tyr Thr Ser Lys Leu Ser Arg Ala Ile Gln Thr
    50                  55                  60

Ala Asn Ile Ala Leu Glu Lys Ala Asp Arg Leu Trp Ile Pro Val Asn
65                  70                  75                  80

Arg Ser Trp Arg Leu Asn Glu Arg His Tyr Gly Asp Leu Gln Gly Lys
                85                  90                  95

Asp Lys Ala Glu Thr Leu Lys Lys Phe Gly Glu Glu Lys Phe Asn Thr
            100                 105                 110

Tyr Arg Arg Ser Phe Asp Val Pro Pro Pro Ile Asp Ala Ser Ser
            115                 120                 125

Pro Phe Ser Gln Lys Gly Asp Glu Arg Tyr Lys Tyr Val Asp Pro Asn
        130                 135                 140

Val Leu Pro Glu Thr Glu Ser Leu Ala Leu Val Ile Asp Arg Leu Leu
145                 150                 155                 160

Pro Tyr Trp Gln Asp Val Ile Ala Lys Asp Leu Leu Ser Gly Lys Thr
                165                 170                 175

Val Met Ile Ala Ala His Gly Asn Ser Leu Arg Gly Leu Val Lys His
```

|     |     | 180 |     |     | 185 |     |     | 190 |     |
| --- | --- | --- | --- | --- | --- | --- | --- | --- | --- |

Leu Glu Gly Ile Ser Asp Ala Asp Ile Ala Lys Leu Asn Ile Pro Thr
            195                      200                   205

Gly Ile Pro Leu Val Phe Glu Leu Asp Glu Asn Leu Lys Pro Ser Lys
 210                        215                     220

Pro Ser Tyr Tyr Leu Asp Pro Glu Ala Ala Ala Gly Ala Ala Ala
225                    230                    235                 240

Val Ala Asn Gln Gly
            245

```
<210> SEQ ID NO 14
<211> LENGTH: 1049
<212> TYPE: DNA
<213> ORGANISM: Yarrowia lipolytica
<220> FEATURE:
<221> NAME/KEY: misc_feature
<222> LOCATION: (1020)..(1020)
<223> OTHER INFORMATION: n is a, c, g, or t

<400> SEQUENCE: 14
caattgagtg cgagcgacac aattgggtgt cacgtgccyt aattgacctc ggatcgtgga      60 gycccccagtt atacagcaac cacgaggtgc atgagtagga dacgtcmcca dacaataggg     120 ttttttttgga ctggagaggg tagggcaaaa gcgctcaacg ggctgtttgg ggagctatgg    180
gggaggaatt ggcgatattt gtgaggttga cggctccgat ttgcgtgttt tgtcgcttct    240
gcatctcccc atacccatat cttccctccc cacctctttc cacgataatt ttacggatca    300
gcaataaggt tccttctcct agtttccacg yccatatata tctatgctgc gtcgtccttt    360
tcgtgacatc accaaaacac atacaaaaat gcctaaactg attctgctgc gacacggcca    420
gtccgactgg aacgagaaga acctgttcac cggatgggtc gacgtcaagt ctccgagctc    480
ggccacaccg aggccaagcg agccggtact ctgctcaagg agtccggtct caagccccag    540
attctctaca cctccgagct ctctcgagcc atccagaccg ccaacattgc tctggatgag    600
gccgaccgac tgtggatccc caccaagcga tcgtggcgac tcaacgagcg acactacggc    660
gctctgcagg gcaaggacaa ggccgccact ctcgccgagt acggccccga gcagttccag    720
ctctggcgac gatcttttga cgtccctcct ccccctatcg ctgacgacga caagtggtct    780
cagtacaacg acgagcgata ccaggacatc cccaaggata ttctgcccaa gaccgagtct    840
ctgaagctcg tgattgaccg actccttcct tactacaact ccgacattgt ccccgacctt    900
aaggccggca agaccgtcct cattgctgcc cacgaaaact ccctccgagc tctcgtcaag    960
cacctcgacg gtatctccga tgacgatatc gccgccctta acatccccac cggtatcccn   1020
ctcgtgctac gaccttgatg acaacctca                                     1049

<210> SEQ ID NO 15
<211> LENGTH: 651
<212> TYPE: DNA
<213> ORGANISM: Yarrowia lipolytica
<220> FEATURE:
<221> NAME/KEY: misc_feature
<222> LOCATION: (633)..(633)
<223> OTHER INFORMATION: n is a, c, g, or t

<400> SEQUENCE: 15
atgcctaaac tgattctgct gcgacacggc cagtccgact ggaacgagaa gaacctgttc      60
accggatggg tcgacgtcaa gctctccgag ctcggccaca ccgaggccaa gcgagccggt    120
actctgctca aggagtccgg tctcaagccc cagattctct acacctccga gctctctcga    180
```

```
gccatccaga ccgccaacat tgctctggat gaggccgacc gactgtggat ccccaccaag    240
cgatcgtggc gactcaacga gcgacactac ggcgctctgc agggcaagga caaggccgcc    300
actctcgccg agtacggccc cgagcagttc cagctctggc gacgatcttt tgacgtccct    360
cctcccccta cgctgacga cgacaagtgg tctcagtaca acgacgagcg ataccaggac    420
atccccaagg atattctgcc caagaccgag tctctgaagc tcgtgattga ccgactcctt    480
ccttactaca actccgacat tgtccccgac cttaaggccg gcaagaccgt cctcattgct    540
gcccacggaa actccctccg agctctcgtc aagcacctcg acggtatctc cgatgacgat    600
atcgccgccc ttaacatccc caccggtatc ccnctcgtgc tacgaccttg a            651
```

<210> SEQ ID NO 16
<211> LENGTH: 216
<212> TYPE: PRT
<213> ORGANISM: Yarrowia lipolytica

<400> SEQUENCE: 16

```
Met Pro Lys Leu Ile Leu Leu Arg His Gly Gln Ser Asp Trp Asn Glu
  1               5                  10                  15

Lys Asn Leu Phe Thr Gly Trp Val Asp Val Lys Leu Ser Glu Leu Gly
             20                  25                  30

His Thr Glu Ala Lys Arg Ala Gly Thr Leu Leu Lys Glu Ser Gly Leu
         35                  40                  45

Lys Pro Gln Ile Leu Tyr Thr Ser Glu Leu Ser Arg Ala Ile Gln Thr
     50                  55                  60

Ala Asn Ile Ala Leu Asp Glu Ala Asp Arg Leu Trp Ile Pro Thr Lys
 65                  70                  75                  80

Arg Ser Trp Arg Leu Asn Glu Arg His Tyr Gly Ala Leu Gln Gly Lys
                 85                  90                  95

Asp Lys Ala Ala Thr Leu Ala Glu Tyr Gly Pro Glu Gln Phe Gln Leu
            100                 105                 110

Trp Arg Arg Ser Phe Asp Val Pro Pro Pro Ile Ala Asp Asp Asp
        115                 120                 125

Lys Trp Ser Gln Tyr Asn Asp Glu Arg Tyr Gln Asp Ile Pro Lys Asp
    130                 135                 140

Ile Leu Pro Lys Thr Glu Ser Leu Lys Leu Val Ile Asp Arg Leu Leu
145                 150                 155                 160

Pro Tyr Tyr Asn Ser Asp Ile Val Pro Asp Leu Lys Ala Gly Lys Thr
                165                 170                 175

Val Leu Ile Ala Ala His Gly Asn Ser Leu Arg Ala Leu Val Lys His
            180                 185                 190

Leu Asp Gly Ile Ser Asp Asp Asp Ile Ala Ala Leu Asn Ile Pro Thr
        195                 200                 205

Gly Ile Pro Leu Val Leu Arg Pro
    210                 215
```

<210> SEQ ID NO 17
<211> LENGTH: 26
<212> TYPE: DNA
<213> ORGANISM: Artificial Sequence
<220> FEATURE:
<223> OTHER INFORMATION: Primer YL206

<400> SEQUENCE: 17

```
ccttgccggt gaagacaccg gtggac                                          26
```

```
<210> SEQ ID NO 18
<211> LENGTH: 25
<212> TYPE: DNA
<213> ORGANISM: Artificial Sequence
<220> FEATURE:
<223> OTHER INFORMATION: Primer YL196

<400> SEQUENCE: 18
gacgtcgacc catccggtga acagg                                               25

<210> SEQ ID NO 19
<211> LENGTH: 28
<212> TYPE: DNA
<213> ORGANISM: Artificial Sequence
<220> FEATURE:
<223> OTHER INFORMATION: Primer YL207

<400> SEQUENCE: 19
gaagacctgg atgtgcttgc cgtcgatg                                            28

<210> SEQ ID NO 20
<211> LENGTH: 23
<212> TYPE: DNA
<213> ORGANISM: Artificial Sequence
<220> FEATURE:
<223> OTHER INFORMATION: Primer YL197

<400> SEQUENCE: 20
gagcagagta ccggctcgct tgg                                                 23

<210> SEQ ID NO 21
<211> LENGTH: 24
<212> TYPE: DNA
<213> ORGANISM: Artificial Sequence
<220> FEATURE:
<223> OTHER INFORMATION: Primer YL208

<400> SEQUENCE: 21
gaccttgccc ttgaatcggc cgtg                                                24

<210> SEQ ID NO 22
<211> LENGTH: 25
<212> TYPE: DNA
<213> ORGANISM: Artificial Sequence
<220> FEATURE:
<223> OTHER INFORMATION: Primer YL198

<400> SEQUENCE: 22
gaatctgggg cttgagaccg gactc                                               25

<210> SEQ ID NO 23
<211> LENGTH: 1848
<212> TYPE: DNA
<213> ORGANISM: Yarrowia lipolytica

<400> SEQUENCE: 23
gtgattgcct ctgaatactt tcaacaagtt acacccttcg cggcgacgat ctacagcccg         60
atcacatgaa ctttggccga gggatgatgt aatcgagtat cgtggtagtt caatacgtac        120
atgtacgatg ggtgcctcaa ttgtgcgata ctactacaag tgcagcacgc tcgtgcccgt        180
accctacttt gtcggacgtc cctgctccct cgttcaacat ctcaagctca acaatcagtg        240
ttggacactg caacgctagc agccggtacg tggctttagc cccatgctcc atgctccatg        300
ctccatgctc tgggcctatg agctagccgt ttggcgcaca tagcatagtg acatgtcgat        360
```

```
caagtcaaag tcgaggtgtg aaaacgggc tgcgggtcgc caggggcctc acaagcgcct      420
ccaccgcaga cgcccacctc gttagcgtcc attgcgatcg tctcggtaca tttggttaca      480
ttttgcgaca ggttgaaatg aatcggccga cgctcggtag tcggaaagag ccgggaccgg      540
ccggcgagca taaaccggac gcagtaggat gtcctgcacg ggtcttttg tggggtgtgg       600 agaaaggggt gcttggagat ggaagccggt agaaccgggc tgcttgtgct ggagatggaa      660
agccggtaga accgggctgc ttgggggat ttggggccgc tgggctccaa agagggtag       720 gcatttcgtt ggggttacgt aattgcgca tttgggtcct cgcgcatgt cccattggtc       780 agaattagtc cggataggag acttatcagc caatcacagc gccggatcca cctgtaggtt      840
gggttgggtg ggagcacccc tccacagagt agagtcaaac agcagcagca acatgatagt      900
tgggggtgtg cgtgttaaag gaaaaaaag aagcttgggt tatattcccg ctctatttag       960
aggttgcggg atagacgccg acggagggca atggcgccat ggaaccttgc ggatatcgat     1020
acgccgcggc ggactgcgtc cgaaccagct ccagcagcgt ttttccgggg ccattgagcc     1080
gactgcgacc ccgccaacgt gtcttggccc acgcactcat gtcatgttgg tgttgggagg     1140
ccacttttta agtagcacaa ggcacctagc tcgcagcaag gtgtccgaac caaagaagcg     1200
gctgcagtgg tgcaaacggg gcggaaacg cggaaaaag ccacggggc acgaattgag       1260 gcacgccctc gaatttgaga cgagtcacgg ccccattcgc ccgcgcaatg gctcgccaac     1320
gcccggtctt ttgcaccaca tcaggttacc ccaagccaaa cctttgtgtt aaaaagctta     1380
acatattata ccgaacgtag gtttgggcgg gcttgctccg tctgtccaag gcaacattta     1440
tataagggtc tgcatcgccg gctcaattga atcttttttc ttcttctctt ctctatattc     1500
attcttgaat taaacacaca tcaacatggc catcaaagtc ggtattaacg gattcggcg      1560 aatcggacga attgtgagta ccatagaagg tgatggaaac atgacccaac agaaacagat     1620
gacaagtgtc atcgacccac cagagcccaa ttgagctcat actaacagtc gacaacctgt     1680
cgaaccaatt gatgactccc cgacaatgta ctaacacagg tcctgcgaaa cgctctcaag     1740
aaccctgagg tcgaggtcgt cgctgtgaac gaccccttca tcgacaccga gtacgctgct     1800
tacatgttca agtacgactc cacccacggc cgattcaagg gcaaggtc                  1848
```

<210> SEQ ID NO 24
<211> LENGTH: 2316
<212> TYPE: DNA
<213> ORGANISM: Yarrowia lipolytica

<400> SEQUENCE: 24

```
gtgattgcct ctgaatactt tcaacaagtt acacccttcg cggcgacgat ctacagcccg       60
atcacatgaa cttttggccga gggatgatgt aatcgagtat cgtggtagtt caatacgtac     120
atgtacgatg ggtgcctcaa ttgtgcgata ctactacaag tgcagcacgc tcgtgcccgt     180
accctacttt gtcggacgtc cctgctccct cgttcaacat ctcaagctca acaatcagtg     240
ttggacactg caacgctagc agccggtacg tggctttagc cccatgctcc atgctccatg     300
ctccatgctc tgggcctatg agctagccgt ttggcgcaca tagcatagtg acatgtcgat     360
caagtcaaag tcgaggtgtg aaaacgggc tgcgggtcgc caggggcctc acaagcgcct      420
ccaccgcaga cgcccacctc gttagcgtcc attgcgatcg tctcggtaca tttggttaca      480
ttttgcgaca ggttgaaatg aatcggccga cgctcggtag tcggaaagag ccgggaccgg      540
ccggcgagca taaaccggac gcagtaggat gtcctgcacg ggtcttttg tggggtgtgg       600
```

```
agaaagggt gcttggagat ggaagccggt agaaccgggc tgcttgtgct tggagatgga    660
agccggtaga accgggctgc ttgggggat ttggggccgc tgggctccaa agaggggtag    720
gcatttcgtt ggggttacgt aattgcggca tttgggtcct gcgcgcatgt cccattggtc    780
agaattagtc cggataggag acttatcagc caatcacagc gccggatcca cctgtaggtt    840
gggttgggtg ggagcacccc tccacagagt agagtcaaac agcagcagca acatgatagt    900 tggggggtgtg cgtgttaaag gaaaaaaaag aagcttgggt tatattcccg ctctatttag    960
aggttgcggg atagacgccg acggagggca atggcgccat ggaaccttgc ggatatcgat   1020
acgccgcggg ggactgcgtc cgaaccagct ccagcagcgt tttttccggg ccattgagcc   1080
gactgcgacc ccgccaacgt gtcttggccc acgcactcat gtcatgttgg tgttgggagg   1140 ccactttta agtagcacaa ggcacctagc tcgcagcaag gtgtccgaac caaagaagcg   1200
gctgcagtgg tgcaaacggg gcggaaacgg cgggaaaaag ccacgggggc acgaattgag   1260
gcacgccctc gaatttgaga cgagtcacgg ccccattcgc ccgcgcaatg gctcgccaac   1320
gcccggtctt ttgcaccaca tcaggttacc ccaagccaaa cctttgtgtt aaaaagctta   1380
acatattata ccgaacgtag gtttgggcgg gcttgctccg tctgtccaag gcaacattta   1440
tataagggtc tgcatcgccg gctcaattga atctttttc ttcttctctt ctctatattc   1500
attcttgaat taaacacaca tcaacatggc catcaaagtc ggtattaacg gattcgggcg   1560
aatcggacga attgtgagta ccatagaagg tgatggaaac atgacccaac agaaacagat   1620
gacaagtgtc atcgacccac cagagcccaa ttgagctcat actaacagtc gacaacctgt   1680
cgaaccaatt gatgactccc cgacaatgta ctaacacagg tcctgcgaaa cgctctcaag   1740
aaccctgagg tcgaggtcgt cgctgtgaac gacccctca tcgacaccga gtacgctgct   1800
tacatgttca agtacgactc cacccacggc cgattcaagg gcaaggtcga ggccaaggac   1860
ggcggtctga tcatcgacgg caagcacatc caggtcttcg gtgagcgaga ccctccaac   1920 atcccctggg gtaaggccgg tgccgactac gttgtcgagt ccaccggtgt cttcaccggc   1980
aaggaggctg cctccgccca ctcaagggt ggtgccaaga aggtcatcat ctccgccccc   2040
tccggtgacg cccccatgtt cgttgtcggt gtcaacctcg acgcctacaa gcccgacatg   2100
accgtcatct ccaacgcttc ttgtaccacc aactgtctgg ctcccccttgc caaggttgtc   2160 aacgacaagt acggaatcat tgagggtctc atgaccaccg tccactccat caccgccacc   2220
cagaagaccg ttgacggtcc tttcccacaag gactggcgag gtggccgaac cgcctctggt   2280
aacatcatcc cctcttccac cggagccgcc aaggct                             2316
```

<210> SEQ ID NO 25
<211> LENGTH: 645
<212> TYPE: DNA
<213> ORGANISM: Yarrowia lipolytica

<400> SEQUENCE: 25

```
atggccatca aagtcggtat taacggattc gggcgaatcg gacgaattgt cctgcgaaac     60
gctctcaaga accctgaggt cgaggtcgtc gctgtgaacg acccccttcat cgacaccgag    120 tacgctgctt acatgttcaa gtacgactcc acccacggcc gattcaaggg caaggtcgag    180
gccaaggacg gcggtctgat catcgacggc aagcacatcc aggtcttcgg tgagcgagac    240
ccctccaaca tcccctgggg taaggccggt gccgactacg ttgtcgagtc caccggtgtc    300
ttcaccggca aggaggctgc ctccgcccac tcaagggtg gtgccaagaa ggtcatcatc    360 tccgcccct ccggtgacgc ccccatgttc gttgtcggtg tcaacctcga cgcctacaag    420
```

```
cccgacatga ccgtcatctc caacgcttct tgtaccacca actgtctggc tccccttgcc    480
aaggttgtca acgacaagta cggaatcatt gagggtctca tgaccaccgt ccactccatc    540
accgccaccc agaagaccgt tgacggtcct tcccacaagg actggcgagg tggccgaacc    600
gcctctggta acatcatccc ctcttccacc ggagccgcca aggct                   645
```

<210> SEQ ID NO 26
<211> LENGTH: 215
<212> TYPE: PRT
<213> ORGANISM: Yarrowia lipolytica

<400> SEQUENCE: 26

```
Met Ala Ile Lys Val Gly Ile Asn Gly Phe Gly Arg Ile Gly Arg Ile
1               5                   10                  15

Val Leu Arg Asn Ala Leu Lys Asn Pro Glu Val Glu Val Val Ala Val
            20                  25                  30

Asn Asp Pro Phe Ile Asp Thr Glu Tyr Ala Ala Tyr Met Phe Lys Tyr
        35                  40                  45

Asp Ser Thr His Gly Arg Phe Lys Gly Lys Val Glu Ala Lys Asp Gly
    50                  55                  60

Gly Leu Ile Ile Asp Gly Lys His Ile Gln Val Phe Gly Glu Arg Asp
65                  70                  75                  80

Pro Ser Asn Ile Pro Trp Gly Lys Ala Gly Ala Asp Tyr Val Val Glu
                85                  90                  95

Ser Thr Gly Val Phe Thr Gly Lys Glu Ala Ala Ser Ala His Leu Lys
            100                 105                 110

Gly Gly Ala Lys Lys Val Ile Ile Ser Ala Pro Ser Gly Asp Ala Pro
        115                 120                 125

Met Phe Val Val Gly Val Asn Leu Asp Ala Tyr Lys Pro Asp Met Thr
    130                 135                 140

Val Ile Ser Asn Ala Ser Cys Thr Thr Asn Cys Leu Ala Pro Leu Ala
145                 150                 155                 160

Lys Val Val Asn Asp Lys Tyr Gly Ile Ile Glu Gly Leu Met Thr Thr
                165                 170                 175

Val His Ser Ile Thr Ala Thr Gln Lys Thr Val Asp Gly Pro Ser His
            180                 185                 190

Lys Asp Trp Arg Gly Gly Arg Thr Ala Ser Gly Asn Ile Ile Pro Ser
        195                 200                 205

Ser Thr Gly Ala Ala Lys Ala
    210                 215
```

<210> SEQ ID NO 27
<211> LENGTH: 953
<212> TYPE: DNA
<213> ORGANISM: Yarrowia lipolytica

<400> SEQUENCE: 27

```
gcctctgaat actttcaaca agttacaccc ttcattaatt ctcacgtgac acagattatt     60
aacgtctcgt accaaccaca gattacgacc cattcgcagt cacagttcac tagggtttgg    120
gttgcatccg ttgagagcgg tttgttttta accttctcca tgtgctcact caggttttgg    180
gttcagatca aatcaaggcg tgaaccactt tgtttgagga caaatgtgac acaaccaacc    240
agtgtcaggg gcaagtccgt gacaaagggg aagatacaat gcaattactg acagttacag    300
actgcctcga tgccctaacc ttgccccaaa ataagacaac tgtcctcgtt taagcgcaac    360
```

```
cctattcagc gtcacgtcat aatagcgttt ggatagcact agtctatgag gagcgtttta    420
tgttgcggtg agggcgattg gtgctcatat gggttcaatt gaggtggcgg aacgagctta    480
gtcttcaatt gaggtgcgag cgacacaatt gggtgtcacg tggcctaatt gacctcgggt    540
cgtggagtcc ccagttatac agcaaccacg aggtgcatgg gtaggagacg tcaccagaca    600
atagggtttt ttttggactg gagagggttg ggcaaaagcg ctcaacgggc tgtttgggga    660
gctgtggggg aggaattggc gatatttgtg aggttaacgg ctccgatttg cgtgttttgt    720
cgctcctgca tctccccata cccatatctt ccctccccac ctctttccac gataatttta    780
cggatcagca ataaggttcc ttctcctagt ttccacgtcc atatatatct atgctgcgtc    840
gtccttttcg tgacatcacc aaaacacata caaaaatgcc taaactgatt ctgctgcgac    900
acggccagtc cgactggaac gagaagaacc tgttcaccgg atgggtcgac gtc           953
```

<210> SEQ ID NO 28
<211> LENGTH: 1537
<212> TYPE: DNA
<213> ORGANISM: Yarrowia lipolytica
<220> FEATURE:
<221> NAME/KEY: misc_feature
<222> LOCATION: (1507)..(1507)
<223> OTHER INFORMATION: n is a, c, g, or t

<400> SEQUENCE: 28

```
gcctctgaat actttcaaca agttacaccc ttcattaatt ctcacgtgac acagattatt    60
aacgtctcgt accaaccaca gattacgacc cattcgcagt cacagttcac tagggtttgg    120
gttgcatccg ttgagagcgg tttgtttta accttctcca tgtgctcact caggttttgg    180
gttcagatca aatcaaggcg tgaaccactt tgtttgagga caaatgtgac acaaccaacc    240
agtgtcaggg gcaagtccgt gacaaagggg aagatacaat gcaattactg acagttacag    300
actgcctcga tgccctaacc ttgccccaaa ataagacaac tgtcctcgtt taagcgcaac    360
cctattcagc gtcacgtcat aatagcgttt ggatagcact agtctatgag gagcgtttta    420
tgttgcggtg agggcgattg gtgctcatat gggttcaatt gaggtggcgg aacgagctta    480
gtcttcaatt gaggtgcgag cgacacaatt gggtgtcacg tggcctaatt gacctcgggt    540
cgtggagtcc ccagttatac agcaaccacg aggtgcatgg gtaggagacg tcaccagaca    600
atagggtttt ttttggactg gagagggttg ggcaaaagcg ctcaacgggc tgtttgggga    660
gctgtggggg aggaattggc gatatttgtg aggttaacgg ctccgatttg cgtgttttgt    720
cgctcctgca tctccccata cccatatctt ccctccccac ctctttccac gataatttta    780
cggatcagca ataaggttcc ttctcctagt ttccacgtcc atatatatct atgctgcgtc    840
gtccttttcg tgacatcacc aaaacacata caaaaatgcc taaactgatt ctgctgcgac    900
acggccagtc cgactggaac gagaagacct gttcaccgga tgggtcgacg tcaagctctc    960
cgagctcggc cacaccgagg ccaagcgagc cggtactctg ctcaaggagt ccggtctcaa   1020
gccccagatt ctctacacct ccgagctctc tcgagccatc cagaccgcca acattgctct   1080
ggatgaggcc gaccgactgt ggatccccac caagcgatcg tggcgactca acgagcgaca   1140
ctacggcgct ctgcagggca aggacaaggc cgccactctc gccgagtacg ccccgagca    1200 gttccagctc tggcgacgat cttttgacgt ccctcctccc cctatcgctg acgacgacaa   1260
gtggtctcag tacaacgacg agcgatacca ggacatcccc aaggatattc tgcccaagac   1320
cgagtctctg aagctcgtga ttgaccgact ccttccttac tacaactccg acattgtccc   1380
cgaccttaag gccggcaaga ccgtcctcat tgctgcccac ggaaactccc tccgagctct   1440
```

```
cgtcaagcac ctcgacggta tctccgatga cgatatcgcc gcccttaaca tccccaccgg    1500
tatcccnctc gtgctacgac cttgatgaca acctcaa                             1537

<210> SEQ ID NO 29
<211> LENGTH: 7
<212> TYPE: PRT
<213> ORGANISM: Yarrowia lipolytica

<400> SEQUENCE: 29

Ala Ile Pro Ala Val Asn Val
1               5

<210> SEQ ID NO 30
<211> LENGTH: 7
<212> TYPE: PRT
<213> ORGANISM: Yarrowia lipolytica

<400> SEQUENCE: 30

Glu Met Glu Ile Gly Ile Thr
1               5

<210> SEQ ID NO 31
<211> LENGTH: 20
<212> TYPE: DNA
<213> ORGANISM: Artificial Sequence
<220> FEATURE:
<223> OTHER INFORMATION: Primer YL214

<400> SEQUENCE: 31
gcyatyccyg cygtyaacgt                                                  20

<210> SEQ ID NO 32
<211> LENGTH: 20
<212> TYPE: DNA
<213> ORGANISM: Artificial Sequence
<220> FEATURE:
<223> OTHER INFORMATION: Primer YL216

<400> SEQUENCE: 32
gtratdccra tctccatctc                                                  20

<210> SEQ ID NO 33
<211> LENGTH: 436
<212> TYPE: DNA
<213> ORGANISM: Yarrowia lipolytica

<400> SEQUENCE: 33
attcctgctg tcaacgtgac ctcttcgtcc accgttgtcg ccgttcttga gtctgcccga     60
gccaacaagt cccccgtcat catccagatg tcccagggtg gcgctgccta ctttgctggc    120
aagggtgtcg acaacaagga tcagaccgcc tccatccagg agccattgc cgctgcccag     180 ttcatccgaa ccattgctcc cgtttacggc attcccgtca tcgtccacac cgaccactgt    240
gcccgaaagc tgctcccctg gctcgacggt atgctgacg ccgatgagga gtacttcaag     300
actcacggtg agcccctctt ctcttcacac atggtggatc tctccgagga ggagcacccc    360
gagaacatcg ccaccaccgc cgagtacttc aagcgagccg ccaagatgaa ccagtggctc    420
gagatggaga tcggca                                                    436

<210> SEQ ID NO 34
<211> LENGTH: 145
<212> TYPE: PRT
```

<213> ORGANISM: Yarrowia lipolytica

<400> SEQUENCE: 34

| Ile | Pro | Ala | Val | Asn | Val | Thr | Ser | Ser | Thr | Val | Ala | Val | Leu |
|---|---|---|---|---|---|---|---|---|---|---|---|---|---|
| 1 | | | | 5 | | | | | 10 | | | | 15 |

Glu Ser Ala Arg Ala Asn Lys Ser Pro Val Ile Ile Gln Met Ser Gln
        20                  25                  30

Gly Gly Ala Ala Tyr Phe Ala Gly Lys Gly Val Asp Asn Lys Asp Gln
            35                  40                  45

Thr Ala Ser Ile Gln Gly Ala Ile Ala Ala Gln Phe Ile Arg Thr
    50                  55                  60

Ile Ala Pro Val Tyr Gly Ile Pro Val Ile Val His Thr Asp His Cys
65                  70                  75                  80

Ala Arg Lys Leu Leu Pro Trp Leu Asp Gly Met Leu Asp Ala Asp Glu
                85                  90                  95

Glu Tyr Phe Lys Thr His Gly Glu Pro Leu Phe Ser Ser His Met Val
            100                 105                 110

Asp Leu Ser Glu Glu Glu His Pro Glu Asn Ile Ala Thr Thr Ala Glu
        115                 120                 125

Tyr Phe Lys Arg Ala Ala Lys Met Asn Gln Trp Leu Glu Met Glu Ile
    130                 135                 140

Gly
145

<210> SEQ ID NO 35
<211> LENGTH: 24
<212> TYPE: DNA
<213> ORGANISM: Artificial Sequence
<220> FEATURE:
<223> OTHER INFORMATION: Primer YL217

<400> SEQUENCE: 35
cttgttggct cgggcagact caag                                      24

<210> SEQ ID NO 36
<211> LENGTH: 24
<212> TYPE: DNA
<213> ORGANISM: Artificial Sequence
<220> FEATURE:
<223> OTHER INFORMATION: Primer YL218

<400> SEQUENCE: 36
gcagcgccac cctgggacat ctgg                                      24

<210> SEQ ID NO 37
<211> LENGTH: 24
<212> TYPE: DNA
<213> ORGANISM: Artificial Sequence
<220> FEATURE:
<223> OTHER INFORMATION: Primer YL219

<400> SEQUENCE: 37
gatccttgtt gtcgacaccc ttgc                                      24

<210> SEQ ID NO 38
<211> LENGTH: 857
<212> TYPE: DNA
<213> ORGANISM: Yarrowia lipolytica

<400> SEQUENCE: 38
gggcctcaaa actacctcgg aactgctgcg ctgatctgga caccacagag gttccgagca    60

| | |
|---|---|
| ctttaggttg caccaaatgt cccaccaggt gcaggcagaa aacgctggaa cagcgtgtac | 120 |
| agtttgtctt aacaaaaagt gagggcgctg aggtcgagca gggtggtgtg acttgttata | 180 |
| gcctttagag ctgcgaaagc gcgtatggat ttggctcatc aggccagatt gagggtctgt | 240 |
| ggacacatgt catgttagtg tacttcaatc gcccctgga tatagccccg acaataggcc | 300 |
| gtggcctcat ttttttgcct tccgcacatt tccattgctc ggtacccaca ccttgcttct | 360 |
| cctgcacttg ccaaccttaa tactggttta cattgaccaa catcttacaa gcggggggct | 420 |
| tgtctagggt atatataaac agtggctctc ccaatcggtt gccagtctct ttttccttt | 480 |
| ctttccccac agattcgaaa tctaaactac acatcacaca atgcctgtta ctgacgtcct | 540 |
| taagcgaaag tccggtgtca tcgtcggcga cgatgtccga gccgtgagta tccacgacaa | 600 |
| gatcagtgtc gagacgacgc gttttgtgta atgacacaat ccgaaagtcg ctagcaacac | 660 |
| acactctcta cacaaactaa cccagctctt cgagtacgcc cgagagcaca agttcgccct | 720 |
| ccccgccgtc aacgtgacct cttcgtccac cgttgtcgcc gttcttgagt ctgcccgagc | 780 |
| caacaagtcc cccgtcatca tccagatgtc ccagggtggc gctgcctact ttgctggcaa | 840 |
| gggtgtcgac aacaagg | 857 |

<210> SEQ ID NO 39
<211> LENGTH: 520
<212> TYPE: DNA
<213> ORGANISM: Yarrowia lipolytica

<400> SEQUENCE: 39

| | |
|---|---|
| gggcctcaaa actacctcgg aactgctgcg ctgatctgga caccacagag gttccgagca | 60 |
| ctttaggttg caccaaatgt cccaccaggt gcaggcagaa aacgctggaa cagcgtgtac | 120 |
| agtttgtctt aacaaaaagt gagggcgctg aggtcgagca gggtggtgtg acttgttata | 180 |
| gcctttagag ctgcgaaagc gcgtatggat ttggctcatc aggccagatt gagggtctgt | 240 |
| ggacacatgt catgttagtg tacttcaatc gcccctgga tatagccccg acaataggcc | 300 |
| gtggcctcat ttttttgcct tccgcacatt tccattgctc ggtacccaca ccttgcttct | 360 |
| cctgcacttg ccaaccttaa tactggttta cattgaccaa catcttacaa gcggggggct | 420 |
| tgtctagggt atatataaac agtggctctc ccaatcggtt gccagtctct ttttccttt | 480 |
| ctttccccac agattcgaaa tctaaactac acatcacaca | 520 |

<210> SEQ ID NO 40
<211> LENGTH: 1153
<212> TYPE: DNA
<213> ORGANISM: Yarrowia lipolytica

<400> SEQUENCE: 40

| | |
|---|---|
| gggcctcaaa actacctcgg aactgctgcg ctgatctgga caccacagag gttccgagca | 60 |
| ctttaggttg caccaaatgt cccaccaggt gcaggcagaa aacgctggaa cagcgtgtac | 120 |
| agtttgtctt aacaaaaagt gagggcgctg aggtcgagca gggtggtgtg acttgttata | 180 |
| gcctttagag ctgcgaaagc gcgtatggat ttggctcatc aggccagatt gagggtctgt | 240 |
| ggacacatgt catgttagtg tacttcaatc gcccctgga tatagccccg acaataggcc | 300 |
| gtggcctcat ttttttgcct tccgcacatt tccattgctc ggtacccaca ccttgcttct | 360 |
| cctgcacttg ccaaccttaa tactggttta cattgaccaa catcttacaa gcggggggct | 420 |
| tgtctagggt atatataaac agtggctctc ccaatcggtt gccagtctct ttttccttt | 480 |

```
ctttccccac agattcgaaa tctaaactac acatcacaca atgcctgtta ctgacgtcct    540
taagcgaaag tccggtgtca tcgtcggcga cgatgtccga gccgtgagta tccacgacaa    600
gatcagtgtc gagacgacgc gttttgtgta atgacacaat ccgaaagtcg ctagcaacac    660
acactctcta cacaaactaa cccagctctt cgagtacgcc cgagagcaca agttcgccct    720
ccccgccgtc aacgtgacct cttcgtccac cgttgtcgcc gttcttgagt ctgcccgagc    780
caacaagtcc cccgtcatca tccagatgtc ccagggtggc gctgcctact ttgctggcaa    840
gggtgtcgac aacaaggatc agaccgcctc catccaggga gccattgccg ctgcccagtt    900
catccgaacc attgctcccg tttacggcat tcccgtcatc gtccacaccg accactgtgc    960
ccgaaagctg ctcccctggc tcgacggtat gctcgacgcc gatgaggagt acttcaagac   1020
tcacggtgag cccctcttct cttcacacat ggtggatctc tccgaggagg agcaccccga   1080
gaacatcgcc accaccgccg agtacttcaa gcgagccgcc aagatgaacc agtggctcga   1140
gatggagatc ggc                                                     1153

<210> SEQ ID NO 41
<211> LENGTH: 531
<212> TYPE: DNA
<213> ORGANISM: Yarrowia lipolytica

<400> SEQUENCE: 41
atgcctgtta ctgacgtcct taagcgaaag tccggtgtca tcgtcggcga cgatgtccga     60
gccctcttcg agtacgcccg agagcacaag ttcgccctcc ccgccgtcaa cgtgacctct    120
tcgtccaccg ttgtcgccgt tcttgagtct gcccgagcca acaagtcccc cgtcatcatc    180
cagatgtccc agggtggcgc tgcctacttt gctggcaagg gtgtcgacaa caaggatcag    240
accgcctcca tccagggagc cattgccgct gcccagttca tccgaaccat tgctcccgtt    300
tacggcattc ccgtcatcgt ccacaccgac cactgtgccc gaaagctgct cccctggctc    360
gacggtatgc tcgacgccga tgaggagtac ttcaagactc acggtgagcc cctcttctct    420
tcacacatgg tggatctctc cgaggaggag caccccgaga acatcgccac caccgccgag    480
tacttcaagc gagccgccaa gatgaaccag tggctcgaga tggagatcgg c             531

<210> SEQ ID NO 42
<211> LENGTH: 177
<212> TYPE: PRT
<213> ORGANISM: Yarrowia lipolytica

<400> SEQUENCE: 42

Met Pro Val Thr Asp Val Leu Lys Arg Lys Ser Gly Val Ile Val Gly
1               5                   10                  15

Asp Asp Val Arg Ala Leu Phe Glu Tyr Ala Arg Glu His Lys Phe Ala
                20                  25                  30

Leu Pro Ala Val Asn Val Thr Ser Ser Thr Val Val Ala Val Leu
            35                  40                  45

Glu Ser Ala Arg Ala Asn Lys Ser Pro Val Ile Ile Gln Met Ser Gln
        50                  55                  60

Gly Gly Ala Ala Tyr Phe Ala Gly Lys Gly Val Asp Asn Lys Asp Gln
65                  70                  75                  80

Thr Ala Ser Ile Gln Gly Ala Ile Ala Ala Gln Phe Ile Arg Thr
                85                  90                  95

Ile Ala Pro Val Tyr Gly Ile Pro Val Ile Val His Thr Asp His Cys
            100                 105                 110
```

Ala Arg Lys Leu Leu Pro Trp Leu Asp Gly Met Leu Asp Ala Asp Glu
        115                 120                 125

Glu Tyr Phe Lys Thr His Gly Glu Pro Leu Phe Ser Ser His Met Val
    130                 135                 140

Asp Leu Ser Glu Glu His Pro Glu Asn Ile Ala Thr Thr Ala Glu
145                 150                 155                 160

Tyr Phe Lys Arg Ala Ala Lys Met Asn Gln Trp Leu Glu Met Glu Ile
            165                 170                 175

Gly

<210> SEQ ID NO 43
<211> LENGTH: 26
<212> TYPE: DNA
<213> ORGANISM: Artificial Sequence
<220> FEATURE:
<223> OTHER INFORMATION: Primer ODMW315

<400> SEQUENCE: 43
cacctggtgg gacatttggt gcaacc                                        26

<210> SEQ ID NO 44
<211> LENGTH: 26
<212> TYPE: DNA
<213> ORGANISM: Artificial Sequence
<220> FEATURE:
<223> OTHER INFORMATION: Primer ODMW316

<400> SEQUENCE: 44
gacaaactgt acacgctgtt ccagcg                                        26

<210> SEQ ID NO 45
<211> LENGTH: 24
<212> TYPE: DNA
<213> ORGANISM: Artificial Sequence
<220> FEATURE:
<223> OTHER INFORMATION: Primer ODMW317

<400> SEQUENCE: 45
cctgctcgac ctcagcgccc tcac                                          24

<210> SEQ ID NO 46
<211> LENGTH: 1152
<212> TYPE: DNA
<213> ORGANISM: Yarrowia lipolytica

<400> SEQUENCE: 46
agtcgaggac ttatcctagc ctcygaatac tttcaacaag ttacaccctt attccccacc    60
aagccgctag atacgccact aagcaaagtt caagagccat cgcacaatta tctacgagta   120
ccgcagcaat cattcatttc aaggcacaca tggggtttct cttgcagaaa acgcacggt    180
ttcaaagtat aaacgcacat ctaggccgag acaagttgcg gggtatggta ctagtatttc   240
cgggtgcatt ccacgggtga atgggcgttt agaattgagg caattgccac gggttgggcc   300
acatatgttg agtactcatt tctcctctca atgaacgtct ccagaatgac atacattctc   360
ctccaacacc ttgtgggta aacttctgtc agattccacg taacaaggtt ggtgtcggaa    420
caacgaaaaa ggatcggaac agagcttccg gtgtcggtga ttgggcaggg ggctgaggcg   480
tgcctggcgc gtgcgcgtgg tagagagagt gtgctacagc agagagatat tactcgtttg   540
gagctagaga tgccgccgtt gaagaaatta cgaacgagt aactaacaga ccattccagg    600
atcatcgagg accgttgtca gcgcccttac tacagaaatg tatgtacagt aattacaact   660

```
gcgcggctgc ttgacggatg tatggagtct aagtaatgag tgcgtacgta gcaacaacag    720
tgtacgcagt actatagagg aacaattgcc ccggagaaga cggccaggcc gcctagatga    780
caaattcaac aactcacagc tgactttctg ccattgccac tagggggggg ccttttata     840 tggccaagcc aagctctcca cgtcggttgg gctgcaccca acaataaatg ggtagggttg    900
caccaacaaa gggatgggat gggggtaga agatacgagg ataacggggc tcaatggcac    960
aaataagaac gaatactgcc attaagactc gtgatccagc gactgacacc attgcatcat   1020
ctaagggcct caaaactacc tcggaactgc tgcgctgatc tggacaccac agaggttccg   1080
agcactttag gttgcaccaa atgtcccacc aggtgcaggc agaaaacgct ggaacagcgt   1140
gtacagtttg tc                                                       1152

<210> SEQ ID NO 47
<211> LENGTH: 2177
<212> TYPE: DNA
<213> ORGANISM: Yarrowia lipolytica

<400> SEQUENCE: 47
agtcgaggac ttatcctagc ctcygaatac tttcaacaag ttacacccctt attccccacc    60 aagccgctag atacgccact aagcaaagtt caagagccat cgcacaatta tctacgagta   120
ccgcagcaat cattcatttc aaggcacaca tggggtttct cttgcagaaa aacgcacggt   180
ttcaaagtat aaacgcacat ctaggccgag acaagttgcg gggtatggta ctagtatttc   240
cgggtgcatt ccacgggtga atgggcgttt agaattgagg caattgccac gggttgggcc   300
acatatgttg agtactcatt tctcctctca atgaacgtct ccagaatgac atacattctc   360
ctccaacacc ttgtgggta aacttctgtc agattccacg taacaaggtt ggtgtcggaa    420
caacgaaaaa ggatcggaac agagcttccg gtgtcggtga ttgggcaggg ggctgaggcg   480
tgcctggcgc gtgcgcgtgg tagagagagt gtgctacagc agagagatat tactcgtttg   540
gagctagaga tgccgccgtt gaagaaatta cgaacgagt aactaacaga ccattccagg    600
atcatcgagg accgttgtca gcgcccttac tacagaaatg tatgtacagt aattacaact   660
gcgcggctgc ttgacggatg tatggagtct aagtaatgag tgcgtacgta gcaacaacag   720
tgtacgcagt actatagagg aacaattgcc ccggagaaga cggccaggcc gcctagatga   780
caaattcaac aactcacagc tgactttctg ccattgccac tagggggggg ccttttata    840 tggccaagcc aagctctcca cgtcggttgg gctgcaccca acaataaatg ggtagggttg   900
caccaacaaa gggatgggat gggggtaga agatacgagg ataacggggc tcaatggcac    960
aaataagaac gaatactgcc attaagactc gtgatccagc gactgacacc attgcatcat  1020
ctaagggcct caaaactacc tcggaactgc tgcgctgatc tggacaccac agaggttccg  1080
agcactttag gttgcaccaa atgtcccacc aggtgcaggc agaaaacgct ggaacagcgt  1140
gtacagtttg tcttaacaaa aagtgagggc gctgaggtcg agcagggtgg tgtgacttgt  1200
tatagccttt agagctgcga aagcgcgtat ggatttggct catcaggcca gattgagggt  1260
ctgtggacac atgtcatgtt agtgtacttc aatcgccccc tggatatagc cccgacaata  1320
ggccgtggcc tcatttttt gccttccgca catttccatt gctcggtacc cacaccttgc   1380
ttctcctgca cttgccaacc ttaatactgg tttacattga ccaacatctt acaagcgggg  1440
ggcttgtcta gggtatatat aaacagtggc tctcccaatc ggttgccagt ctcttttttc  1500 cttctttcc ccacagattc gaaatctaaa ctacacatca cacaatgcct gttactgacg   1560
```

```
tccttaagcg aaagtccggt gtcatcgtcg gcgacgatgt ccgagccgtg agtatccacg    1620
acaagatcag tgtcgagacg acgcgttttg tgtaatgaca caatccgaaa gtcgctagca    1680
acacacactc tctacacaaa ctaacccagc tcttcgagta cgcccgagag cacaagttcg    1740
ccctccccgc cgtcaacgtg acctcttcgt ccaccgttgt cgccgttctt gagtctgccc    1800
gagccaacaa gtcccccgtc atcatccaga tgtcccaggg tggcgctgcc tactttgctg    1860
gcaagggtgt cgacaacaag gatcagaccg cctccatcca gggagccatt gccgctgccc    1920
agttcatccg aaccattgct cccgtttacg gcattcccgt catcgtccac accgaccact    1980
gtgcccgaaa gctgctcccc tggctcgacg gtatgctcga cgccgatgag gagtacttca    2040
agactcacgg tgagcccctc ttctcttcac acatggtgga tctctccgag gaggagcacc    2100
ccgagaacat cgccaccacc gccgagtact caagcgagc cgccaagatg aaccagtggc    2160
tcgagatgga gatcggc                                                   2177

<210> SEQ ID NO 48
<211> LENGTH: 1542
<212> TYPE: DNA
<213> ORGANISM: Yarrowia lipolytica

<400> SEQUENCE: 48
tcgaggactt atcctagcct cygaatactt tcaacaagtt acaccccttat tccccaccaa    60 gccgctagat acgccactaa gcaaagttca agagccatcg cacaattatc tacgagtacc    120
gcagcaatca ttcatttcaa ggcacacatg gggtttctct tgcagaaaaa cgcacggttt    180
caaagtataa acgcacatct aggccgagac aagttgcggg gtatggtact agtatttccg    240
ggtgcattcc acgggtgaat gggcgtttag aattgaggca attgccacgg gttgggccac    300
atatgttgag tactcatttc tcctctcaat gaacgtctcc agaatgacat acattctcct    360
ccaacacctt gtggggtaaa cttctgtcag attccacgta acaaggttgg tgtcggaaca    420
acgaaaaagg atcggaacag agcttccggt gtcggtgatt gggcagggggg ctgaggcgtg    480 cctggcgcgt gcgcgtggta gagagagtgt gctacagcag agagatatta ctcgtttgga    540
gctagagatg ccgccgttga agaaattaac gaacgagtaa ctaacagacc attccaggat    600
catcgaggac cgttgtcagc gcccttacta cagaaatgta tgtacagtaa ttacaactgc    660
gcggctgctt gacggatgta tggagtctaa gtaatgagtg cgtacgtagc aacaacagtg    720
tacgcagtac tatagaggaa caattgcccc ggagaagacg gccaggccgc ctagatgaca    780
aattcaacaa ctcacagctg actttctgcc attgccacta gggggggggcc tttttatatg    840 gccaagccaa gctctccacg tcggttgggc tgcaccccaac aataaatggg tagggttgca    900
ccaacaaagg gatgggatgg ggggtagaag atacgaggat aacggggctc aatggcacaa    960
ataagaacga atactgccat taagactcgt gatccagcga ctgacaccat tgcatcatct    1020
aagggcctca aaactacctc ggaactgctg cgctgatctg gacaccacag aggttccgag    1080
cactttaggt tgcaccaaat gtcccaccag gtgcaggcag aaaacgctgg aacagcgtgt    1140
acagtttgtc ttaacaaaaa gtgagggcgc tgaggtcgag cagggtggtg tgacttgtta    1200
tagcctttag agctgcgaaa gcgcgtatgg atttggctca tcaggccaga ttgagggtct    1260
gtggacacat gtcatgttag tgtacttcaa tcgcccctg gatatagccc cgacaatagg    1320
ccgtggcctc atttttttgc cttccgcaca tttccattgc tcggtaccca caccttgctt    1380
ctcctgcact tgccaacctt aatactggtt tacattgacc aacatcttac aagcgggggg    1440
cttgtctagg gtatatataa acagtggctc tcccaatcgg ttgccagtct cttttttcct    1500
```

```
ttctttcccc acagattcga aatctaaact acacatcaca ca                        1542
```

<210> SEQ ID NO 49
<211> LENGTH: 33
<212> TYPE: DNA
<213> ORGANISM: Artificial Sequence
<220> FEATURE:
<223> OTHER INFORMATION: Primer YL33

<400> SEQUENCE: 49

```
tttccatggt acgtcctgta gaaaccccaa ccc                                   33
```

<210> SEQ ID NO 50
<211> LENGTH: 36
<212> TYPE: DNA
<213> ORGANISM: Artificial Sequence
<220> FEATURE:
<223> OTHER INFORMATION: Primer YL34

<400> SEQUENCE: 50

```
cccttaatta atcattgttt gcctccctgc tgcggt                                36
```

<210> SEQ ID NO 51
<211> LENGTH: 436
<212> TYPE: DNA
<213> ORGANISM: Yarrowia lipolytica
<220> FEATURE:
<221> NAME/KEY: misc_feature
<223> OTHER INFORMATION: Promoter TEF

<400> SEQUENCE: 51

```
gaccgggttg gcggcgtatt tgtgtcccaa aaaacagccc caattgcccc aattgacccc      60
aaattgaccc agtagcgggc ccaaccccgg cgagagcccc cttcacccca catatcaaac     120
ctcccccggt tcccacactt gccgttaagg gcgtagggta ctgcagtctg gaatctacgc     180
ttgttcagac tttgtactag tttctttgtc tggccatccg ggtaacccat gccggacgca     240
aaatagacta ctgaaaattt ttttgctttg tggttgggac tttagccaag ggtataaaag     300
accaccgtcc ccgaattacc tttcctcttc ttttctctct ctccttgtca actcacaccc     360
gaaatcgtta agcatttcct tctgagtata agaatcattc aaaggatcca ctagttctag     420
agcggccgct taaacc                                                     436
```

<210> SEQ ID NO 52
<211> LENGTH: 19
<212> TYPE: DNA
<213> ORGANISM: Artificial Sequence
<220> FEATURE:
<223> OTHER INFORMATION: Primer TEF5'

<400> SEQUENCE: 52

```
agagaccggg ttggcggcg                                                   19
```

<210> SEQ ID NO 53
<211> LENGTH: 30
<212> TYPE: DNA
<213> ORGANISM: Artificial Sequence
<220> FEATURE:
<223> OTHER INFORMATION: Primer TEF3'

<400> SEQUENCE: 53

```
ttggatcctt tgaatgattc ttatactcag                                       30
```

<210> SEQ ID NO 54
<211> LENGTH: 29
<212> TYPE: DNA
<213> ORGANISM: Artificial Sequence
<220> FEATURE:
<223> OTHER INFORMATION: Primer XPR5'

<400> SEQUENCE: 54
tttccgcggc ccgagattcc ggcctcttc                              29

<210> SEQ ID NO 55
<211> LENGTH: 31
<212> TYPE: DNA
<213> ORGANISM: Artificial Sequence
<220> FEATURE:
<223> OTHER INFORMATION: Primer XPR3'

<400> SEQUENCE: 55
tttccgcgga cacaatatct ggtcaaattt c                           31

<210> SEQ ID NO 56
<211> LENGTH: 30
<212> TYPE: DNA
<213> ORGANISM: Artificial Sequence
<220> FEATURE:
<223> OTHER INFORMATION: Primer YL1

<400> SEQUENCE: 56
cagtgccaaa agccaaggca ctgagctcgt                             30

<210> SEQ ID NO 57
<211> LENGTH: 31
<212> TYPE: DNA
<213> ORGANISM: Artificial Sequence
<220> FEATURE:
<223> OTHER INFORMATION: Primer YL2

<400> SEQUENCE: 57
gacgagctca gtgccttggc ttttggcact g                           31

<210> SEQ ID NO 58
<211> LENGTH: 36
<212> TYPE: DNA
<213> ORGANISM: Artificial Sequence
<220> FEATURE:
<223> OTHER INFORMATION: Primer YL3

<400> SEQUENCE: 58
gtataagaat cattcaccat ggatccacta gttcta                      36

<210> SEQ ID NO 59
<211> LENGTH: 36
<212> TYPE: DNA
<213> ORGANISM: Artificial Sequence
<220> FEATURE:
<223> OTHER INFORMATION: Primer YL4

<400> SEQUENCE: 59
tagaactagt ggatccatgg tgaatgattc ttatac                      36

<210> SEQ ID NO 60
<211> LENGTH: 36
<212> TYPE: DNA
<213> ORGANISM: Artificial Sequence
<220> FEATURE:
<223> OTHER INFORMATION: Primer YL23

<210> SEQ ID NO 61
<211> LENGTH: 36
<212> TYPE: DNA
<213> ORGANISM: Artificial Sequence
<220> FEATURE:
<223> OTHER INFORMATION: Primer YL24

<400> SEQUENCE: 61
tggcggccgc tctagttaat taactagtgg atccat                          36

<210> SEQ ID NO 62
<211> LENGTH: 35
<212> TYPE: DNA
<213> ORGANISM: Artificial Sequence
<220> FEATURE:
<223> OTHER INFORMATION: Primer YL9

<400> SEQUENCE: 62
tggtaaataa atgatgtcga ctcaggcgac gacgg                           35

<210> SEQ ID NO 63
<211> LENGTH: 35
<212> TYPE: DNA
<213> ORGANISM: Artificial Sequence
<220> FEATURE:
<223> OTHER INFORMATION: Primer YL10

<400> SEQUENCE: 63
ccgtcgtcgc ctgagtcgac atcatttatt tacca                           35

<210> SEQ ID NO 64
<211> LENGTH: 8953
<212> TYPE: DNA
<213> ORGANISM: Artificial Sequence
<220> FEATURE:
<223> OTHER INFORMATION: Plasmid pY5-30

<400> SEQUENCE: 64
ggtggagctc cagcttttgt tccctttagt gagggttaat ttcgagcttg gcgtaatcat    60
ggtcatagct gtttcctgtg tgaaattgtt atccgctcac aattccacac aacatacgag   120
ccggaagcat aaagtgtaaa gcctggggtg cctaatgagt gagctaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata cgcaggaaa gaacatgtga gcaaaaggcc   420
agcaaaaggc caggaaccgt aaaaaggccg cgttgctggc gtttttccat aggctccgcc   480
cccctgacga gcatcacaaa aatcgacgct caagtcagag gtggcgaaac ccgacaggac   540
tataaagata ccaggcgttt ccccctggaa gctccctcgt gcgctctcct gttccgaccc   600
tgccgcttac cggatacctg tccgcctttc tcccttcggg aagcgtggcg ctttctcata   660
gctcacgctg taggtatctc agttcggtgt aggtcgttcg ctccaagctg ggctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
cgaggtatgt aggcggtgct acagagttct tgaagtggtg gcctaactac ggctacacta   900

```
gaaggacagt atttggtatc tgcgctctgc tgaagccagt taccttcgga aaaagagttg    960
gtagctcttg atccggcaaa caaaccaccg ctggtagcgg tggttttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taaagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggtttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc cccccctcga   2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatacatc     3060
atgatgatac tgacagtcat gtcccattgc taaatagaca gactccatct gccgcctcca   3120
actgatgttc tcaatattta agggtcatc tcgcattgtt taataataaa cagactccat   3180
ctaccgcctc caaatgatgt tctcaaaata tattgtatga acttattttt attacttagt   3240
```

```
attattagac aacttacttg ctttatgaaa aacacttcct atttaggaaa caatttataa      3300
tggcagttcg ttcatttaac aatttatgta gaataaatgt tataaatgcg tatgggaaat      3360
cttaaatatg gatagcataa atgatatctg cattgcctaa ttcgaaatca acagcaacga      3420
aaaaaatccc ttgtacaaca taaatagtca tcgagaaata tcaactatca aagaacagct      3480
attcacacgt tactattgag attattattg gacgagaatc acacactcaa ctgtctttct      3540
ctcttctaga aatacaggta caagtatgta ctattctcat tgttcatact tctagtcatt      3600
tcatcccaca tattccttgg atttctctcc aatgaatgac attctatctt gcaaattcaa      3660
caattataat aagatatacc aaagtagcgg tatagtggca atcaaaaagc ttctctggtg      3720
tgcttctcgt atttattttt attctaatga tccattaaag gtatatattt atttcttgtt      3780
atataatcct tttgtttatt acatgggctg gatacataaa ggtattttga tttaattttt      3840
tgcttaaatt caatcccccc tcgttcagtg tcaactgtaa tggtaggaaa ttaccatact      3900
tttgaagaag caaaaaaaat gaagaaaaa aaaaatcgta tttccaggtt agacgttccg      3960
cagaatctag aatgcggtat gcggtacatt gttcttcgaa cgtaaaagtt gcgctccctg      4020
agatattgta cattttgct tttacaagta caagtacatc gtacaactat gtactactgt      4080
tgatgcatcc acaacagttt gttttgtttt tttttgtttt ttttttttct aatgattcat      4140
taccgctatg tatacctact tgtacttgta gtaagccggg ttattggcgt tcaattaatc      4200
atagacttat gaatctgcac ggtgtgcgct gcgagttact tttagcttat gcatgctact      4260
tgggtgtaat attgggatct gttcggaaat caacggatgc tcaaccgatt tcgacagtaa      4320
taatttgaat cgaatcggag cctaaaatga acccgagtat atctcataaa attctcggtg      4380
agaggtctgt gactgtcagt acaaggtgcc ttcattatgc cctcaacctt accatacctc      4440
actgaatgta gtgtacctct aaaaatgaaa tacagtgcca aaagccaagg cactgagctc      4500
gtctaacgga cttgatatac aaccaattaa aacaaatgaa agaaaataca gttctttgta      4560
tcatttgtaa caattaccct gtacaaacta aggtattgaa atcccacaat attcccaaag      4620
tccacccctt tccaaattgt catgcctaca actcatatac caagcactaa cctaccaaac      4680
accactaaaa ccccacaaaa tatatcttac cgaatataca gtaacaagct accaccacac      4740
tcgttgggtg cagtcgccag cttaaagata tctatccaca tcagccacaa ctcccttcct      4800
ttaataaacc gactacaccc ttggctattg aggttatgag tgaatatact gtagacaaga      4860
cactttcaag aagactgttt ccaaaacgta ccactgtcct ccactacaaa cacacccaat      4920
ctgcttcttc tagtcaaggt tgctacaccg gtaaattata aatcatcatt tcattagcag      4980
ggcagggccc tttttataga gtcttataca ctagcggacc ctgccggtag accaacccgc      5040
aggcgcgtca gtttgctcct tccatcaatg cgtcgtagaa acgacttact ccttcttgag      5100
cagctccttg accttgttgg caacaagtct ccgacctcgg aggtggagga agagcctccg      5160
atatcggcgg tagtgatacc agcctcgacg gactccttga cggcagcctc aacagcgtca      5220
ccggcgggct tcatgttaag agagaacttg agcatcatgg cggcagacag aatggtggca      5280
atggggttga ccttctgctt gccgagatcg ggggcagatc cgtgacaggg ctcgtacaga      5340
ccgaacgcct cgttggtgtc gggcagagaa gccagagagg cggagggcag cagacccaga      5400
gaaccgggga tgacggaggc ctcgtcggag atgtatatcgc caaacatgtt ggtggtgatg      5460
atgataccat tcatcttgga gggctgcttg atgaggatca tggcggccga gtcgatcagc      5520
tggtggttga gctcgagctg ggggaattcg tccttgagga ctcgagtgac agtctttcgc      5580
caaagtcgag aggaggccag cacgttggcc ttgtcaagag accacacggg aagagggggg      5640
```

```
ttgtgctgaa gggccaggaa ggcggccatt cgggcaattc gctcaacctc aggaacggag    5700
taggtctcgg tgtcggaagc gacgccagat ccgtcatcct cctttcgctc tccaaagtag    5760
atacctccga cgagctctcg gacaatgatg aagtcggtgc cctcaacgtt tcggatgggg    5820
gagagatcgg cgagcttggg cgacagcagc tggcagggtc gcaggttggc gtacaggttc    5880
aggtcctttc gcagcttgag gagaccctgc tcgggtcgca cgtcggttcg tccgtcggga    5940
gtggtccata cggtgttggc agcgcctccg acagcaccga gcataataga gtcagccttt    6000
cggcagatgt cgagagtagc gtcggtgatg ggctcgccct ccttctcaat ggcagctcct    6060
ccaatgagtc ggtcctcaaa cacaaactcg gtgccggagg cctcagcaac agacttgagc    6120
accttgacgg cctcggcaat cacctcgggg ccacagaagt cgccgccgag aagaacaatc    6180
ttcttggagt cagtcttggt cttcttagtt tcgggttcca ttgtggatgt gtgtggttgt    6240
atgtgtgatg tggtgtgtgg agtgaaaatc tgtggctggc aaacgctctt gtatatatac    6300
gcacttttgc ccgtgctatg tggaagacta aacctccgaa gattgtgact caggtagtgc    6360
ggtatcggct agggacccaa accttgtcga tgccgatagc gctatcgaac gtaccccagc    6420
cggccgggag tatgtcggag gggacatacg agatcgtcaa gggtttgtgg ccaactggta    6480
aataaatgat gtcgactcag gcgacgacgg aattcctgca gcccatctgc agaattcagg    6540
agagaccggg ttggcggcgt atttgtgtcc caaaaaacag ccccaattgc cccaattgac    6600
cccaaattga cccagtagcg ggcccaaccc cggcgagagc cccttcacc ccacatatca     6660
aacctccccc ggttcccaca cttgccgtta agggcgtagg gtactgcagt ctggaatcta    6720
cgcttgttca gactttgtac tagttttcttt gtctggccat ccgggtaacc catgccggac    6780
gcaaaataga ctactgaaaa tttttttgct ttgtggttgg gactttagcc aagggtataa    6840
aagaccaccg tccccgaatt accttttcctc ttcttttctc tctctccttg tcaactcaca    6900
cccgaaatcg ttaagcattt ccttctgagt ataagaatca ttcaccatgg atggtacgtc    6960
ctgtagaaac cccaacccgt gaaatcaaaa aactcgacgg cctgtgggca ttcagtctgg    7020
atcgcgaaaa ctgtggaatt gatcagcgtt ggtgggaaag cgcgttacaa gaaagccggg    7080
caattgctgt gccaggcagt tttaacgatc agttcgccga tgcagatatt cgtaattatg    7140
cgggcaacgt ctggtatcag cgcgaagtct ttataccgaa aggttgggca ggccagcgta    7200
tcgtgctgcg tttcgatgcg gtcactcatt acggcaaagt gtgggtcaat aatcaggaag    7260
tgatggagca tcagggcggc tatacgccat ttgaagccga tgtcacgccg tatgttattg    7320
ccgggaaaag tgtacgtatc accgtttgtg tgaacaacga actgaactgg cagactatcc    7380
cgccgggaat ggtgattacc gacgaaaacg gcaagaaaaa gcagtcttac ttccatgatt    7440
tctttaacta tgccgggatc catcgcagcg taatgctcta caccacgccg aacacctggg    7500
tggacgatat caccgtggtg acgcatgtcg cgcaagactg taaccacgcg tctgttgact    7560
ggcaggtggt ggccaatggt gatgtcagcg ttgaactgcg tgatgcggat caacaggtgg    7620
ttgcaactgg acaaggcact agcgggactt tgcaagtggt gaatccgcac ctctggcaac    7680
cgggtgaagg ttatctctat gaactgtgcg tcacagccaa agccagaca gagtgtgata     7740
tctaccgct cgcgtcggc atccggtcag tggcagtgaa gggcgaacag ttcctgatta      7800
accacaaacc gttctacttt actggctttg gtcgtcatga agatgcggac ttacgtggca    7860
aaggattcga taacgtgctg atggtgcacg accacgcatt aatggactgg attgggccaa    7920
actcctaccg tacctcgcat taccccttacg ctgaagagat gctcgactgg gcagatgaac    7980
```

```
atggcatcgt ggtgattgat gaaactgctg ctgtcggctt taacctctct ttaggcattg    8040
gtttcgaagc gggcaacaag ccgaaagaac tgtacagcga agaggcagtc aacgggaaa     8100 ctcagcaagc gcacttacag gcgattaaag agctgatagc gcgtgacaaa aaccacccaa    8160
gcgtggtgat gtggagtatt gccaacgaac cggatacccg tccgcaagtg cacgggaata    8220
tttcgccact ggcggaagca acgcgtaaac tcgacccgac gcgtccgatc acctgcgtca    8280
atgtaatgtt ctgcgacgct cacaccgata ccatcagcga tctctttgat gtgctgtgcc    8340
tgaaccgtta ttacggatgg tatgtccaaa gcggcgattt ggaaacggca gagaaggtac    8400
tggaaaaaga acttctggcc tggcaggaga aactgcatca gccgattatc atcaccgaat    8460
acggcgtgga tacgttagcc gggctgcact caatgtacac cgacatgtgg agtgaagagt    8520
atcagtgtgc atggctggat atgtatcacc gcgtctttga tcgcgtcagc gccgtcgtcg    8580
gtgaacaggt atggaatttc gccgattttg cgacctcgca aggcatattg cgcgttggcg    8640
gtaacaagaa agggatcttc actcgcgacc gcaaaccgaa gtcggcggct tttctgctgc    8700
aaaaacgctg gactggcatg aacttcggtg aaaaaccgca gcaggaggc  aaacaatgat    8760 taattaacta gagcggccgc caccgcggcc cgagattccg gcctcttcgg ccgccaagcg    8820
acccgggtgg acgtctagag gtacctagca attaacagat agtttgccgg tgataattct    8880 cttaaccctcc cacactcctt tgacataacg atttatgtaa cgaaactgaa atttgaccag    8940
atattgtgtc cgc                                                       8953

<210> SEQ ID NO 65
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)
<223> OTHER INFORMATION: n is a, c, g, or t

<400> SEQUENCE: 65 mammatgnhs                                                             10

<210> SEQ ID NO 66
<211> LENGTH: 971
<212> TYPE: DNA
<213> ORGANISM: Yarrowia lipolytica
<220> FEATURE:
<221> NAME/KEY: misc_feature
<223> OTHER INFORMATION: Promoter GPD

<400> SEQUENCE: 66
gacgcagtag gatgtcctgc acgggtcttt ttgtggggtg tggagaaagg ggtgcttgga      60
gatggaagcc ggtagaaccg ggctgcttgt gcttggagat ggaagccggt agaaccgggc    120
tgcttggggg gatttgggc cgctgggctc caaagagggg taggcatttc gttgggtta     180 cgtaattgcg gcatttgggt cctgcgcgca tgtcccattg gtcagaatta gtccggatag    240
gagacttatc agccaatcac agcgccggat ccacctgtag gttgggttgg gtgggagcac    300
ccctccacag agtagagtca aacagcagca gcaacatgat agttgggggt gtgcgtgtta    360
aaggaaaaaa aagaagcttg ggttatattc ccgctctatt tagaggttgc gggatagacg    420
ccgacggagg gcaatggcgc catggaacct tgcggatatc gatacgccgc ggcggactgc    480
gtccgaacca gctccagcag cgttttttcc gggccattga gccgactgcg acccgccaa     540 cgtgtcttgg cccacgcact catgtcatgt tggtgttggg aggccacttt ttaagtagca    600
```

```
caaggcacct agctcgcagc aaggtgtccg aaccaaagaa gcggctgcag tggtgcaaac    660
ggggcggaaa cggcgggaaa aagccacggg ggcacgaatt gaggcacgcc ctcgaatttg    720
agacgagtca cggccccatt cgcccgcgca atggctcgcc aacgcccggt cttttgcacc    780
acatcaggtt accccaagcc aaacctttgt gttaaaaagc ttaacatatt ataccgaacg    840
taggtttggg cgggcttgct ccgtctgtcc aaggcaacat ttatataagg gtctgcatcg    900
ccggctcaat tgaatctttt ttcttcttct cttctctata ttcattcttg aattaaacac    960
acatcaacat g                                                        971
```

```
<210> SEQ ID NO 67
<211> LENGTH: 878
<212> TYPE: DNA
<213> ORGANISM: Yarrowia lipolytica
<220> FEATURE:
<221> NAME/KEY: misc_feature
<223> OTHER INFORMATION: Promoter GPM

<400> SEQUENCE: 67
```

```
gcctctgaat actttcaaca agttacaccc ttcattaatt ctcacgtgac acagattatt     60
aacgtctcgt accaaccaca gattacgacc cattcgcagt cacagttcac tagggtttgg    120
gttgcatccg ttgagagcgg tttgttttta accttctcca tgtgctcact caggttttgg    180
gttcagatca aatcaaggcg tgaaccactt tgtttgagga caaatgtgac acaaccaacc    240
agtgtcaggg gcaagtccgt gacaaagggg aagatacaat gcaattactg acagttacag    300
actgcctcga tgcccctaacc ttgccccaaa ataagacaac tgtcctcgtt taagcgcaac    360
cctattcagc gtcacgtcat aatagcgttt ggatagcact agtctatgag gagcgtttta    420
tgttgcggtg agggcgattg tgctcatat gggttcaatt gaggtggcgg aacgagctta    480
gtcttcaatt gaggtgcgag cgacacaatt gggtgtcacg tggcctaatt gacctcgggt    540
cgtggagtcc ccagttatac agcaaccacg aggtgcatgg gtaggagacg tcaccagaca    600
atagggtttt ttttggactg gagagggttg ggcaaaagcg ctcaacgggc tgtttgggga    660
gctgtggggg aggaattggc gatatttgtg aggttaacgg ctccgatttg cgtgttttgt    720
cgctcctgca tctccccata cccatatctt ccctcccac ctcttccac gataatttta    780 cggatcagca ataaggttcc ttctcctagt ttccacgtcc atatatatct atgctgcgtc    840
gtccttttcg tgacatcacc aaaacacata caaaaatg                           878
```

```
<210> SEQ ID NO 68
<211> LENGTH: 30
<212> TYPE: DNA
<213> ORGANISM: Artificial Sequence
<220> FEATURE:
<223> OTHER INFORMATION: Primer YL211

<400> SEQUENCE: 68
```

```
tttgtcgacg cagtaggatg tcctgcacgg                                     30
```

```
<210> SEQ ID NO 69
<211> LENGTH: 34
<212> TYPE: DNA
<213> ORGANISM: Artificial Sequence
<220> FEATURE:
<223> OTHER INFORMATION: Primer YL212

<400> SEQUENCE: 69
```

```
tttccatggt tgatgtgtgt ttaattcaag aatg                                34
```

<210> SEQ ID NO 70
<211> LENGTH: 1174
<212> TYPE: DNA
<213> ORGANISM: Yarrowia lipolytica
<220> FEATURE:
<221> NAME/KEY: misc_feature
<223> OTHER INFORMATION: Promoter GPDIN

<400> SEQUENCE: 70

```
aaacacgcag taggatgtcc tgcacgggtc tttttgtggg gtgtggagaa agggtgctt      60
ggagatggaa gccggtagaa ccgggctgct tgtgcttgga gatggaagcc ggtagaaccg    120
ggctgcttgg ggggatttgg ggccgctggg ctccaaagag gggtaggcat ttcgttgggg    180
ttacgtaatt gcggcatttg ggtcctgcgc gcatgtccca ttggtcagaa ttagtccgga    240
taggagactt atcagccaat cacagcgccg gatccacctg taggttgggt tgggtgggag    300
caccccctcca cagagtagag tcaaacagca gcagcaacat gatagttggg ggtgtgcgtg    360
ttaaaggaaa aaaagaagc ttgggttata ttcccgctct atttagaggt tgcgggatag    420
acgccgacgg agggcaatgg cgctatgaa ccttgcggat atccatacgc cgcggcggac      480
tgcgtccgaa ccagctccag cagcgttttt tccgggccat tgagccgact gcgacccgc     540
caacgtgtct tggcccacgc actcatgtca tgttggtgtt gggaggccac tttttaagta    600
gcacaaggca cctagctcgc agcaaggtgt ccgaaccaaa gaagcggctg cagtggtgca    660
acgggggcgg aaacggcggg aaaaagccac ggggggcacga attgaggcac gccctcgaat    720
ttgagacgag tcaggcccc attcgcccgc gcaatggctc gccaacgccc ggtcttttgc     780
accacatcag gttaccccaa gccaaaccctt tgtgttaaaa agcttaacat attataccga    840
acgtaggttt gggcgggctt gctccgtctg tccaaggcaa catttatata agggtctgca    900
tcgccggctc aattgaatct ttttcttct tctcttctct atattcattc ttgaattaaa    960
cacacatcaa catggccatc aaagtcggta ttaacggatt cgggcgaatc ggacgaattg   1020
tgagtaccat agaaggtgat ggaaacatga cccaacagaa acagatgaca agtgtcatcg   1080
acccaccaga gcccaattga gctcatacta acagtcgaca acctgtcgaa ccaattgatg   1140
actccccgac aatgtactaa cacaggtcct gccc                              1174
```

<210> SEQ ID NO 71
<211> LENGTH: 32
<212> TYPE: DNA
<213> ORGANISM: Artificial Sequence
<220> FEATURE:
<223> OTHER INFORMATION: Primer YL377

<400> SEQUENCE: 71

```
tttccatggg caggacctgt gttagtacat tg                                  32
```

<210> SEQ ID NO 72
<211> LENGTH: 33
<212> TYPE: DNA
<213> ORGANISM: Artificial Sequence
<220> FEATURE:
<223> OTHER INFORMATION: Primer YL203

<400> SEQUENCE: 72

```
tttccatggt tgtatgtgtt ttggtgatgt cac                                 33
```

<210> SEQ ID NO 73
<211> LENGTH: 33
<212> TYPE: DNA

```
<213> ORGANISM: Artificial Sequence
<220> FEATURE:
<223> OTHER INFORMATION: Primer YL204

<400> SEQUENCE: 73
tttgtcgacc gtttaagcgc aaccctattc agc                                33

<210> SEQ ID NO 74
<211> LENGTH: 1001
<212> TYPE: DNA
<213> ORGANISM: Yarrowia lipolytica
<220> FEATURE:
<221> NAME/KEY: misc_feature
<223> OTHER INFORMATION: Promoter FBA

<400> SEQUENCE: 74
taaacagtgt acgcagtact atagaggaac aattgccccg gagaagacgg ccaggccgcc      60
tagatgacaa attcaacaac tcacagctga ctttctgcca ttgccactag ggggggcctt     120
tttatatggc caagccaagc tctccacgtc ggttgggctg cacccaacaa taaatgggta     180
gggttgcacc aacaaaggga tgggatgggg ggtagaagat acgaggataa cggggctcaa     240
tggcacaaat aagaacgaat actgccatta agactcgtga tccagcgact gacaccattg     300
catcatctaa gggcctcaaa actacctcgg aactgctgcg ctgatctgga caccacagag     360
gttccgagca ctttaggttg caccaaatgt cccaccaggt gcaggcagaa aacgctggaa     420
cagcgtgtac agtttgtctt aacaaaaagt gagggcgctg aggtcgagca gggtggtgtg     480
acttgttata gcctttagag ctgcgaaagc gcgtatggat ttggctcatc aggccagatt     540
gagggtctgt ggacacatgt catgttagtg tacttcaatc gccccctgga tatagccccg     600
acaataggcc gtggcctcat tttttgcct tccgcacatt tccattgctc ggtacccaca      660
ccttgcttct cctgcacttg ccaaccttaa tactggttta cattgaccaa catcttacaa     720 gcgggggggct tgtctagggt atatataaac agtggctctc ccaatcggtt gccagtctct    780
tttttccttt ctttccccac agattcgaaa tctaaactac acatcacaca atgcctgtta     840
ctgacgtcct taagcgaaag tccggtgtca tcgtcggcga cgatgtccga gccgtgagta     900
tccacgacaa gatcagtgtc gagacgacgc gttttgtgta atgacacaat ccgaaagtcg     960
ctagcaacac acactctcta cacaaactaa cccagctctc c                        1001

<210> SEQ ID NO 75
<211> LENGTH: 33
<212> TYPE: DNA
<213> ORGANISM: Artificial Sequence
<220> FEATURE:
<223> OTHER INFORMATION: Primer ODMW314

<400> SEQUENCE: 75
cgtgccatgg tgtgatgtgt agtttagatt tcg                                33

<210> SEQ ID NO 76
<211> LENGTH: 39
<212> TYPE: DNA
<213> ORGANISM: Artificial Sequence
<220> FEATURE:
<223> OTHER INFORMATION: Primer YL341

<400> SEQUENCE: 76
tttgtcgacg tttaaacagt gtacgcagta ctatagagg                          39

<210> SEQ ID NO 77
```

```
<211> LENGTH: 995
<212> TYPE: DNA
<213> ORGANISM: Yarrowia lipolytica
<220> FEATURE:
<221> NAME/KEY: misc_feature
<223> OTHER INFORMATION: Promoter FBAIN

<400> SEQUENCE: 77
agtgtacgca gtactataga ggaacaattg ccccggagaa gacggccagg ccgcctagat     60
gacaaattca acaactcaca gctgactttc tgccattgcc actagggggg ggccttttta    120
tatggccaag ccaagctctc cacgtcggtt gggctgcacc caacaataaa tgggtagggt    180
tgcaccaaca aagggatggg atgggggta gaagatacga ggataacggg gctcaatggc    240
acaaataaga acgaatactg ccattaagac tcgtgatcca gcgactgaca ccattgcatc    300
atctaagggc ctcaaaacta cctcggaact gctgcgctga tctggacacc acagaggttc    360
cgagcacttt aggttgcacc aaatgtccca ccaggtgcag gcagaaaacg ctggaacagc    420
gtgtacagtt tgtcttaaca aaaagtgagg gcgctgaggt cgagcagggt ggtgtgactt    480
gttatagcct ttagagctgc gaaagcgcgt atggatttgg ctcatcaggc cagattgagg    540
gtctgtggac acatgtcatg ttagtgtact tcaatcgccc cctggatata gccccgacaa    600
taggccgtgg cctcatttt ttgccttccg cacatttcca ttgctcggta cccacacctt    660
gcttctcctg cacttgccaa ccttaatact ggtttacatt gaccaacatc ttacaagcgg    720
ggggcttgtc tagggtatat ataaacagtg gctctcccaa tcggttgcca gtctcttttt    780
tcctttcttt ccccacagat tcgaaatcta aactacacat cacacaatgc ctgttactga    840
cgtccttaag cgaaagtccg gtgtcatcgt cggcgacgat gtccgagccg tgagtatcca    900
cgacaagatc agtgtcgaga cgacgcgttt tgtgtaatga cacaatccga aagtcgctag    960
caacacacac tctctacaca aactaaccca gctct                               995

<210> SEQ ID NO 78
<211> LENGTH: 34
<212> TYPE: DNA
<213> ORGANISM: Artificial Sequence
<220> FEATURE:
<223> OTHER INFORMATION: Primer ODMW320

<400> SEQUENCE: 78
cgtgccatgg agagctgggt tagtttgtgt agag                                 34

<210> SEQ ID NO 79
<211> LENGTH: 39
<212> TYPE: DNA
<213> ORGANISM: Artificial Sequence
<220> FEATURE:
<223> OTHER INFORMATION: Primer ODMW341

<400> SEQUENCE: 79
tttgtcgacg tttaaacagt gtacgcagta ctatagagg                            39

<210> SEQ ID NO 80
<211> LENGTH: 21
<212> TYPE: DNA
<213> ORGANISM: Artificial Sequence
<220> FEATURE:
<223> OTHER INFORMATION: Primer YL-URA-16F

<400> SEQUENCE: 80
gctcgagcta acgtccacaa g                                               21
```

<210> SEQ ID NO 81
<211> LENGTH: 18
<212> TYPE: DNA
<213> ORGANISM: Artificial Sequence
<220> FEATURE:
<223> OTHER INFORMATION: Primer YL-URA-78R

<400> SEQUENCE: 81
cttggctgcc acgagctt                                                    18

<210> SEQ ID NO 82
<211> LENGTH: 22
<212> TYPE: DNA
<213> ORGANISM: Artificial Sequence
<220> FEATURE:
<223> OTHER INFORMATION: Primer GUS-767F

<400> SEQUENCE: 82
ccaaaagcca gacagagtgt ga                                               22

<210> SEQ ID NO 83
<211> LENGTH: 22
<212> TYPE: DNA
<213> ORGANISM: Artificial Sequence
<220> FEATURE:
<223> OTHER INFORMATION: Primer GUS-891R

<400> SEQUENCE: 83
ttcatgacga ccaaagccag ta                                               22

<210> SEQ ID NO 84
<211> LENGTH: 1052
<212> TYPE: DNA
<213> ORGANISM: Artificial Sequence
<220> FEATURE:
<223> OTHER INFORMATION: GPM::GPDIN chimeric Yarrowia lipolytica
      promoter

<400> SEQUENCE: 84
gtcgaccatt aattctcacg tgacacagat tattaacgtc tcgtaccaac cacagattac      60
gacccattcg cagtcacagt tcactagggt ttgggttgca tccgttgaga gcggtttgtt     120
tttaaccttc tccatgtgct cactcaggtt ttgggttcag atcaaatcaa ggcgtgaacc     180
actttgtttg aggacaaatg tgacacaacc aaccagtgtc aggggcaagt ccgtgacaaa     240
ggggaagata caatgcaatt actgacagtt acagactgcc tcgatgccct aaccttgccc     300
caaaataaga caactgtcct cgtttaagcg caaccctatt cagcgtcacg tcataatagc     360
gtttggatag cactagtcta tgaggagcgt tttatgttgc ggtgagggcg attggtgctc     420
atatgggttc aattgaggtg gcggaacgag cttagtcttc aattgaggtg cgagcgacac     480
aattgggtgt cacgtggcct aattgacctc gggtcgtgga gtccccagtt atacagcaac     540
cacgaggtgc atgggtagga gacgtcacca gacaataggg ttttttttgg actggagagg     600
gttgggcaaa agcgctcaac gggctgtttg gggagctgtg ggggaggaat tggcgatatt     660
tgtgaggtta acggctccga tttgcgtgtt ttgtcgctcc tgcatctccc catacccata     720
tcttccctcc ccacctcttt ccacgataat tttacggatc agcaataagg ttccttctcc     780
tagtttccac gtccatatat atctatgctg cgtcgtcctt ttcgtgacat caccaaaaca     840
catacaacca tggccatcaa agtcggtatt aacggattcg ggcgaatcgg acgaattgtg     900
agtaccatag aaggtgatgg aaacatgacc caacagaaac agatgacaag tgtcatcgac     960

```
ccaccagagc ccaattgagc tcatactaac agtcgacaac ctgtcgaacc aattgatgac    1020
tccccgacaa tgtactaaca caggtcctgc cc                                  1052
```

<210> SEQ ID NO 85
<211> LENGTH: 39
<212> TYPE: DNA
<213> ORGANISM: Artificial Sequence
<220> FEATURE:
<223> OTHER INFORMATION: Primer YL5

<400> SEQUENCE: 85

```
ccccctcga ggtcgatggt gtcgataagc ttgatatcg                             39
```

<210> SEQ ID NO 86
<211> LENGTH: 39
<212> TYPE: DNA
<213> ORGANISM: Artificial Sequence
<220> FEATURE:
<223> OTHER INFORMATION: Primer YL6

<400> SEQUENCE: 86

```
cgatatcaag cttatcgaca ccatcgacct cgagggggg                            39
```

<210> SEQ ID NO 87
<211> LENGTH: 37
<212> TYPE: DNA
<213> ORGANISM: Artificial Sequence
<220> FEATURE:
<223> OTHER INFORMATION: Primer YL7

<400> SEQUENCE: 87

```
caaccgattt cgacagttaa ttaataattt gaatcga                              37
```

<210> SEQ ID NO 88
<211> LENGTH: 37
<212> TYPE: DNA
<213> ORGANISM: Artificial Sequence
<220> FEATURE:
<223> OTHER INFORMATION: Primer YL8

<400> SEQUENCE: 88

```
tcgattcaaa ttattaatta actgtcgaaa tcggttg                              37
```

<210> SEQ ID NO 89
<211> LENGTH: 33
<212> TYPE: DNA
<213> ORGANISM: Artificial Sequence
<220> FEATURE:
<223> OTHER INFORMATION: Primer YL61

<400> SEQUENCE: 89

```
acaattccac acaacgtacg agccggaagc ata                                  33
```

<210> SEQ ID NO 90
<211> LENGTH: 33
<212> TYPE: DNA
<213> ORGANISM: Artificial Sequence
<220> FEATURE:
<223> OTHER INFORMATION: Primer YL62

<400> SEQUENCE: 90

```
tatgcttccg gctcgtacgt tgtgtggaat tgt                                  33
```

<210> SEQ ID NO 91
<211> LENGTH: 18

<210> SEQ ID NO 91
<211> LENGTH: 18
<212> TYPE: DNA
<213> ORGANISM: Artificial Sequence
<220> FEATURE:
<223> OTHER INFORMATION: Primer GPDsense

<400> SEQUENCE: 91
atacgagatc gtcaaggg                                                   18

<210> SEQ ID NO 92
<211> LENGTH: 26
<212> TYPE: DNA
<213> ORGANISM: Artificial Sequence
<220> FEATURE:
<223> OTHER INFORMATION: Primer GPDantisense

<400> SEQUENCE: 92
gcggccgcgg attgatgtgt gtttaa                                          26

<210> SEQ ID NO 93
<211> LENGTH: 1209
<212> TYPE: DNA
<213> ORGANISM: Fusarium monoliforme

<400> SEQUENCE: 93
atggcgactc gacagcgaac tgccaccact gttgtggtcg aggaccttcc caaggtcact      60
cttgaggcca agtctgaacc tgtgttcccc gatatcaaga ccatcaagga tgccattccc     120
gcgcactgct tccagccctc gctcgtcacc tcattctact acgtcttccg cgattttgcc     180
atggtctctg ccctcgtctg gctgctctc acctacatcc ccagcatccc cgaccagacc      240
ctccgcgtcg cagcttggat ggtctacggc ttcgtccagg gtctgttctg caccggtgtc     300
tggattctcg gccatgagtg cggccacggt gctttctctc tccacggaaa ggtcaacaat     360
gtgaccggct ggttcctcca ctcgttcctc ctcgtcccct acttcagctg gaagtactct     420
caccaccgcc accaccgctt caccggccac atggatctcg acatggcttt cgtccccaag     480
actgagccca gccctccaa gtcgctcatg attgctggca ttgacgtcgc cgagcttgtt      540
gaggacaccc ccgctgctca gatggtcaag ctcatcttcc accagctttt cggatggcag     600
gcgtacctct tcttcaacgc tagctctggc aagggcagca agcagtggga gcccaagact     660
ggcctctcca gtggttccg agtcagtcac ttcgagccta ccagcgctgt cttccgcccc      720
aacgaggcca tcttcatcct catctccgat atcggtcttg ctctaatggg aactgctctg     780
tactttgctt ccaagcaagt tggtgtttcg accattctct tcctctacct tgttccctac     840
ctgtgggttc accactggct cgttgccatt acctacctcc accaccacca caccgagctc     900
cctcactaca ccgctgaggg ctggacctac gtcaagggag ctctcgccac tgtcgaccgt     960
gagtttggct tcatcggaaa gcacctcttc cacggtatca ttgagaagca cgttgttcac    1020
catctcttcc ctaagatccc cttctacaag gctgacgagg ccaccgaggc catcaagccc    1080
gtcattggcg accactactg ccacgacgac cgaagcttcc tgggccagct gtggaccatc    1140
ttcggcacgc tcaagtacgt cgagcacgac cctgcccgac ccggtgccat gcgatggaac    1200
aaggactag                                                           1209

<210> SEQ ID NO 94
<211> LENGTH: 402
<212> TYPE: PRT
<213> ORGANISM: Fusarium monoliforme

<400> SEQUENCE: 94

```
Met Ala Thr Arg Gln Arg Thr Ala Thr Thr Val Val Glu Asp Leu
1               5                   10                  15

Pro Lys Val Thr Leu Glu Ala Lys Ser Glu Pro Val Phe Pro Asp Ile
            20                  25                  30

Lys Thr Ile Lys Asp Ala Ile Pro Ala His Cys Phe Gln Pro Ser Leu
            35                  40                  45

Val Thr Ser Phe Tyr Tyr Val Phe Arg Asp Phe Ala Met Val Ser Ala
    50                  55                  60

Leu Val Trp Ala Ala Leu Thr Tyr Ile Pro Ser Ile Pro Asp Gln Thr
65              70                  75                  80

Leu Arg Val Ala Ala Trp Met Val Tyr Gly Phe Val Gln Gly Leu Phe
                85                  90                  95

Cys Thr Gly Val Trp Ile Leu Gly His Glu Cys Gly His Gly Ala Phe
                100                 105                 110

Ser Leu His Gly Lys Val Asn Asn Val Thr Gly Trp Phe Leu His Ser
        115                 120                 125

Phe Leu Leu Val Pro Tyr Phe Ser Trp Lys Tyr Ser His Arg His
    130                 135                 140

His Arg Phe Thr Gly His Met Asp Leu Asp Met Ala Phe Val Pro Lys
145                 150                 155                 160

Thr Glu Pro Lys Pro Ser Lys Ser Leu Met Ile Ala Gly Ile Asp Val
                165                 170                 175

Ala Glu Leu Val Glu Asp Thr Pro Ala Ala Gln Met Val Lys Leu Ile
            180                 185                 190

Phe His Gln Leu Phe Gly Trp Gln Ala Tyr Leu Phe Phe Asn Ala Ser
    195                 200                 205

Ser Gly Lys Gly Ser Lys Gln Trp Glu Pro Lys Thr Gly Leu Ser Lys
    210                 215                 220

Trp Phe Arg Val Ser His Phe Glu Pro Thr Ser Ala Val Phe Arg Pro
225                 230                 235                 240

Asn Glu Ala Ile Phe Ile Leu Ile Ser Asp Ile Gly Leu Ala Leu Met
                245                 250                 255

Gly Thr Ala Leu Tyr Phe Ala Ser Lys Gln Val Gly Val Ser Thr Ile
            260                 265                 270

Leu Phe Leu Tyr Leu Val Pro Tyr Leu Trp Val His His Trp Leu Val
    275                 280                 285

Ala Ile Thr Tyr Leu His His Thr Glu Leu Pro His Tyr Thr
290                 295                 300

Ala Glu Gly Trp Thr Tyr Val Lys Gly Ala Leu Ala Thr Val Asp Arg
305                 310                 315                 320

Glu Phe Gly Phe Ile Gly Lys His Leu Phe His Gly Ile Ile Glu Lys
                325                 330                 335

His Val Val His His Leu Phe Pro Lys Ile Pro Phe Tyr Lys Ala Asp
            340                 345                 350

Glu Ala Thr Glu Ala Ile Lys Pro Val Ile Gly Asp His Tyr Cys His
            355                 360                 365

Asp Asp Arg Ser Phe Leu Gly Gln Leu Trp Thr Ile Phe Gly Thr Leu
    370                 375                 380

Lys Tyr Val Glu His Asp Pro Ala Arg Pro Gly Ala Met Arg Trp Asn
385                 390                 395                 400

Lys Asp
```

<210> SEQ ID NO 95

```
<211> LENGTH: 36
<212> TYPE: DNA
<213> ORGANISM: Artificial Sequence
<220> FEATURE:
<223> OTHER INFORMATION: Primer P192

<400> SEQUENCE: 95
aaatatgcgg ccgcacaatg gcgactcgac agcgaa                           36

<210> SEQ ID NO 96
<211> LENGTH: 34
<212> TYPE: DNA
<213> ORGANISM: Artificial Sequence
<220> FEATURE:
<223> OTHER INFORMATION: Primer P193

<400> SEQUENCE: 96
tttatagcgg ccgcctagtc cttgttccat cgca                             34

<210> SEQ ID NO 97
<211> LENGTH: 146
<212> TYPE: DNA
<213> ORGANISM: Yarrowia lipolytica

<400> SEQUENCE: 97
gtgagtacca tagaaggtga tggaaacatg acccaacaga aacagatgac aagtgtcatc    60
gacccaccag agcccaattg agctcatact aacagtcgac aacctgtcga accaattgat   120
gactccccga caatgtacta acacag                                       146
```

GLYCERALDEHYDE-3-PHOSPHATE DEHYDROGENASE AND PHOSPHOGLYCERATE MUTASE REGULATORY SEQUENCES FOR GENE EXPRESSION IN OLEAGINOUS YEAST

This application is a continuation in part of U.S. application Ser. No. 10/869,630, filed Jun. 16, 2004, now U.S. Pat. No. 7,259,255, which claims the benefit of U.S. Provisional Application 60/482,263, filed Jun. 25, 2003, now expired.

FIELD OF THE INVENTION

This invention is in the field of biotechnology. More specifically, this invention pertains to promoter regions and other regulatory sequences (i.e., introns and enhancers) isolated from *Yarrowia lipolytica* that are useful for gene expression in oleaginous yeast.

BACKGROUND OF THE INVENTION

Oleaginous yeast are defined as those organisms that are naturally capable of oil synthesis and accumulation, wherein oil accumulation can be up to about 80% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

The technology for growing oleaginous yeast with high oil content is well developed (for example, see EP 0 005 277B1; Ratledge, C., *Prog. Ind. Microbiol.* 16:119-206 (1982)). And, these organisms have been commercially used for a variety of purposes in the past. For example, various strains of *Yarrowa lipolytica* have historically been used for the manufacture and production of: isocitrate lyase; lipases; polyhydroxyalkanoates; citric acid; erythritol; 2-oxoglutaric acid; γ-decalactone; γ-dodecalactone; and pyruvic acid. Most recently, however, the natural abilities of oleaginous yeast have been enhanced by advances in genetic engineering, resulting in organisms capable of producing polyunsaturated fatty acids ("PUFAs"). Specifically, Picataggio et al. have demonstrated that *Yarrowia lipolytica* can be engineered for production of ω-3 and ω-6 fatty acids, by introducing and expressing genes encoding the ω-3/ω-6 biosynthetic pathway (co-pending U.S. patent application Ser. No. 10/840,579 and No. 60/624,812, herein incorporated by reference in their entirety).

Recombinant production of any heterologous protein is generally accomplished by constructing an expression cassette in which the DNA coding for the protein of interest is placed under the control of appropriate regulatory sequences (i.e., promoters) suitable for the host cell. The expression cassette is then introduced into the host cell (usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., oleaginous yeast) for recombinant production of proteins generally requires the availability of promoters that are suitable for controlling the expression of a protein of interest in the host cell.

A variety of strong promoters have been isolated from *Saccharomyces cerevisiae* that are useful for heterologous gene expression in yeast. For example, a glyceraldehyde-3-phosphate dehydrogenase (GPD) promoter was described by Bitter, G. A., and K. M. Egan (*Gene* 32(3):263-274 (1984)); and, a phosphoglycerate mutase (GPM1) promoter was investigated by Rodicio, R. et al. (*Gene* 125(2): 125-133 (1993)).

Several promoters have also been isolated from *Yarrowia lipolytica* that have been suitable for the recombinant expression of proteins. For example, U.S. Pat. No. 4,937,189 and EP220864 (Davidow et al.) disclose the sequence of the XPR2 gene (which encodes an inducible alkaline extracellular protease) and upstream promoter region for use in expression of heterologous proteins. However, this promoter is only active at a pH above 6.0 on media lacking preferred carbon and nitrogen sources; and, full induction requires high levels of peptone in the culture media. Subsequent analysis of the XPR2 promoter sequence by Blanchin-Roland, S. et al. (EP832258; *Mol. Cell Biol.* 14(1):327-338 (1994)) determined that hybrid promoters containing only parts of the XPR2 promoter sequence may be used to obtain high level expression in *Yarrowia*, without the limitations resulting from use of the complete promoter sequence.

U.S. Pat. No. 6,265,185 (Muller et al.) describe yeast promoters from *Yarrowia lipolytica* for the translation elongation factor EF1-α (TEF) protein and ribosomal protein S7 that are suitable for expression cloning in yeast and heterologous expression of proteins. These promoters were improved relative to the XPR2 promoter, when tested for yeast promoter activity on growth plates (Example 9, U.S. Pat. No. 6,265, 185) and based on their activity in the pH range of 4-11.

Finally, work performed in conjunction with the Applicants herein has also resulted in the identification and isolation of the *Yarrowia lipolytica* fructose-bisphosphate aldolase promoters (e.g., FBA, FBAIN and FBAINm; see co-pending U.S. patent application Ser. No. 10/869,630, incorporated by reference herein) and the *Yarrowia lipolytica* glycerol-3-phosphate O-acyltransferase promoter (GPAT; see co-pending U.S. Patent Application No. 60/610,060, incorporated by reference herein).

Despite the utility of these known promoters, however, there is a need for new improved yeast regulatory sequences for metabolic engineering of yeast (oleaginous and non-oleaginous) and for controlling the expression of heterologous genes in yeast. Furthermore, possession of a suite of promoters that are regulatable under a variety of natural growth and induction conditions in yeast will play an important role in industrial settings, wherein it is desirable to express heterologous polypeptides in commercial quantities in said hosts for economical production of those polypeptides. Thus, it is an object of the present invention to provide such regulatory sequences that will be useful for gene expression in a variety of yeast cultures, and preferably in *Yarrowia* sp. cultures and other oleaginous yeast.

Applicants have solved the stated problem by identifying genes encoding a glyceraldehyde-3-phosphate dehydrogenase (GPD) and a phosphoglycerate mutase (GPM) from *Yarrowia lipolytica* and the regulatory sequences responsible for driving expression of these native genes. Specifically, the GPD promoter, GPDIN promoter, GPD intron, GPD enhancer and GPM promoter are each useful for expression of heterologous genes in *Yarrowia* and have improved activity with respect to the TEF promoter.

SUMMARY OF THE INVENTION

The present invention provides methods for the expression of a coding region of interest in a transformed yeast cell, using regulatory sequences of the glyceraldehyde-3-phosphate dehydrogenase (gpd) or phosphoglycerate mutase (gpm) genes. Accordingly, the present invention provides a method for the expression of a coding region of interest in a transformed yeast cell comprising:

a) providing a transformed yeast cell having a chimeric gene comprising:
  (i) a regulatory sequence of a *Yarrowia* gene selected from the group consisting of: a gpm gene and a gpd gene; and
  (ii) a coding region of interest expressible in the yeast cell;
  wherein the regulatory sequence is operably linked to the coding region of interest; and
b) growing the transformed yeast cell of step (a) under conditions whereby the chimeric gene of step (a) is expressed.

Preferred regulatory sequences of the *Yarrowia* gpd gene include the GPD promoter region; the GPDIN promoter region; and a chimeric promoter comprising the gpd intron.

Preferred regulatory sequences of the *Yarrowia* gpm gene include the GPM promoter region.

In another embodiment the invention provides a method for the production of an ω-3 or an ω-6 fatty acid comprising:

a) providing a transformed oleaginous yeast comprising a chimeric gene, comprising:
  (i) a regulatory sequence of the *Yarrowia* gpd gene or gpm gene; and
  (ii) a coding region encoding at least one enzyme of the ω-3/ω-6 fatty acid biosynthetic pathway;
  wherein the regulatory sequence and coding region are operably linked; and
(b) contacting the transformed oleaginous yeast of step (a) under conditions whereby the at least one enzyme of the ω-3/ω-6 fatty acid biosynthetic pathway is expressed and a ω-3 or ω-6 fatty acid is produced; and
(c) optionally recovering the ω-3 or ω-6 fatty acid.

Additionally the invention provides an isolated nucleic acid molecule comprising a GPD and GPDIN promoter selected from the group consisting of SEQ ID NO:23, SEQ ID NO:24, SEQ ID NO:66 and SEQ ID NO:70 as well as an isolated nucleic acid molecule comprising an intron of the *Yarrowia* gpd gene as set forth in SEQ ID NO:97.

In similar fashion the invention provides an isolated nucleic acid molecule comprising a GPM promoter selected from the group consisting of SEQ ID NO:27, SEQ ID NO:28 and SEQ ID NO:67.

In alternate embodiments, the invention provides plasmids comprising a GPM promoter region, a GPD promoter region, a GPDIN promoter region and a gpd intron.

BRIEF DESCRIPTION OF THE DRAWINGS AND SEQUENCE DESCRIPTIONS

FIGS. 1A and 1B shows an alignment of known glyceraldehyde-3-phosphate dehydrogenase (GPD) proteins from *Saccharomyces cerevisiae, Schizosaccharomyces pombe, Aspergillus oryzae, Paralichthys olivaceus, Xenopus laevis* and *Gallus gallus*, used to identify two conserved regions within the sequence alignment.

FIG. 2 shows an alignment of amino acids encoding portions of the GPD protein from *Yarrowia lipolytica, Schizosaccharomyces pombe, Gallus gallus* and *Xenopus laevis*.

FIG. 3 shows an alignment of phosphoglycerate mutase (GPM) proteins from *Yarrowia lipolytica* and *Saccharomyces cerevisiae*.

Figure 4:
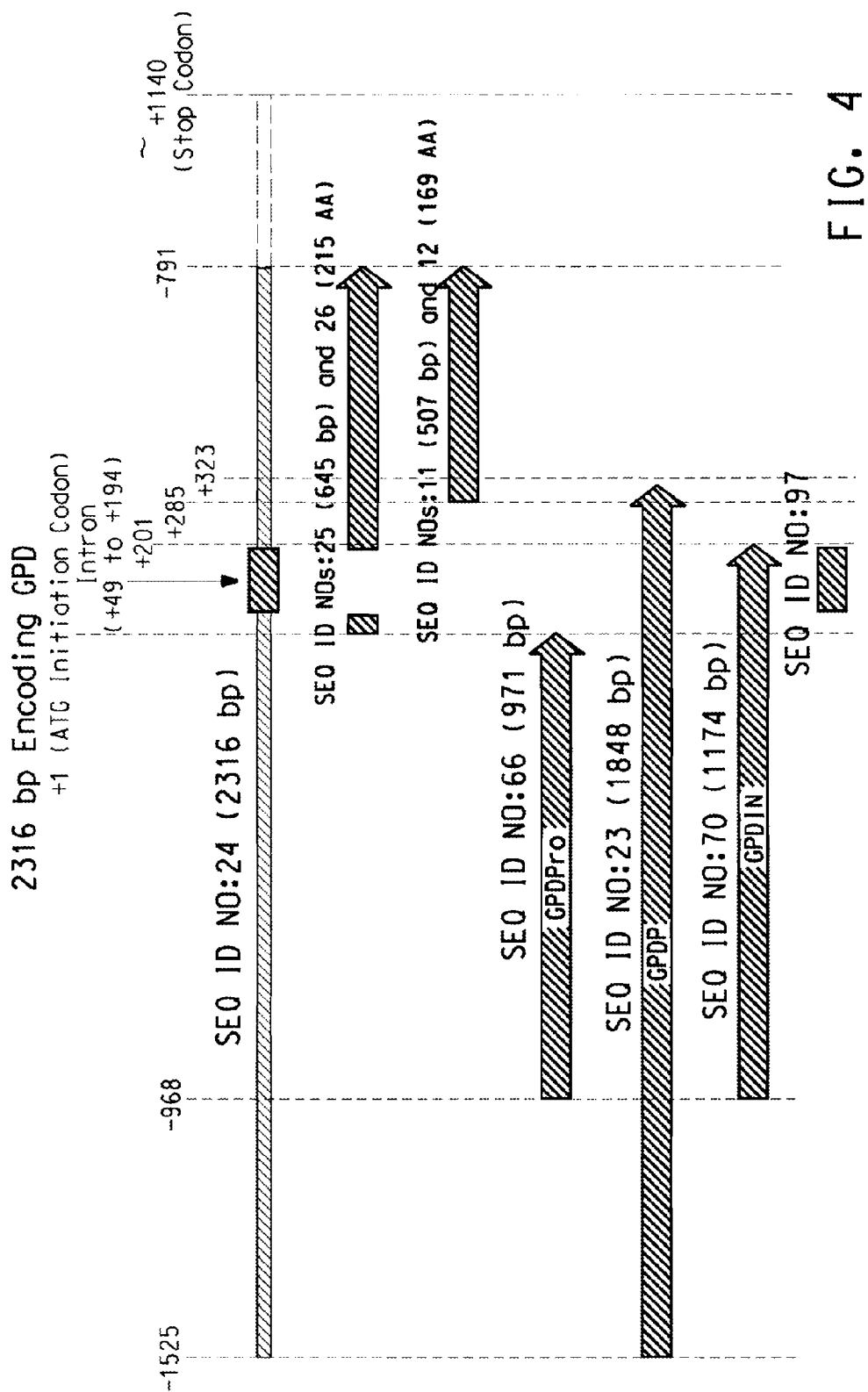

FIG. 4 graphically represents the relationship between SEQ ID NOs:11, 12, 23-26, 66, 70 and 97 each of which relates to the glyceraldehyde-3-phosphate dehydrogenase (gpd) gene in *Yarrowia lipolytica*.

Figure 5:
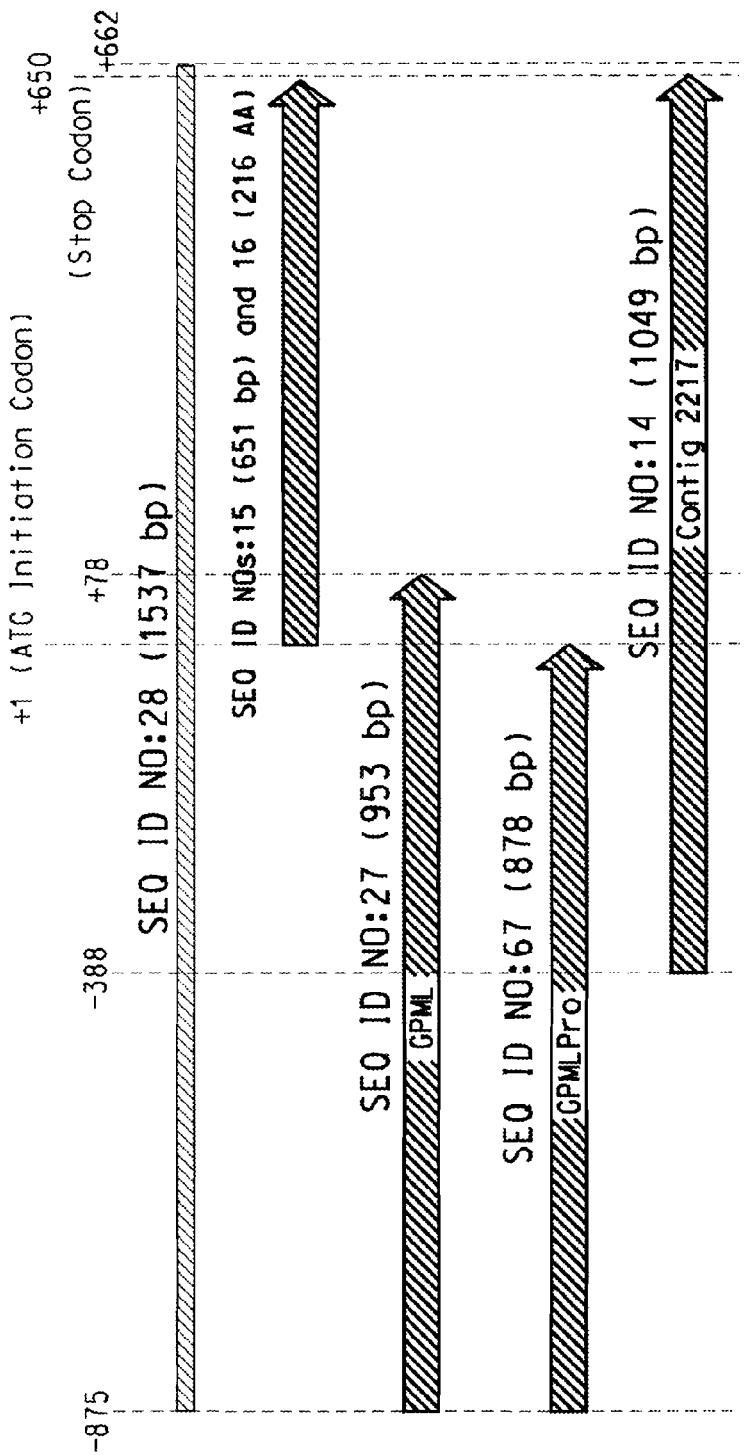

FIG. 5 graphically represents the relationship between SEQ ID NOs:14-16, 27, 28 and 67, each of which relates to the phosphoglycerate mutase (gpm) gene in *Yarrowia lipolytica*.

Figure 6:
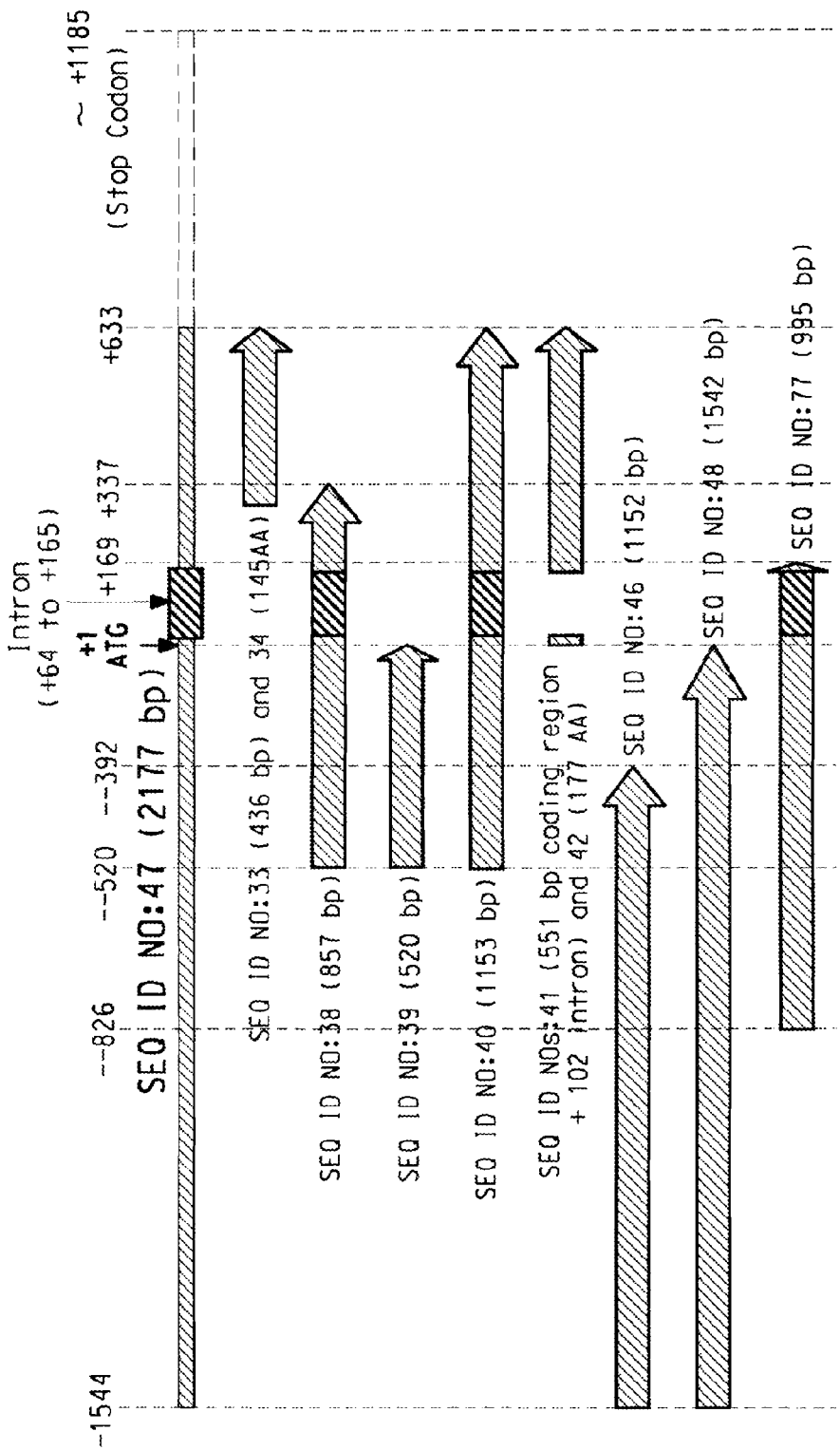

FIG. 6 graphically represents the relationship between SEQ ID NOs:33, 34, 38-42, 46-48 and 77, each of which relates to the fructose-bisphosphate aldolase (fba1) gene in *Yarrowia lipolytica*.

Figure 7A:
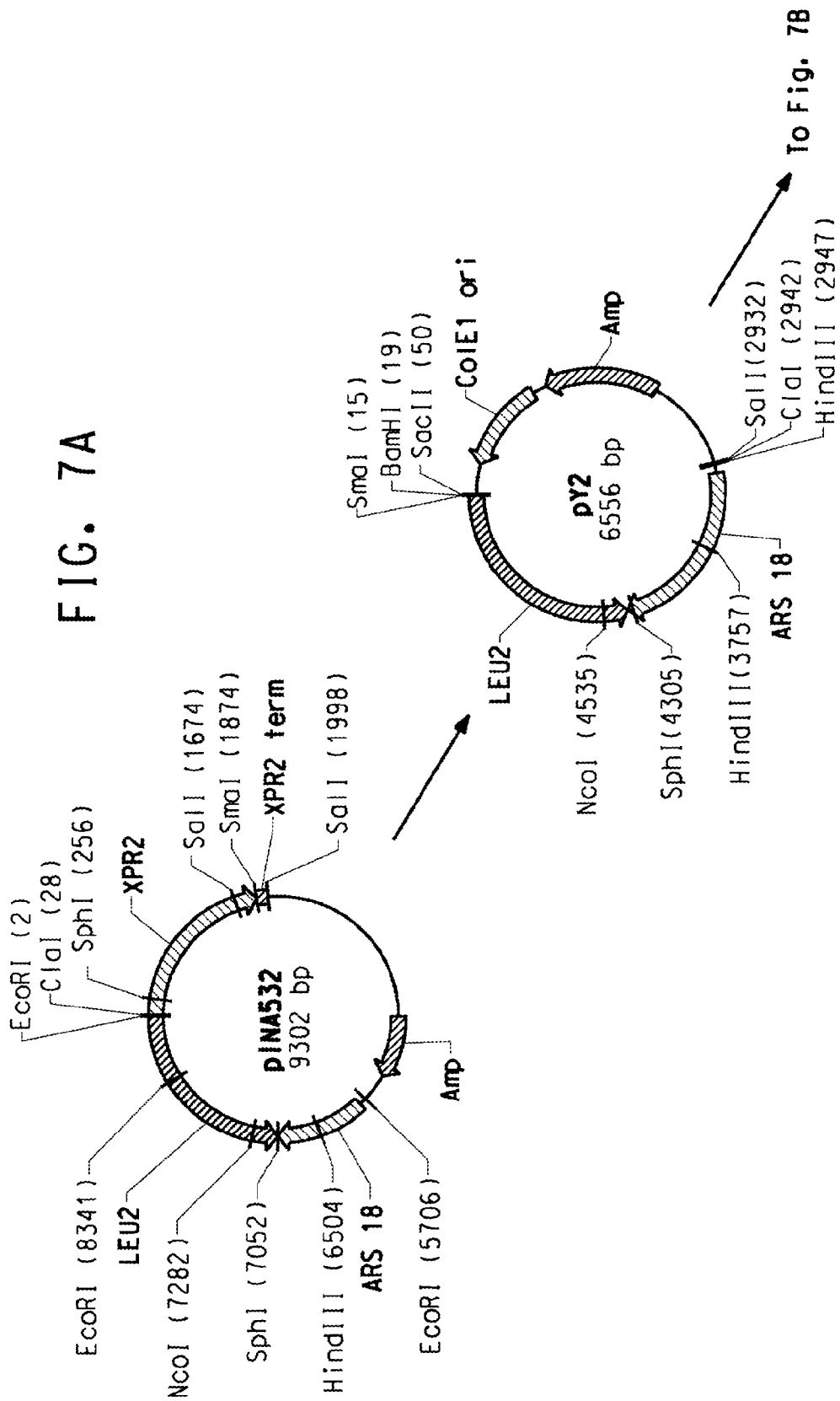
Figure 7B:
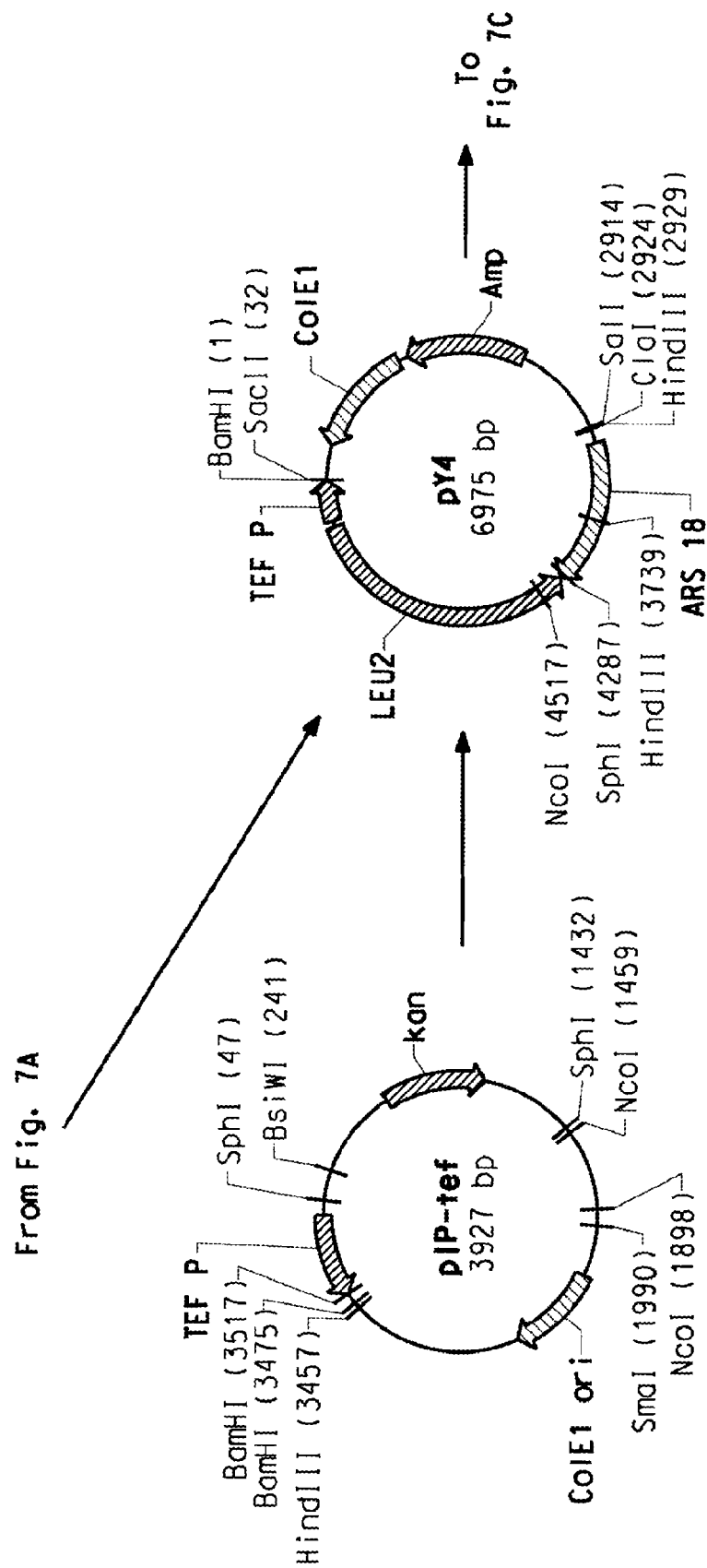

FIG. 7 illustrates the construction of plasmid vector pY5-30.

FIG. 8 provides plasmid maps for the following: (A) pYZGDG; (B) pDMW222; (C) pYZGMG; (D) pDMW212; and (E) pDMW214, respectively.

Figure 9A:
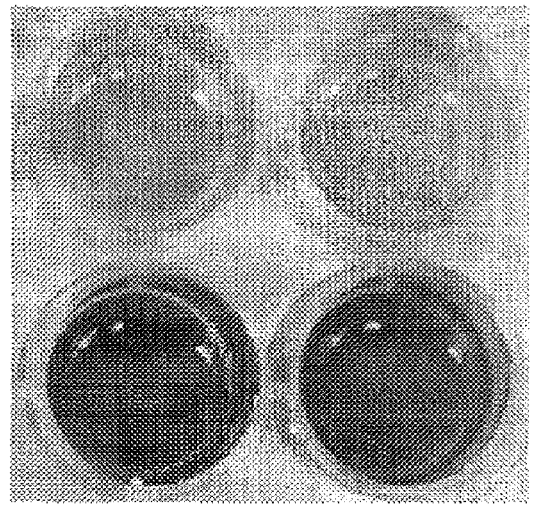
Figure 9B:
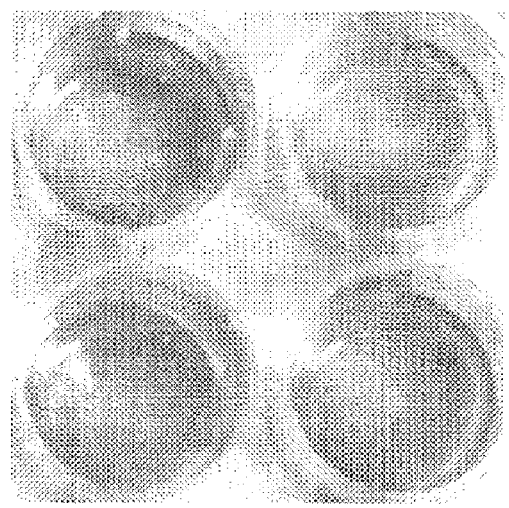
Figure 9C:
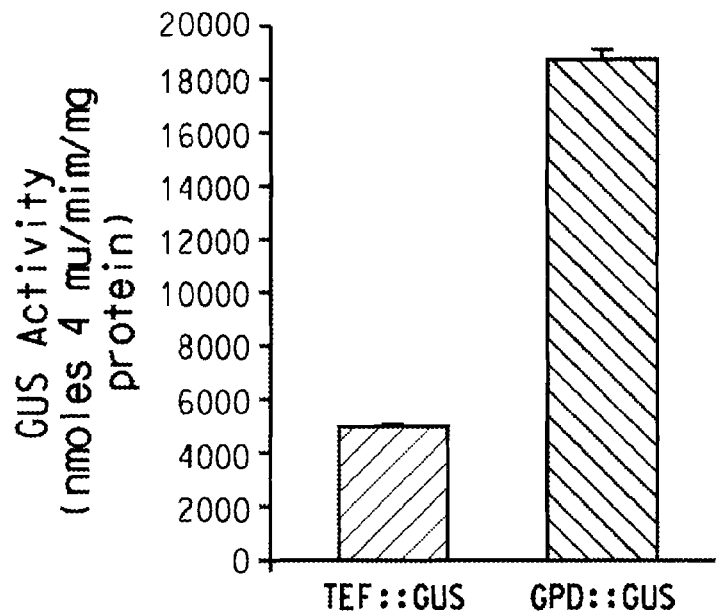
Figure 9D:
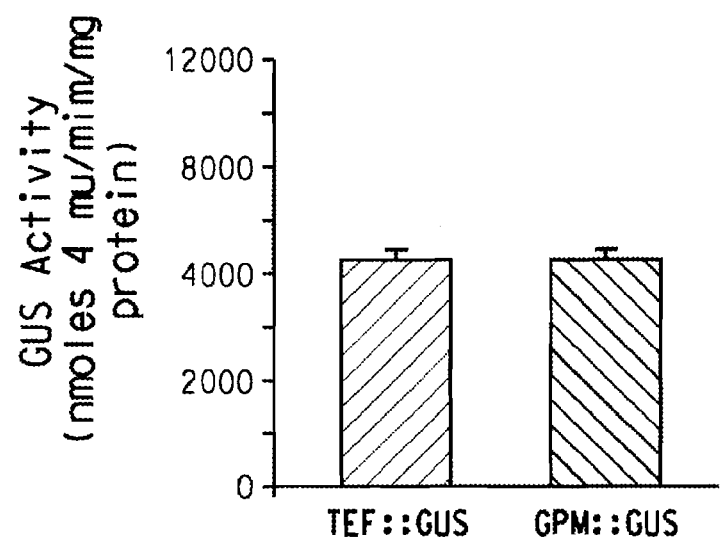

FIG. 9A is an image of a cell culture comparing the promoter activity of TEF and GPD in *Yarrowia lipolytica* as determined by histochemical staining. FIG. 9B is an image of a cell culture comparing the promoter activity of TEF and GPM in *Y. lipolytica* as determined by histochemical staining. FIG. 9C is a graph comparing the promoter activity of TEF and GPD as determined fluorometically. FIG. 9D is a graph comparing the promoter activity of TEF and GPM as determined fluorometically.

Figure 10A:
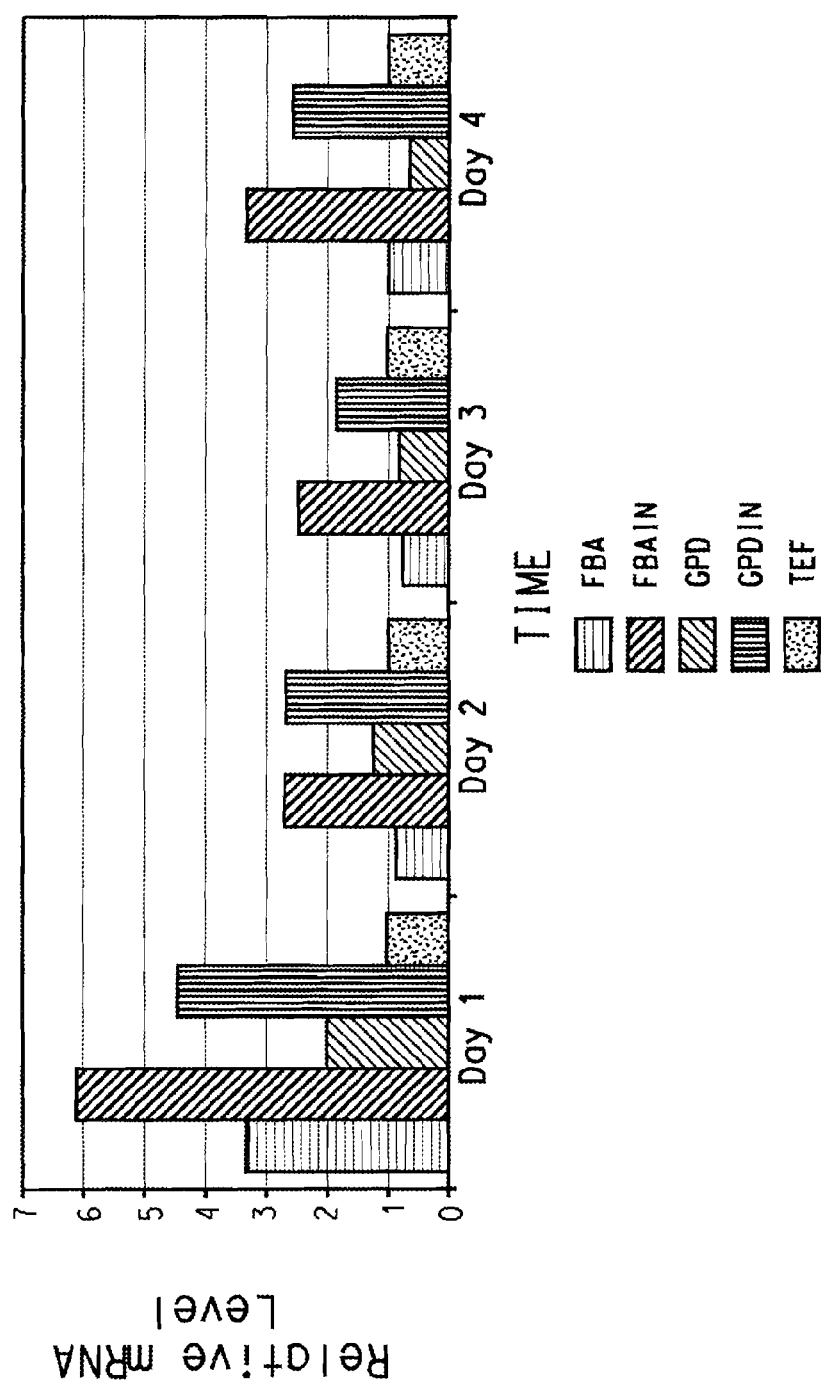
Figure 10B:
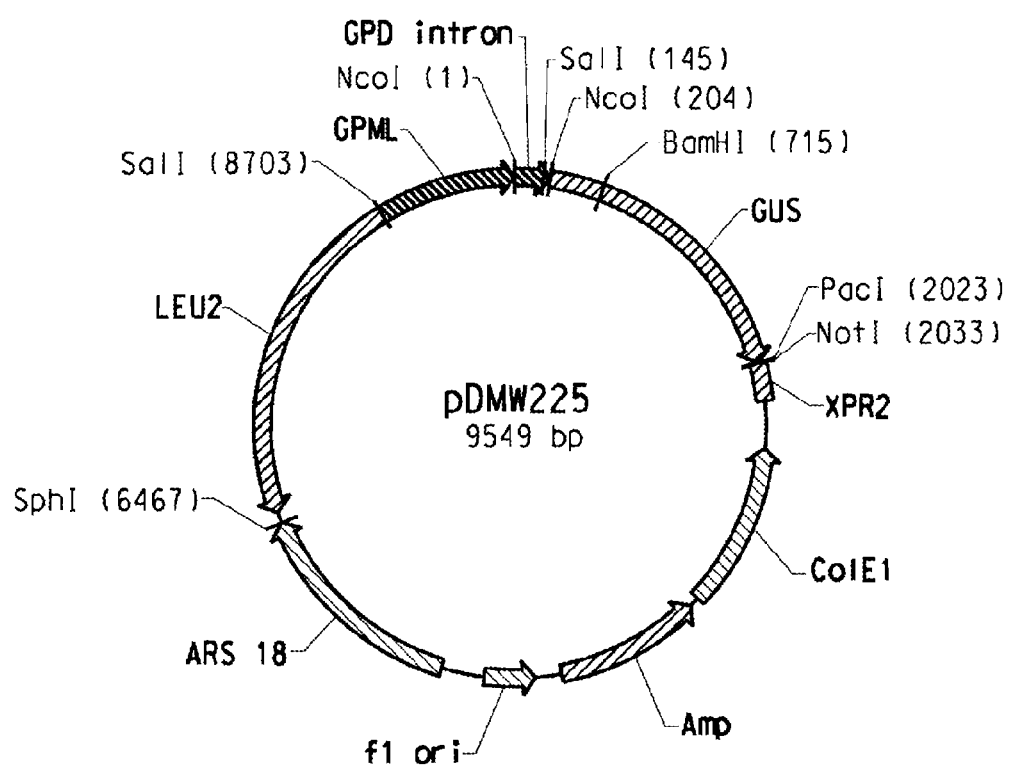
Figure 10C:
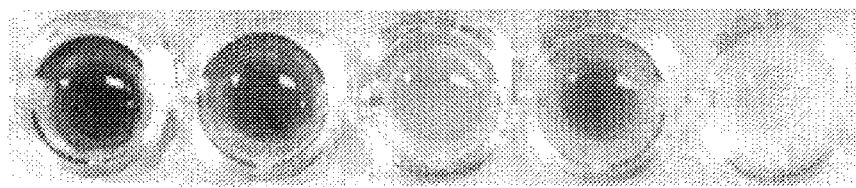

FIG. 10A graphically summarizes the results of Real Time PCR relative quantitation, wherein the GUS mRNA in different *Y. lipolytica* strains (i.e., expressing GPD::GUS, GPDIN::GUS, FBA::GUS or FBAIN::GUS chimeric genes) was quantified to the mRNA level of the *Y. lipolytica* strain expressing pY5-30 (i.e., a chimeric TEF::GUS gene). FIG. 10B provides a plasmid map for pDMW225. FIG. 10C illustrates the relative promoter activities of TEF, GPDIN, GPM, FBAIN and GPM::GPDIN in *Y. lipolytica* as determined by histochemical staining.

Figure 11:
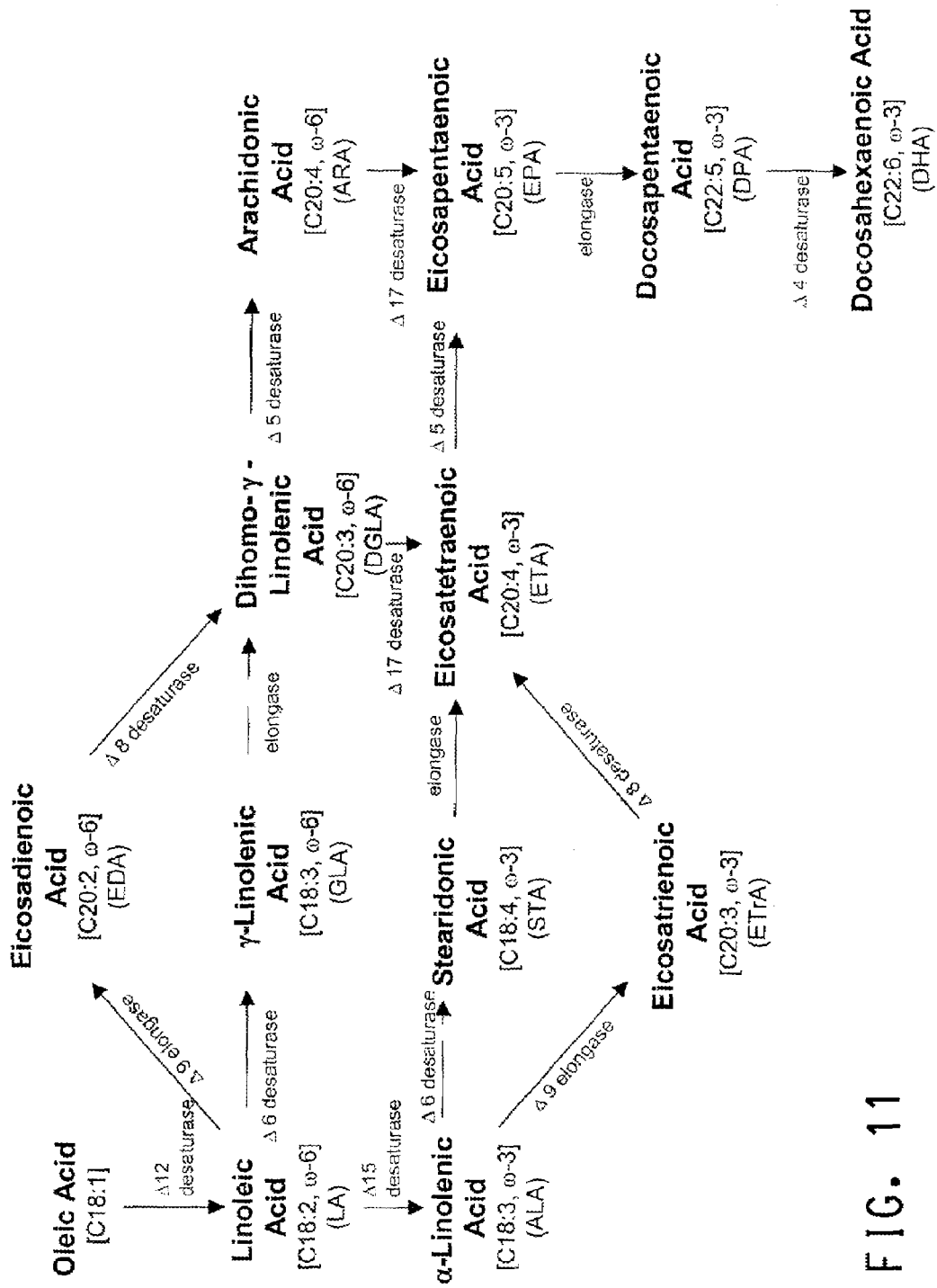

FIG. 11 illustrates the ω-3/ω-6 fatty acid biosynthetic pathway.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-6, 11-16, 23-28, 33, 34, 38-42, 46-48, 51, 66, 67, 70, 74, 77, 84, 93, 94 and 97 correspond to ORFs (i.e., encoding genes or proteins), promoters and terminators, as identified in Table 1.

TABLE 1

Summary Of Nucleotide And Protein SEQ ID Numbers

| Description | Nucleotide SEQ ID NO | Protein SEQ ID NO |
|---|---|---|
| *Saccharomyces cerevisiae* GPD (GenBank Accession No. CAA24607) | — | 1 (332 AA) |
| *Schizosaccharomyces pombe* GPD (GenBank Accession No. NP_595236) | — | 2 (335 AA) |
| *Aspergillus oryzae* GPD (GenBank Accession No. AAK08065) | — | 3 (338 AA) |
| *Paralichthys olivaceus* GPD (GenBank Accession No. BAA88638) | — | 4 (333 AA) |
| *Xenopus laevis* GPD (GenBank Accession No. P51469) | — | 5 (333 AA) |
| *Gallus gallus* GPD (GenBank Accession No. DECHG3) | — | 6 (333 AA) |
| *Yarrowia lipolytica* gpd gene-internal portion | 11 (507 bp) | 12 (169 AA) |
| *Yarrowia lipolytica* gpd gene-upstream and 5' portion of coding sequence ("GPDP") | 23 (1848 bp) | — |
| *Yarrowia lipolytica* gpd gene-contig comprising GPD coding sequence (−1525 bp to +791 bp region) | 24 (2316 bp) | — |
| *Yarrowia lipolytica* gpd gene-partial cDNA sequence | 25 (645 bp) | 26 (215 AA) |
| *Yarrowia lipolytica* GPD promoter ("GPDPro"; −968 bp to +3 bp) | 66 (971 bp) | — |
| *Yarrowia lipolytica* GPDIN promoter | 70 (1174 bp) | — |
| *Yarrowia lipolytica* gpd intron | 97 (146 bp) | — |
| *Saccharomyces cerevisiae* GPM (GenBank Accession No. NP_012770) | — | 13 (245 AA) |
| *Yarrowia lipolytica* GPM-contig 2217, comprising GPM coding sequence | 14 (1049 bp) | — |
| *Yarrowia lipolytica* gpm gene-coding sequence | 15 (651 bp) | 16 (216 AA) |
| *Yarrowia lipolytica* gpm gene-upstream and 5' portion of coding sequence ("GPML"; −875 bp to +78 bp) | 27 (953 bp) | — |
| *Yarrowia lipolytica* gpm gene-contig comprising GPM coding sequence (−875 bp to +662 bp) | 28 (1537 bp) | — |
| *Yarrowia lipolytica* GPM promoter ("GPMLPro"; −875 bp to +3 bp) | 67 (878 bp) | — |
| *Yarrowia lipolytica* fba1 gene-internal portion | 33 (436 bp) | 34 (145 AA) |
| *Yarrowia lipolytica* fba1 gene-1st round genome walking product | 38 (857 bp) | — |
| *Yarrowia lipolytica* fba1 gene-5'-upstream portion of 1st round genome walking product | 39 (520 bp) | — |
| *Yarrowia lipolytica* fba1 gene-contig assembly of SEQ ID NOs:33 and 38 | 40 (1153 bp) | — |
| *Yarrowia lipolytica* fba1 gene | 41 (531 bp) | 42 (177 AA) |
| *Yarrowia lipolytica* fba1 gene-2nd round genome walking product | 46 (1152 bp) | — |
| *Yarrowia lipolytica* fba1 gene-contig assembly of SEQ ID NOs:33, 38 and 46 | 47 (2177 bp) | — |
| *Yarrowia lipolytica* fba1 gene-5' upstream portion | 48 (1542 bp) | — |
| *Yarrowia lipolytica* FBA promoter | 74 (1001 bp) | — |
| *Yarrowia lipolytica* FBAIN promoter | 77 (995 bp) | — |
| *Yarrowia lipolytica* TEF promoter | 51 (436 bp) | — |
| chimeric *Yarrowia lipolytica* GPM::gpd intron (GPM::GPDIN) promoter | 84 (1052 bp) | — |
| *Fusarium moniliforme* strain M-8114 Δ15 desaturase | 93 (1209 bp) | 94 (402 AA) |

SEQ ID NOs:7 and 8 correspond to conserved amino acid regions of the GPD protein, while SEQ ID NOs:9 and 10 are the corresponding degenerate primers YL193 and YL194, respectively, used for isolating an internal portion of the *Yarrowia lipolytica* gpd gene.

SEQ ID NOs:17-22 correspond to primers YL206, YL196, YL207, YL197, YL208 and YL198, respectively, used for genome walking.

SEQ ID NOs:29 and 30 correspond to conserved amino acid regions of the FBA1 protein, while SEQ ID NOs:31 and 32 are the corresponding degenerate primers YL214 and YL216, respectively, used for isolating a portion of coding region of the *Yarrowia lipolytica* fba1 gene.

SEQ ID NOs:35-37 and 4345 are the oligonucleotides YL217, YL218, YL219, ODMW315, ODMW316 and ODMW317, respectively, used for genome-walking.

SEQ ID NOs:49 and 50 correspond to primers YL33 and YL34, respectively, used for amplifying the reporter gene GUS.

SEQ ID NOs:52 and 53 correspond to primers TEF5' and TEF3', respectively, used to isolate the TEF promoter.

SEQ ID NOs:54 and 55 correspond to primers XPR5' and XPR3', respectively, used to isolate the XPR2 transcriptional terminator.

SEQ ID NOs:56-63 correspond to primers YL1, YL2, YL3, YL4, YL23, YL24, YL9 and YL10, respectively, used for site-directed mutagenesis during construction of the pY5-10 plasmid.

SEQ ID NO:64 corresponds to plasmid pY5-30.

SEQ ID NO:65 is the consensus sequence around the translation initiation codon in *Yarrowia lipolytica*.

SEQ ID NOs:68 and 69 correspond to primers YL211 and YL212, respectively, used to amplify the putative GPD promoter.

SEQ ID NO:71 corresponds to primer YL377, used to amplify the putative GPDIN promoter.

SEQ ID NOs:72 and 73 correspond to primers YL203 and YL204, respectively, used to amplify the putative GPM promoter.

SEQ ID NOs:75 and 76 are the oligonucleotides ODMW314 and YL341, respectively, used to amplify the FBA promoter region.

SEQ ID NOs:78 and 79 are the oligonucleotides ODMW320 and ODMW341, respectively, used to amplify the FBAIN promoter region.

SEQ ID NOs:80-83 are the oligonucleotides YL-URA-16F, YL-URA-78R, GUS-767F and GUS-891 R, respectively, used for Real Time PCR analysis.

SEQ ID NOs:85-90 correspond to primers YL5, YL6, YL7, YL8, YL61 and YL62, respectively, used for construction of plasmid pY5-13.

SEQ ID NOs:91 and 92 correspond to primers GPDsense and GPDantisense, respectively, used to amplify GPDPro.

SEQ ID NOs:95 and 96 correspond to primers P192 and P193, respectively, used to amplify the *F. moniliforme* Δ15 desaturase.

DETAILED DESCRIPTION OF THE INVENTION

In accordance with the subject invention, Applicants describe the isolation and characterization of a gene encoding glyceraldehyde-3-phosphate dehydrogenase (GPD) and a gene encoding phosphoglycerate mutase (GPM) from an oleaginous yeast, *Yarrowia lipolytica*, as well as the regulatory sequences associated with these gene. The GPD promoter region ("GPD"), the GPD promoter region plus the 5' portion of the coding sequence comprising an intron ("GPDIN"), the GPM promoter region ("GPM"), the gpd intron and an enhancer within the gpd intron are all useful for genetic engineering in *Y. lipolytica* and other yeast for the production of heterologous polypeptides.

Preferred heterologous polypeptides of the present invention are those that are involved in the synthesis of microbial oils and particularly polyunsaturated fatty acids (PUFAs). PUFAs, or derivatives thereof, made by the methodology disclosed herein can be used in many applications. For example, the PUFAs can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products, and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Thus, the present invention advances the art by providing methods for the expression of a coding region of interest in a transformed yeast comprising: a) providing a transformed yeast cell having a chimeric gene comprising (i) a regulatory sequence of a glyceraldehyde-3-phosphate dehydrogenase (gpd) gene or phosphoglycerate mutase (gpm) gene, wherein the regulatory sequence is a GPD promoter region, a GPD promoter region plus a portion of 5' coding region comprising an intron of a gpd gene (GPDIN), a GPM promoter region, or a chimeric promoter comprising the gpd intron or gpd enhancer therein; and (ii) a coding region of interest expressible in the host cell, wherein the regulatory sequence is operably linked to the coding region of interest; and b) growing the transformed yeast cell of step (a) in the presence of a fermentable carbon source, wherein the chimeric gene is expressed and the expression product is optionally isolated from the cultivation medium. In preferred embodiments, the regulatory sequence comprises all or a portion of a sequence selected from the group consisting of SEQ ID NOs: 23, 24, 27, 28, 66, 67, 70 and 97.

DEFINITIONS

In this disclosure, a number of terms and abbreviations are used. The following definitions are provided.

"Glyceraldehyde-3-phosphate dehydrogenase" is abbreviated GPD.

"Phosphoglycerate mutase" is abbreviated GPM.

"Fructose-bisphosphate aldolase" is abbreviated FBA1.

"Open reading frame" is abbreviated ORF.

"Polymerase chain reaction" is abbreviated PCR.

"Polyunsaturated fatty acid(s)" is abbreviated PUFA(s).

The term "oleaginous" refers to those organisms that tend to store their energy source in the form of lipid (Weete, In: Fungal Lipid Biochemistry, $2^{nd}$ Ed., Plenum, 1980). These include oilseed plants (e.g., soybean, corn, safflower, sunflower, canola, rapeseed, flax, maize and primrose) and microorganisms (e.g., *Thraustochytrium* sp., *Schizochytrium* sp., *Mortierella* sp. and certain oleaginous yeast).

The term "oleaginous yeast" refers to those microorganisms classified as yeasts that can make oil. Generally, the cellular oil or triacylglycerol content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)). It is not uncommon for oleaginous microorganisms to accumulate in excess of about 25% of their dry cell weight as oil. Examples of oleaginous yeast include (but are no means limited to) the following genera: *Yarrowia, Candida, Rhodotorula, Rhodosporidium, Cryptococcus, Trichosporon* and *Lipomyces*.

The term "fermentable carbon source" will refer to a carbon source that a microorganism will metabolize to derive energy. Typical carbon sources for use in the present invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

The term "GPD" refers to a glyceraldehyde-3-phosphate dehydrogenase enzyme (E.C. 1.2.1.12) encoded by the gpd gene and which converts D-glyceraldehyde 3-phosphate to 3-phospho-D-glyceroyl phosphate during glycolysis. The partial coding region of a representative gpd gene isolated from *Yarrowia lipolytica* is provided as SEQ ID NOs:25 and 26; specifically, the sequence lacks ~115 amino acids that encode the C-terminus of the gene (based on alignment with other known gpd sequences). The *Yarrowia lipolytica* GPD protein sequence was also published as part of the public *Y. lipolytica* protein database of the "Yeast project Genolevures" (sponsored by the Center for Bioinformatics, LaBRI, bâtiment Δ30, Universite Bordeaux 1, 351, cours de la Libération, 33405 Talence Cedex, France) (see also Dujon, B. et al., *Nature* 430 (6995):35-44 (2004)). The GPD sequence disclosed therein was identified as ORF YALI-CDS 4019.1 and corresponded to GenBank Accession No. CAG81816.

The term "GPD promoter" or "GPD promoter region" refers to the 5' upstream untranslated region in front of the 'ATG' translation initiation codon of gpd and that is necessary for expression. An example of a suitable GPD promoter region is provided as SEQ ID NO:66, but this is not intended to be limiting in nature. One skilled in the art will recognize that since the exact boundaries of the GPD promoter sequence have not been completely defined, DNA fragments of increased or diminished length may have identical promoter activity.

The term "GPDIN promoter" or "GPDIN promoter region" refers to the 5' upstream untranslated region in front of the 'ATG' translation initiation codon of gpd and that is necessary for expression, plus a portion of 5' coding region comprising an intron of the gpd gene. An example of a suitable GPDIN promoter region is provided as SEQ ID NO:70, but this is not intended to be limiting in nature. Again, one will recognize that since the exact boundaries of the GPDIN promoter sequence have not been completely defined, DNA fragments of increased or diminished length may have identical promoter activity.

The term "gpd intron" or "intron of the gpd gene" refers to the intron as defined by SEQ ID NO:97.

The term "GPM" refers to a phosphoglycerate mutase enzyme (EC 5.4.2.1) encoded by the gpm gene and which is responsible for the interconversion of 3-phosphoglycerate and 2-phosphoglycerate during glycolysis. A respresentative gpm gene from *Saccharomyces cerevisiae* is GenBank Accession No. NP_012770 (SEQ ID NO:13); a gpm gene isolated from *Yarrowia lipolytica* is provided as SEQ ID NO:15. The *Yarrowia lipolytica* GPM protein sequence was also published as part of the public *Y. lipolytica* protein database of the "Yeast project Genolevures" (supra), identified therein as ORF YALI-CDS4938.1, encoding 247 amino acids, and corresponding to GenBank Accession No. CAG82653.

The term "GPM promoter" or "GPM promoter region" refers to the 5' upstream untranslated region in front of the 'ATG' translation initiation codon of gpm and that is necessary for expression. Examples of suitable GPM promoter regions are provided as SEQ ID NOs:27 and 67, but these are not intended to be limiting in nature. Again, one will recognize that since the exact boundaries of the GPM promoter sequence have not been completely defined, DNA fragments of increased or diminished length may have identical promoter activity.

The term "FBA1" refers to a fructose-bisphosphate aldolase enzyme (E.C. 4.1.2.13) encoded by the fba1 gene and which converts D-fructose 1,6-bisphosphate into glycerone phosphate and D-glyceraldehyde 3-phosphate. The term "FBA promoter" or "FBA promoter region" refers to the 5' upstream untranslated region in front of the 'ATG' translation initiation codon of fba1 and that is necessary for expression. One example of a suitable FBA promoter region is provided as SEQ ID NO:74, but this is not intended to be limiting in nature (see co-pending U.S. patent application Ser. No. 10/987,548).

The term "FBAIN promoter" or "FBAIN promoter region" refers to the 5' upstream untranslated region in front of the 'ATG' translation initiation codon of fba1 and that is necessary for expression, plus a portion of 5' coding region comprising an intron of the fba1 gene. An example of a suitable FBAIN promoter region is provided as SEQ ID NO:77, but this is not intended to be limiting in nature (see co-pending U.S. patent application Ser. No. 10/987,548).

The term "promoter activity" will refer to an assessment of the transcriptional efficiency of a promoter. This may, for instance, be determined directly by measurement of the amount of mRNA transcription from the promoter (e.g., by Northern blotting or primer extension methods) or indirectly by measuring the amount of gene product expressed from the promoter.

As used herein, an "isolated nucleic acid molecule" and "isolated nucleic acid fragment" are used interchangeably and mean a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual, 2nd* ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence.

The instant specification teaches partial or complete amino acid and nucleotide sequences encoding one or more particular microbial proteins and regulatory sequences. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "oligonucleotide" refers to a nucleic acid, generally of at least 18 nucleotides, that is hybridizable to a genomic DNA molecule, a cDNA molecule, or an mRNA molecule. In one embodiment, a labeled oligonucleotide can be used as a "probe" to detect the presence of a nucleic acid according to the invention. Thus, the term "probe" refers to a single-stranded nucleic acid molecule that can base pair with a complementary single-stranded target nucleic acid to form a double-stranded molecule. The term "label" will refer to any conventional molecule which can be readily attached to mRNA or DNA and which can produce a detectable signal, the intensity of which indicates the relative amount of hybridization of the labeled probe to the DNA fragment.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.* 5:151-153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid molecules (isolated polynucleotides of the present invention) encode polypeptides that are at least about 70% identical, preferably at least about 75% identical, and more preferably at least about 80% identical to the amino acid sequences reported herein. Preferred nucleic acid molecules encode amino acid sequences that are about 85% identical to the amino acid sequences reported herein. More preferred nucleic acid molecules encode amino acid sequences that are at least about 90% identical to the amino acid sequences reported herein. Most preferred are nucleic acid molecules that encode amino acid sequences that are at least about 95% identical to the amino acid sequences reported herein. Suitable nucleic acid molecules not only have the above homologies but typically encode a polypeptide having at least 50 amino acids, preferably at least 100 amino acids, more preferably at least 150 amino acids, still more preferably at least 200 amino acids, and most preferably at least 250 amino acids.

Likewise, suitable regulatory sequences (isolated polynucleotides of the present invention) are at least about 70% identical, preferably at least about 75% identical, and more preferably at least about 80% identical to the nucleotide sequences reported herein. Preferred nucleic acid molecules are about 85% identical to the nucleotide sequences reported herein, more preferred nucleic acid molecules are at least about 90% identical, and most preferred are nucleic acid molecules at least about 95% identical to the nucleotide sequences reported herein. Suitable regulatory sequences not only have the above homologies but typically are at least 50 nucleotides in length, more preferably at least 100 nucleotides in length, more preferably at least 250 nucleotides in length, and most preferably at least 500 nucleotides in length.

"Codon degeneracy" refers to the nature in the genetic code permitting variation of the nucleotide sequence without affecting the amino acid sequence of an encoded polypeptide. Accordingly, the instant invention relates to any nucleic acid molecule that encodes all or a substantial portion of the amino acid sequence encoding the instant microbial polypeptides as set forth in SEQ ID NOs:16 and 26. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Coding sequence" refers to a DNA sequence that codes for a specific amino acid sequence.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes of the present invention will typically comprise a regulatory sequence of the gpd or gpm gene operably linked to a coding region of interest. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Regulatory sequences" refer to transcriptional and translational "control" nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, enhancers, initiation control regions, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. The term "promoter region" as used herein means that region of a nucleic acid molecule that contains a functional promoter. The promoter region may comprise extraneous nucleic acid elements or fragments; however, it does contain all of the promoter in question. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "mutant promoter" is defined herein as a promoter having a nucleotide sequence comprising a substitution, deletion, and/or insertion of one or more nucleotides relative to the parent promoter, wherein the mutant promoter has more or less promoter activity than the corresponding parent promoter. The term "mutant promoter" will encompass natural variants and in vitro generated variants obtained using methods well known in the art (e.g., classical mutagenesis, site-directed mutagenesis and "DNA shuffling").

The term "introns" refers to sequences of non-coding DNA found in gene sequences (either in the coding region, 5' non-coding region, or 3' non-coding region) in most eukaryotes. Their full function is not known; however, some enhancers are located in introns (Giacopelli F. et al., Gene Expr. 11: 95-104 (2003)). These intron sequences are transcribed, but removed from within the pre-mRNA transcript before the mRNA is translated into a protein. This process of intron removal occurs by self-splicing of the sequences (exons) on either side of the intron.

The term "enhancer" refers to a cis-regulatory sequence that can elevate levels of transcription from an adjacent eukaryotic promoter, thereby increasing transcription of the gene. Enhancers can act on promoters over many tens of kilobases of DNA and can be 5' or 3' to the promoter they regulate. Enhancers can also be located within introns.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid molecule so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a coding sequence. Expression may also refer to translation of mRNA into a polypeptide.

The term "altered biological activity" will refer to an activity, associated with a protein encoded by a nucleotide sequence which can be measured by an assay method, where that activity is either greater than or less than the activity associated with the native sequence. "Enhanced biological activity" refers to an altered activity that is greater than that associated with the native sequence. "Diminished biological activity" is an altered activity that is less than that associated with the native sequence.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid molecules are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); and 4.) the FASTA program incorporating the Smith-Waterman algorithm (W. R. Pearson, *Comput. Methods Genome Res.*, [Proc. Int. Symp.] (1994), Meeting Date 1992, 111-20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Identification of the gpd and gpm Genes in *Yarrowia lipolytica*

The present invention identifies the partial sequence of a glyceraldehyde-3-phosphate dehydrogenase (gpd) gene (wherein ~115 amino acids of the C-terminus of the encoded protein are not disclosed herein) and the complete sequence of the phosphoglycerate mutase (gpm) gene contained within the *Yarrowia lipolytica* genome.

Comparison of the partial gpd nucleotide base and deduced amino acid sequences (SEQ ID NOs:25 and 26) to public databases reveals that the most similar known sequences are about 81% identical to the amino acid sequence of gpd reported herein over a length of 215 amino acids using a Smith-Waterman alignment algorithm (W. R. Pearson, supra). Preferred amino acid fragments are at least about 70%-80% identical to the sequences herein, where those sequences that are 85%-90% identical are particularly suitable and those sequences that are about 95% identical are most preferred. Similarly, preferred gpd encoding nucleic acid sequences corresponding to the instant ORF are those encoding active proteins and which are at least about 70%-80% identical to the nucleic acid sequences of gpd reported herein, where those sequences that are 85%-90% identical are particularly suitable and those sequences that are about 95% identical are most preferred.

Comparison of the gpm nucleotide base and deduced amino acid sequences (SEQ ID NOs:15 and 16) to public databases reveals that the most similar known sequences are about 71% identical to the amino acid sequence of gpm reported herein over a length of 216 amino acids using a Smith-Waterman alignment algorithm (W. R. Pearson, supra). Preferred amino acid fragments are at least about 70%-80% identical to the sequences herein, where those sequences that are 85%-90% identical are particularly suitable and those sequences that are about 95% identical are most preferred. Similarly, preferred gpm encoding nucleic acid sequences corresponding to the instant ORF are those encoding active proteins and which are at least about 70%-80% identical to the nucleic acid sequences of gpm reported herein, where those sequences that are 85%-90% identical are particularly suitable and those sequences that are about 95% identical are most preferred.

Identification of Regulatory Sequences of the gpd and gpm Genes in *Yarrowia lipolytica* and Relative Quantitation of their Activity The present invention also identifies putative promoter regions, an intron and an enhancer that naturally regulate the expression of the gpd gene and a putative promoter region that naturally regulates the expression of the gpm gene in *Yarrowia lipolytica*. These regulatory sequences have been identified as useful for driving expression of any suitable coding region of interest in a transformed yeast cell.

In the context of the presention invention, a promoter useful in an oleaginous yeast should meet the following criteria:

1.) Strength. A strong yeast promoter is a necessary premise for a high expression level, and the low copy number of the ars18 (Fournier, P. et al. *Yeast* 7:25-36 (1991)) based expression vectors or chimeric genes integrated into the genome makes this demand even more imporant when *Y. lipolytica* is used as the host organism.
2.) Activity in a medium suitable for expression of the coding region of interest, and high enzymatic activity of that coding region of interest.
3.) pH Tolerance. If the coding region of interest is known to be produced only in e.g., an acidic environment, then the promoter operably linked to said coding region of interest must function at the appropriate pH. pH tolerance is of course limited by the tolerance of the host organism.
4.) Inducibility. A tightly regulated yeast promoter makes it possible to separate the growth stage from the expression stage, thereby enabling expression of products that are known to inhibit cell growth.
5.) Activity in the stationary phase of growth in oleaginous yeast hosts, to thereby enable accumulation of proteins encoded by select coding regions of interest (e.g., PUFAs).

Additionally, it is preferable for novel yeast promoters to possess differences in activity with respect to the known *Yarrowia lipolytica* TEF (U.S. Pat. No. 6,265,185), XPR2 (U.S. Pat. No. 4,937,189; EP220864; EP832258), FBA (co-pending U.S. patent application Ser. No. 10/987,548), FBAIN (co-pending U.S. patent application Ser. No. 10/987, 548), FBAINm (co-pending U.S. patent application Ser. No. 10/987,548) and GPAT (co-pending U.S. Patent Application No. 60/610,060) promoters (wherein each patent and application above is incorporated by reference herein in its entirety). Comparative studies of the known TEF, FBA and FBAIN promoters and the GPD, GPDIN and GPM promoters of the instant invention are provided in Examples 9 and 10. It is shown that the yeast promoters of the invention have improved activity compared to the TEF promoter. The promoter region (GPD) of the instant gpd gene, and the promoter region plus the 5' portion of coding region comprising an intron (GPDIN) of the instant gpd gene, or portions of GPD or GPDIN, are contained within several nucleic acid molecules (specifically, SEQ ID NOs: 23, 24, 66, 70 and 97).

In one embodiment, the GPD promoter will comprise nucleotides −500 to +1 of SEQ ID NO:66 (wherein the 'A' position of the 'ATG' translation initiation codon is designated as +1), thereby permitting relatively strong promoter activity; in alternate embodiments, the −100 to +1 region of SEQ ID NO:66 should be sufficient for basal activity of the promoter. The promoter regions of the invention may also comprise additional nucleotides to those specified above. For example, the GPDIN promoter (i.e., SEQ ID NO:70) includes the intron of the instant gpd gene, which is located at position +49 to +194 within the gpd gene (i.e., SEQ ID NO:97).

The GPM promoter region of the instant invention is contained in several nucleic acid molecules disclosed herein, including SEQ ID NOs:27, 28 and 67. In one embodiment, the GPM promoter will comprise nucleotides −500 to +1 of SEQ ID NO:67 (wherein the 'A' position of the 'ATG' translation initiation codon is designated as +1), thereby permitting relatively strong promoter activity; alternatively, the −100 to +1 region of SEQ ID NO:67 should be sufficient for basal activity of the promoter.

On the basis of the work presented herein and the knowledge of one of skill in the art, it will be obvious that various promoter sequences of the invention may be constructed on the basis of the DNA sequence presented as SEQ ID NO:23 or SEQ ID NO:27 (e.g., SEQ ID NOs:66 and 67 are subsequences thereof, respectively). It should be recognized that promoter fragments of various diminishing lengths may have identical promoter activity, since the exact boundaries of the regulatory sequences have not been completely defined.

In alternate embodiments, it was demonstrated herein that the gpd intron (i.e., SEQ ID NO:97) or the enhancer within the intron of the gpd gene may be used to enhance the activity of a promoter. Specifically, GPDIN demonstrated enhanced expression of a coding region relative to the GPD promoter (Example 10). Upon further analysis, it was determined herein that the gpd intron comprises an enhancer that is useful for increasing the transcription from an adjacent eukaryotic promoter, wherein the adjacent promoter can be the native GPD or GPDIN promoter or a chimeric promoter (e.g., the GPM promoter demonstrated increased activity when used in conjunction with the gpd intron as a chimeric promoter; see Example 11).

Although it may be useful to indirectly quantitate promoter activity based on reporter gene expression (i.e., the *E. coli* gene encoding β-glucuronidase (GUS)), it may sometimes be useful to quantify promoter activity using more quantitative means. One suitable method is the use of real-time PCR (for a general review of real-time PCR applications, see Ginzinger, D. J., *Experimental Hematology*, 30:503-512 (2002)). Real-time PCR is based on the detection and quantitation of a fluorescent reporter. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. There are two general methods for the quantitative detection of the amplicon: (1) use of fluorescent probes; or (2) use of DNA-binding agents (e.g., SYBR-green I, ethidium bromide). For relative gene expression comparisons, it is necessary to use an endogenous control as an internal reference (e.g., a chromosomally encoded 16S rRNA gene), thereby allowing one to normalize for differences in the amount of total DNA added to each real-time PCR reaction. Specific methods for real-time PCR are well documented in the art. See, for example, the Real Time PCR Special Issue (*Methods*, 25(4):383-481 (2001)).

Following a real-time PCR reaction, the recorded fluorescence intensity is used to quantitate the amount of template by use of: 1.) an absolute standard method (wherein a known amount of standard such as in vitro translated RNA (cRNA) is used); 2.) a relative standard method (wherein known amounts of the target nucleic acid are included in the assay design in each run); or 3.) a comparative $C_T$ method ($\Delta\Delta C_T$) for relative quantitation of gene expression (wherein the relative amount of the target sequence is compared to any of the reference values chosen and the result is given as relative to the reference value).

The comparative $C_T$ method requires one to first determine the difference ($\Delta C_T$) between the $C_T$ values of the target and the normalizer, wherein: $\Delta C_T = C_T$ (target)$-C_T$ (normalizer). This value is calculated for each sample to be quantitated and one sample must be selected as the reference against which each comparison is made. The comparative $\Delta\Delta C_T$ calculation involves finding the difference between each sample's $\Delta C_T$ and the baseline's $\Delta CT$, and then transforming these values into absolute values according to the formula $2^{-\Delta\Delta C_T}$.

In one aspect of the invention, it was desirable to compare the activity of various *Yarrowia lipolytica* promoters, to facilitate a determination of each promoter's strength for use in future applications wherein a suite of promoters would be necessary to construct chimeric genes useful for the production of ω-6 and ω-3 fatty acids.

Generation of Mutants Derived from the gpd and gpm Genes and Putative Promoter Regions In alternate embodiments mutant promoters may be constructed, wherein the DNA sequence of the promoter has one or more nucleotide substitutions (i.e., deletions, insertions, substitutions, or addition of one or more nucleotides in the sequence) which do not affect (in particular impair) the yeast promoter activity. Regions that can be modified without significantly affecting the yeast promoter activity can be identified by deletion studies. A mutant promoter of the present invention has at least about 20%, preferably at least about 40%, more preferably at least about 60%, more preferably at least about 80%, more preferably at least about 90%, more preferably at least about 100%, more preferably at least about 200%, more preferably at least about 300% and most preferably at least about 400% of the promoter activity of the GPD promoter region and/or the GPDIN promoter region and/or the GPM promoter region described herein. Examples of the GPD, GPDIN and GPM promoter regions are the DNA sequences set forth in SEQ ID NOs:66, 70 and 67, respectively.

Methods for mutagenesis are well known in the art and suitable for the generation of mutant promoters or mutant genes. For example, in vitro mutagenesis and selection, PCR based random mutagenesis, site-directed mutagenesis, or other means can be employed to obtain mutations of the naturally occurring regulatory sequences and genes of the instant invention. This would permit production of a putative promoter having a more desirable level of promoter activity in the host cell, or production of a polypeptide having more desirable physical and kinetic parameters for function in the host cell.

If desired, the regions of a nucleotide of interest important for promoter or enzymatic activity, respectively, can be determined through routine mutagenesis, expression of the resulting mutant promoters or polypeptides and determination of their activities. Mutants may include deletions, insertions and point mutations, or combinations thereof. A typical functional analysis begins with deletion mutagenesis to determine either: 1.) the minimum portion of the putative promoter necessary for activity; or 2.) the N- and C-terminal limits of the protein necessary for function. Subsequently, internal deletions, insertions or point mutants are made to further determine regions necessary for function. Other techniques such as cassette mutagenesis or total synthesis also can be used.

Deletion mutagenesis of a coding sequence is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites.

Internal deletions in a putative promoter region or within a coding sequence can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR, while point mutations are made through techniques such as site-directed mutagenesis or mutagenic PCR.

Chemical mutagenesis also can be used for identifying regions of a putative promoter region or polypeptide important for activity. A mutated construct is expressed, and the ability of the resulting altered promoter or protein, respectively, is assayed. Such structure-function analysis can determine which regions may be deleted, which regions tolerate insertions, and which point mutations allow the mutant promoter or protein to function in substantially the same way as the native promoter or protein. All such mutant promoters and nucleotide sequences encoding polypeptides that are derived from the instant promoters and genes described herein are within the scope of the present invention.

Isolation of Homologs to the gpd and gpm Genes and Putative Promoter Regions

It will be appreciated by a person of skill in the art that the regulatory sequences and genes of the present invention have homologs in a variety of yeast species; and, the use of the regulatory sequences and genes for heterologous gene expression are not limited to those regulatory sequences and genes derived from *Yarrowia lipolytica*, but extend to homologs in other yeast species. For example, the invention encompasses homologs derived from oleaginous genera including, but not limited to: *Yarrowia, Candida, Rhodotorula, Rhodosporidium, Cryptococcus, Trichosporon* and *Lipomyces;* examples of preferred species within these genera include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus* and *R. graminis*.

Homology typically is measured using sequence analysis software, wherein the term "sequence analysis software" refers to any computer algorithm or software program (commercially available or independently developed) that is useful for the analysis of nucleotide or amino acid sequences. In general, such computer software matches similar sequences by assigning degrees of homology to various substitutions, deletions and other modifications.

As is well known in the art, isolation of homologous regulatory sequences or genes using sequence-dependent protocols is readily possible using various techniques. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, putative promoter regions or genes encoding similar proteins or polypeptides to those of the instant invention could be isolated directly by using all or a portion of the instant nucleic acid molecules as DNA hybridization probes to screen libraries from any desired microbe using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation, or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis (Ed.), (1986) pp 33-50 IRL: Herndon, Va.; and Rychlik, W., *In Methods in Molecular Biology*, White, B. A. (Ed.), (1993) Vol. 15, pp 31-39, PCR Protocols: Current Methods and Applications. Humania: Totowa, N.J.).

Generally two short segments of the instant sequences may be used in polymerase chain reaction protocols to amplify longer nucleic acid molecules encoding homologous polynucleotides from DNA or RNA. The polymerase chain reaction may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor encoding microbial genes.

Alternatively, the instant sequences may be employed as hybridization reagents for the identification of homologs. The basic components of a nucleic acid hybridization test include a probe, a sample suspected of containing the nucleotide sequence of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Recombinant Expression in Yeast

Regulatory sequences that are useful to drive expression of a coding gene of interest in the desired host cell are selected from those derived from the upstream portion of the gpm gene and from the upstream and 5' portion of the gpd gene. The DNA fragments set forth in SEQ ID NOs:66, 67 and 70 for example, comprise promoters regions as described herein while SEQ ID NO:97 is an intron having enhancer activity.

The promoter regions may be identified from the upstream sequences of gpd and gpm genes and their homologs and isolated according to common methods (Maniatis, supra). Alternatively, it is possible to create a chimeric promoter that comprises the intron of the gpd gene, as set forth in SEQ ID NO:97 (see, for example, SEQ ID NO:84). Once the promoter regions are identified and isolated (or synthetically constructed), they may be operably linked to a coding region of interest to be expressed in a suitable expression vector. These chimeric genes may then be expressed in natural host cells and heterologous host cells, particularly in the cells of oleaginous yeast hosts. Thus, one aspect of the present invention provides a recombinant expression vector comprising a yeast promoter of the invention.

In a further aspect, the invention provides a method of expressing a coding region of interest in a transformed yeast cell, wherein a transformed cell is provided having a chimeric gene comprising: (i) a GPD, GPDIN or GPM promoter region; and (ii) a coding region of interest expressible in the host, wherein the GPD promoter region, GPDIN promoter region or GPM promoter region is operably linked to the coding region of interest; and the transformed cell is grown under conditions wherein the chimeric gene is expressed. The polypeptide so produced can optionally be recovered from the culture.

In an alternate aspect, the invention provides a method of expressing a coding region of interest in a transformed yeast cell, wherein a transformed cell is provided having a chimeric gene comprising: (i) a chimeric promoter region comprising the gpd intron (SEQ ID NO:97) or gpd enhancer therein; and (ii) a coding region of interest expressible in the host, wherein the chimeric promoter region comprising the gpd intron or gpd enhancer therein is operably linked to the coding region of interest; and wherein the transformed cell is grown under conditions wherein the chimeric gene is expressed. The polypeptide so produced can optionally be recovered from the culture.

Microbial expression systems and expression vectors are well known to those skilled in the art. Any of these could be used to construct chimeric genes comprising the regulatory sequences derived from the gpm and gpd genes for production of any specific coding region of interest suitable for expression in a desirable yeast host cell. These chimeric genes could then be introduced into appropriate microorganisms by integration via transformation to provide high-level expression of the enzymes upon induction. Alternatively, the regulatory sequences can be cloned into a plasmid that is capable of transforming and replicating itself in the preferred yeast host cell. The coding region of interest to be expressed can then be cloned downstream from the regulatory sequences. Once the recombinant host is established, gene expression can be accomplished by growing the cells under suitable conditions (infra).

Suitable Coding Regions of Interest

Useful chimeric genes will include the GPM promoter region, the GPD promoter region, the GPDIN promoter region of the gpd gene as defined herein, a chimeric promoter comprising the intron or enhancer of the gpd gene, or mutant promoters thereof, operably linked to a suitable coding region of interest to be expressed in a preferred host cell.

Coding regions of interest to be expressed in the recombinant yeast host may be either endogenous to the host or heterologous and must be compatible with the host organism. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides. Further, these coding regions of interest may be, for example, structural proteins, enzymes (e.g., oxidoreductases, transferases, hydrolyases, lyases, isomerases, ligases), or peptides. A non-limiting list includes genes encoding enzymes such as acyltransferases, aminopeptidases, amylases, carbohydrases, carboxypeptidases, catalyases, cellulases, chitinases, cutinases, cyclodextrin glycosyltransferases, deoxyribonucleases, esterases, α-galactosidases, β-glucanases, β-galactosidases, glucoamylases, α-glucosidases, β-glucosidases, invertases, laccases, lipases, mannosidases, mutanases, oxidases, pectinolytic enzymes, peroxidases, phospholipases, phytases, polyphenoloxidases, proteolytic enzymes, ribonucleases, transglutaminases or xylanases.

Preferred in the present invention in some embodiments are coding regions of the enzymes involved in the production of microbial oils, including ω-6 and ω-3 fatty acids. Many microorganisms, including algae, bacteria, molds and yeast, can synthesize PUFAs and omega fatty acids in the ordinary course of cellular metabolism. Particularly well-studied are fungi including Schizochytrium aggregatm, species of the genus Thraustochytrium and Morteriella alpina. Additionally, many dinoflagellates (Dinophyceaae) naturally produce high concentrations of PUFAs. As such, a variety of genes involved in oil production have been identified through genetic means and the DNA sequences of some of these genes are publicly available (e.g., see GenBank Accession No.s AY131238, Y055118, AY055117, AF296076, AF007561, L11421, NM_031344, AF465283, AF465282, AF465281, AF110510, AF419296, AB052086, AJ250735, AF126799, AF126798, AF199596, AF226273, AF320509, AB072976, AF489588, AJ510244, AF419297, AF07879, AF067654, AB022097, AF489589.1, AY332747, AAG36933, AF110509, AB020033, AAL13300, AF417244, AF161219, X86736, AF240777, AB007640, AB075526, AP002063, NP_441622, BAA18302, BAA02924, AAL36934, AF338466, AF438199, E11368, E11367, D83185, U90417, AF085500, AY504633, NM_069854, AF230693, AX464731, NM_119617, NM_134255, NM_134383, NM_134382, NM_068396, NM_068392, NM_070713, NM_068746 and NM_064685). Additionally, the patent literature provides many additional DNA sequences of genes (and/or details concerning several of the genes above and their methods of isolation) involved in oil production. See, for example: U.S. Pat. No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); WO 94/11516, U.S. Pat. No. 5,443,974 and WO 03/099216 (Δ12 desaturases); U.S. 2003/0196217 (Δ17 desaturase); WO 02/090493 (Δ4 desaturase); WO 00/34439 (Δ8 desaturases); WO 00/12720, U.S. 2002/0139974 and U.S. 2004/0111763 (elongases), each of which is herein incorporated by reference in its entirety.

Components of Vectors/DNA Cassettes

Vectors or DNA cassettes useful for the transformation of suitable host cells are well known in the art. The specific choice of sequences present in the construct is dependent upon the desired expression products (supra), the nature of the host cell, and the proposed means of separating transformed cells versus non-transformed cells. Typically, however, the vector or cassette contains regulatory sequences directing transcription and translation of the relevant gene(s), a selectable marker, and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence motif to obtain optimal gene expression. For expression in yeast, this can be done by site-directed mutagenesis of an inefficiently expressed gene to include the favored translation initiation motif.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly Saccharomyces, Schizosaccharomyces, Candida, Yarrowia or Kluyveromyces. The 3'-regions of mammalian genes encoding γ-interferon and α-2 interferon are also known to function in yeast. Termination control regions may also be derived from various genes native to the preferred host. Optionally, a termination site may be unnecessary; however, it is most preferred if included.

As one of skill in the art is aware, merely inserting a chimeric gene into a cloning vector does not ensure that it will be successfully expressed at the level needed. In response to needs for high expression rates, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of a chimeric gene comprising the GPM promoter region, GPD promoter region, GPDIN promoter region, gpd intron or enhancer of the gpd gene as defined herein, or a mutant promoter thereof, operably linked to a suitable coding region of interest.

Transformation of Yeast Cells

Once an appropriate chimeric gene has been constructed that is suitable for expression in a yeast cell, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory sequences can be provided by the endogenous locus.

Where two or more genes are expressed from separate replicating vectors, it is desirable that each vector has a different means of selection and should lack homology to the other constructs to maintain stable expression and prevent reassortment of elements among constructs. Judicious choice of regulatory sequences, selection means and method of propagation of the introduced construct can be experimentally determined so that all introduced genes are expressed at the necessary levels to provide for synthesis of the desired products.

Constructs comprising a coding region of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); β-glucuronidase (GUS) can convert the substrate "MUG" (4-methylumbellifery-b-glucuronide) to a colored product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Preferred for use herein are resistance to kanamycin, hygromycin and the aminoglycoside G418, as well as ability to grow on media lacking uracil or leucine.

Techniques to Up-Regulate Expression of a Chimeric Gene Comprising Regulatory Sequences of the Invention Operably Linked to a Coding Region of Interest Additional copies a particular coding region of interest (operably linked to a GPM promoter, GPD promoter, a GPDIN promoter, or a chimeric promoter comprising the gpd intron or gpd enhancer) may be introduced into the host to increase expression. Expression of the coding region of interest also can be increased by removing/deleting destabilizing sequences from either the mRNA or the encoded protein, or by adding stabilizing sequences to the mRNA (U.S. Pat. No. 4,910,141).

Yet another approach to increase expression of a coding region of interest is to increase the translational efficiency of the encoded mRNAs by replacement of codons in the native gene with those for optimal gene expression in the selected host microorganism. As will be appreciated by one skilled in the art, use of host preferred codons can substantially enhance the expression of the foreign gene encoding the polypeptide. In general, host preferred codons can be determined within a particular host species of interest by examining codon usage in proteins (preferably those expressed in the largest amount) and determining which codons are used with highest frequency. Then, the coding sequence for a polypeptide of interest can be synthesized in whole or in part using the codons preferred in the host species.

Additionally, as shown herein, some enhancer elements located in the 5' or 3' noncoding region of a gene or introns can also be used to enhance the expression of a coding region of interest.

Preferred Hosts

Preferred host cells for expression of the instant genes and coding regions of interest operably linked to the instant regulatory sequences herein are yeast cells (where oleaginous yeast are most preferred where the desired use is for the production of microbial oils, infra). Oleaginous yeast are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)). The *Y. lipolytica* strain designated as ATCC #76982 was the particular strain from which the GPD, GPDIN and GPM promoters and genes were isolated herein.

Industrial Production Using Transformed Yeast Expressing a Suitable Coding Region of Interest In general, media conditions which may be optimized for high-level expression of a particular coding region of interest include the type and amount of carbon source, the type and amount of nitrogen source, the carbon-to-nitrogen ratio, the oxygen level, growth temperature, pH, length of the biomass production phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins, and other components known to those skilled in the art suitable for the growth of the microorganism.

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Host cells comprising a suitable coding region of interest operably linked to the regulatory sequences of the present invention may be cultured using methods known in the art. For example, the cell may be cultivated by shake flask cultivation, small-scale or large-scale fermentation in laboratory or industrial fermentors performed in a suitable medium and under conditions allowing expression of the coding region of interest.

Where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process.

A batch fermentation process is a closed system wherein the media composition is fixed at the beginning of the process and not subject to further additions beyond those required for maintenance of pH and oxygen level during the process. Thus, at the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high growth log phase and finally to a stationary phase, wherein the growth rate is diminished or halted. Left untreated, cells in the stationary phase will eventually die. A variation of the standard batch process is the fed-batch process, wherein the source is continually added to the fermentor over the course of the fermentation process. A fed-batch process is also suitable in the present invention. Fed-batch processes are useful when catabolite repression is apt to inhibit the metabolism of the cells or where it is desirable to have limited amounts of source in the media at any one time. Measurement of the source concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), herein incorporated by reference.

Commercial production may also be accomplished by a continuous fermentation process, wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

DESCRIPTION OF PREFERRED EMBODIMENTS

Although the regulatory sequences derived from the *Yarrowia lipolytica* gpd and gpm genes of the present invention will be suitable for expression of any suitable coding region of interest in an oleaginous yeast, in a preferred embodiment the promoters will be utilized in the development of an oleaginous yeast that accumulates oils enriched in PUFAs. Toward this end, it is necessary to introduce and express e.g., desaturases and elongases that allow for the synthesis and accumulation of ω-3 and/or ω-6 fatty acids.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond"

along the carbon backbone (e.g., usually between the 9$^{th}$ and 10$^{th}$ carbon atom as for palmitoleic acid (16:1) and oleic acid (18:1)), while "polyunsaturated fatty acids" (or "PUFAs") have at least two double bonds along the carbon backbone (e.g., between the 9$^{th}$ and 10$^{th}$, and 12$^{th}$ and 13$^{th}$ carbon atoms for linoleic acid (18:2); and between the 9$^{th}$ and $_1$Oth, 12$^{th}$ and 13$^{th}$, and 15$^{th}$ and 16$^{th}$ for α-linolenic acid (18:3)).

"PUFAs" can be classified into two major families (depending on the position (n) of the first double bond nearest the methyl end of the fatty acid carbon chain). Thus, the "ω-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "ω-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of this disclosure, the omega-reference system will be used to indicate the number of carbons, the number of double bonds and the position of the double bond closest to the omega carbon, counting from the omega carbon (which is numbered 1 for this purpose). This nomenclature is shown below in Table 2, in the column titled "Shorthand Notation". The remainder of the Table summarizes the common names of ω-3 and ω-6 fatty acids, the abbreviations that will be used throughout the remainder of the specification, and each compounds' chemical name.

TABLE 2

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

Microbial Biosynthesis of Fatty Acids

In general, lipid accumulation in oleaginous microorganisms is triggered in response to the overall carbon to nitrogen ratio present in the growth medium. When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol, and subsequent cleavage of the citrate by ATP-citrate lyase to yield acetyl-CoA and oxaloacetate. Acetyl-CoA is the principle building block for de novo biosynthesis of fatty acids. The first committed step of fatty acid biosynthesis is the synthesis of malonyl-CoA, produced via carboxylation of acetyl-CoA. Fatty acid synthesis is catalyzed by a multi-enzyme fatty acid synthase complex and occurs by the condensation of eight two-carbon fragments (acetyl groups from acetyl-CoA) to form a 16-carbon saturated fatty acid, palmitate.

Palmitate is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate are converted to their unsaturated derivatives, palmitoleic (16:1) and oleic (18:1) acids, respectively, by the action of a Δ9 desaturase.

Biosynthesis of Omega-3 and Omega-6 Fatty Acids

Simplistically, the metabolic process that converts LA to GLA, DGLA and ARA (the ω-6 pathway) and ALA to STA, ETA, EPA and DHA (the ω-3 pathway) involves elongation of the carbon chain through the addition of carbon atoms and desaturation of the molecule through the addition of double bonds. This requires a series of special desaturation and elongation enzymes present in the endoplasmic reticulim membrane, hereinafter referred to as "PUFA biosynthetic pathway enzymes".

More specifically, "PUFA biosynthetic pathway enzymes" or "ω-3/ω-6 fatty acid biosynthetic pathway enzymes" will refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ8 desaturase, a Δ9 desaturase and/or an elongase(s). For further clarity within the present disclosure, the term "desaturase" refers to a polypeptide that can desaturate one or more fatty acids to produce a mono- or polyunsaturated fatty acid or precursor of interest. Thus, despite use of the omega-reference system to refer to specific fatty acids, it is more convenient to indicate the activity of a desaturase by counting from the carboxyl end of the source using the delta-system. For example, a Δ17 desaturase will desaturate a fatty acid between the 17$^{th}$ and 18$^{th}$ carbon atom numbered from the carboxyl-terminal end of the molecule and can, for example, catalyze the conversion of ARA to EPA and/or DGLA to ETA. In contrast, the term "elongase" refers to a polypeptide that can elongate a fatty acid carbon chain to produce a mono- or polyunsaturated fatty acid that is 2 carbons longer than the fatty acid source that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA.

Synthesis of ω-6 fatty acids occurs in the following fashion: oleic acid (the first of the ω-6 fatty acids) is converted to LA (18:2) by the action of a Δ12 desaturase (FIG. 11). Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase. Alternatively, LA is converted to EDA by a Δ9 elongase; and a Δ8 desaturase then converts the EDA to DGLA.

In contrast, ω-3 fatty acids are all derived from linoleic acid (LA). Specifically: 1.) LA is converted to ALA by the action of a Δ15 desaturase; 2.) ALA is converted to STA by the activity of a Δ6 desaturase; 3.) STA is converted to ETA by the activity of an elongase; and 4.) ETA is converted to EPA by the activity of a Δ5 desaturase. Alternatively, ETA and EPA can be produced from DGLA and ARA, respectively, by the activity of a Δ17 desaturase. Or, in another embodiment, a Δ9 elongase is able to catalyze the conversion of ALA to ETrA; the ETrA is then converted to ETA by a Δ8 desaturase. EPA can be further converted to DHA by the activity of an elongase and a Δ4 desaturase.

Production of PUFAs

As will be obvious to one skilled in the art, the particular functionalities required to be introduced into a host organism for production of a particular PUFA final product will depend on the host cell (and its native PUFA profile and/or desaturase profile), the availability of substrate and the desired end product(s). As shown in FIG. 11, LA, GLA, EDA, DGLA, ARA, ALA, STA, ETrA, ETA, EPA, DPA and DHA may all be produced in oleaginous yeast, by introducing various combinations of the following PUFA enzyme functionalities: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s). One skilled in the art will be able to identify various candidate genes encoding each of the above enzymes, according to publicly available literature (e.g., GenBank), the patent literature, and experimental analysis of microorganisms having the ability to produce PUFAs. Thus, a variety of desaturases and elongases are suitable as coding regions of interest in the present invention. These coding regions of interest could be operably linked to the GPD promoter, GPDIN promoter, GPM promoter and/or a chimeric promoter comprising the gpd intron or gpd enhancer of the present invention (or mutant promoters thereof) and used as chimeric genes for expression of various ω-6 and ω-3 fatty acids, using techniques well known to those skilled in the art (see, for example co-pending U.S. patent applications Ser. Nos. 10/840,579 and 60/624,812, each herein incorporated entirely by reference). As such, the invention provides a method for the production of ω-3 and/or ω-6 fatty acids comprising:

a) providing a transformed oleaginous yeast host cell comprising a chimeric gene, comprising:
  1) a regulatory sequence of a gene selected from the group consisting of: the gpm gene and the gpd gene; and
  2) a coding region of interest expressible in the oleaginous yeast encoding an enzyme of a functional ω-3/ω-6 fatty acid biosynthetic pathway;
  wherein the regulatory sequence and coding region are operably linked; and
(b) contacting the host cell of step (a) under suitable growth conditions whereby one or more ω-3 or ω-6 fatty acids are produced.

In preferred embodiments, the regulatory sequence's nucleic acid sequence is selected from the group consisting of: SEQ ID NOs:23, 27, 66, 67, 70 and 97 (and subsequences and mutant promoters thereof); and the coding region of interest is any desaturase or elongase suitable for expression in the oleaginous yeast for the production of ω-3 or ω-6 fatty acids.

For production of the greatest and the most economical yield of PUFAs, the transformed oleaginous yeast host cell is grown under conditions that optimize desaturase and elongase activities by optimizing expression of the chimeric genes of the present invention, wherein these chimeric genes comprise a regulatory sequence of a gpm or gpd gene and a coding region of interest encoding a PUFA biosynthetic pathway enzyme.

In the fermentation media, particular attention is given to several metal ions (e.g., $Mn^{+2}$, $Co^{+2}$, $Zn^{+2}$, $Mg^{+2}$) that promote synthesis of lipids and PUFAs (Nakahara, T. et al. *Ind. Appl. Single Cell Oils*, D. J. Kyle and R. Colin, eds. pp 61-97 (1992)).

The preferred "fermentable carbon source" for production of oleaginous yeast expressing various ω-6 and ω-3 fatty acids will include, but is not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil. Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

Purification of PUFAs

The PUFAs produced in a host microorganism as described herein may be found as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification, and physical means such as presses, or combinations thereof. Of particular interest is extraction with methanol and chloroform in the presence of water (E. G. Bligh & W. J. Dyer, Can. *J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation or iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (hereinafter "Maniatis"); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

A leucine autotrophic strain of *Yarrowia lipolytica* was purchased from the American Type Culture Collection (Rockville, Md.; ATCC #76982) and used for functional assays. *Y. lipolytica* strains were usually grown at 28° C. on YPD agar (1% yeast extract, 2% bactopeptone, 2% glucose, 2% agar). For selection of transformants, minimal medium (0.17% yeast nitrogen base (DIFCO Laboratories) without ammonium sulfate or amino acids, 2% glucose, 0.1% proline, pH 6.1) was used. Supplements of adenine, leucine, lysine and/or uracil were added to a final concentration of 0.01%.

General molecular cloning was performed according to standard methods (Sambrook et al., supra). Oligonucleotides were synthesized by Sigma-Genosys (Spring, Tex.). Site-directed mutagenesis was performed using Stratagene's QuikChange™ Site-Directed Mutagenesis kit (San Diego, Calif.), per the manufacturer's instructions. When polymerase chain reaction (PCR) or site-directed mutagenesis was involved in subcloning, the constructs were sequenced to confirm that no errors had been introduced to the sequence. PCR products were cloned into Promega's pGEM-T-easy vector (Madison, Wis.).

Manipulations of genetic sequences were accomplished using the suite of programs available from the Genetics Computer Group Inc. (Wisconsin Package Version 9.0, Genetics Computer Group (GCG), Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "h" means hour(s), "d" means day(s), "µl" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s), "kB" means kilobase (s) and "AA" means amino acid.

Example 1

Isolation of a Portion of the *Yarrowia lipolytica* Glyceraldehyde-3-phosphate dehydrogenase ("GPD")

The present Example describes the identification of a portion of the *Yarrowia lipolytica* gene encoding GPD (SEQ ID NOs:11 and 12), by use of primers derived from conserved regions of other GPD sequences.

Figure 1A:
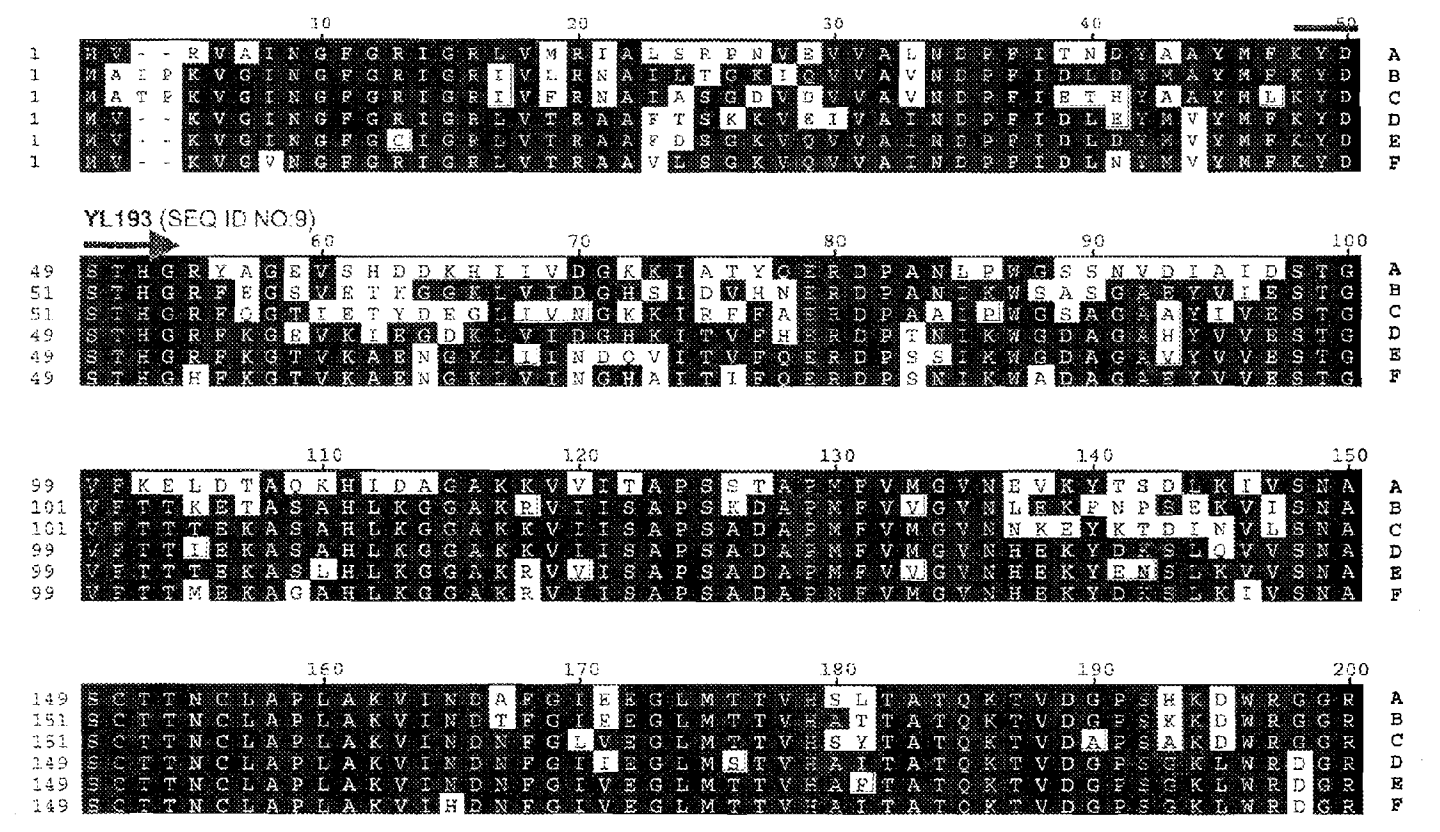

A comparison of the various GPD protein sequences encoding gpd genes from *Saccharomyces cerevisiae* (GenBank Accession No. CM24607; SEQ ID NO:1), *Schizosaccharomyces pombe* (GenBank Accession No. NP_595236; SEQ ID NO:2), *Aspergillus oryzae* (GenBank Accession No. MK08065; SEQ ID NO:3), *Paralichthys olivaceus* (GenBank Accession No. BM88638; SEQ ID NO:4), *Xenopus laevis* (GenBank Accession No. P51469; SEQ ID NO:5) and *Gallus gallus* (GenBank Accession No. DECHG3; SEQ ID NO:6) showed that there were several stretches of conserved amino acid sequence between the 6 different organisms (FIGS. 1A and 1B). Thus, two degenerate oligonucleotides (shown below), corresponding to the conserved 'KYDSTHG' (SEQ ID NO:7) and 'TGAAKAV' (SEQ ID NO:8) amino acid sequences, respectively, were designed and used to amplify a portion of the coding region of GPD from *Y. lipolytica*:

```
Degenerated oligonucleotide YL193     (SEQ ID NO:9)
    AAGTACGAYTCBACYCAYGG Degenerated oligonucleotide YL194     (SEQ ID NO:10)
    ACRGCCTTRGCRGCDCCRGT
[Note: The nucleic acid degeneracy code used for
SEQ ID NOs:9 and 10 was as follows: R = A/G; Y =
C/T; B = C/G/T; and D = A/G/T.]
```

Based on the full-length sequences of the GPD sequences of FIG. 1, it was hypothesized that the *Yarrowia lipolytica* gpd gene amplified as described above would be missing ~50 amino acids from its N-terminus and about ~115 amino acids from its C-terminus.

The PCR amplification was carried out in a 50 μl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer, 50 ng genomic DNA of *Y. lipolytica* (ATCC #76982) and 1 μl of Taq DNA polymerase (Epicentre Technologies). The thermocycler conditions were set for 35 cycles at 95° C. for 1 min, 56° C. for 30 sec, and 72° C. for 1 min, followed by a final extension at 72° C. for 10 min.

The PCR products were purified using a Qiagen PCR purification kit (Valencia, Calif.) and then further purified following gel electrophoresis in 1% (w/v) agarose. Subequently, the PCR products were cloned into the pGEM-T-easy vector (Promega, Madison, Wis.). The ligated DNA was used to transform cells of *E. coli* DH5α and transformants were selected on LB agar containing ampicillin (100 μg/mL). Analysis of the plasmid DNA from one transformant confirmed the presence of a plasmid of the expected size, and designated as "pT-GPD".

Sequence analyses showed that pT-GPD contained a 507 bp fragment (SEQ ID NO:11). Identity of this sequence was determined by conducting BLAST (Basic Local Alignment Search Tool; Altschul, S. F., et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). Similarity to all publicly available DNA sequences contained in the "nr" database was determined using the BLASTN algorithm provided by the National Center for Biotechnology Information (NCBI). The DNA sequence was translated in all reading frames and compared for similarity to all publicly available protein sequences contained in the "nr" database, using the BLASTX algorithm (Gish, W. and States, D. J. *Nature Genetics* 3:266-272 (1993)) provided by the NCBI. The results of the BLAST comparison summarizing the sequence to which SEQ ID NO:11 has the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

Figure 2:
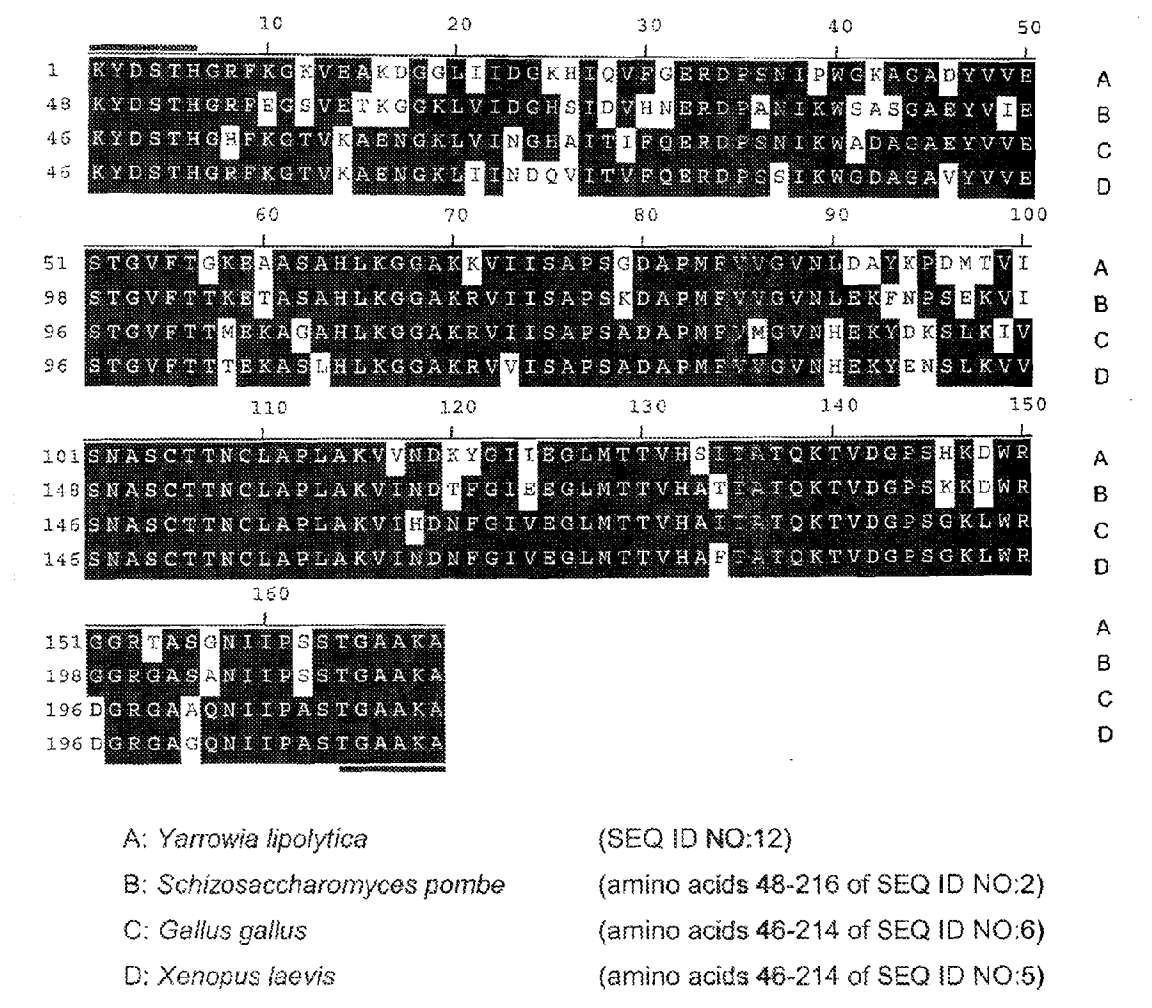

The 507 bp of pT-GPD was found to encode 169 amino acids (SEQ ID NO:12). This amino acid fragment had 77% identity and 84% similarity (FIG. 2) with the GPD protein sequence of fission yeast (GenBank Accession No. NP_595236), with an expectation value of 6e-68. The *Yarrowia* sequence possessed the 'KYDSTHG' (SEQ ID NO:7) and 'TGAAKAV' (SEQ ID NO:8) amino acid sequences (corresponding to the degenerate primers used to amplify the fragment) at its N- and C-termini. Further sequence comparison of this partial GPD sequence determined that it also shared about 72% and 74% identity with the GPD proteins from chick (GenBank Accession No. DECHG3) and frog (GenBank Accession No. P51469), respectively (FIG. 2).

Example 2

Identification of the *Yarrowia lipolytica* Phosphoglycerate Mutase (GPM)

The present Example describes the identification of the *Yarrowia lipolytica* gene encoding GPM, by use of a *S. cerevisiae* GPM protein sequence as a query sequence against a *Y. lipolytica* genomic database.

Specifically, the *S. cerevisiae* GPM protein sequence (GenBank Accession No. NP_012770; SEQ ID NO:13) was used in BLAST searches (as described in Example 1) against the public *Y. lipolytica* database of the "Yeast project Genolevures" (sponsored by the Center for Bioinformatics, LaBRI, bâtiment A30, Université Bordeaux 1, 351, cours de la Libération, 33405 Talence Cedex, France).

One contig ("Contig 2217"; SEQ ID NO:14) was identified that encoded GPM in *Y. lipolytica*. Contig 2217 is 1049 bp in length, although 5 nucleotide positions had ambiguous sequence (having an "n" at nucleotide position 1020, "y" at positions 39, 62, 331; and a "m" at position 107). The DNA sequence of Contig 2217 was translated in all reading frames and compared for similarity to all publicly available protein sequences contained in the "nr" database using the BLASTX algorithm (as described in Example 1). Based on these DNA and protein sequence analyses, it was determined that:

The GPM translation initiation codon 'ATG' was at bp 388 within SEQ ID NO:14; thus, Contig 2217 possessed about 388 bp upstream sequence relative to the 'ATG' codon; and Contig 2217 was missing one base at nucleotide position 470, which resulted in a frame shift.

The deduced coding region sequence of GPM that corresponded to Contig 2217 was 651 bp in length (SEQ ID NO:15) and the protein sequence was encoded by SEQ ID NO:16. This 216 amino acid protein had 71% identity, 82% similarity, and an expectation value of 3e-81 with the GPM protein sequence of *S. cerevisiae* (GenBank Accession No. NP_012770; Goffeau, A., et al., *Science* 274(5287):546 (1996)) (FIG. 3).

Example 3

Isolation of the 5' Upstream Regions of the gpd and gpm Genes From *Yarrowia lipolytica*

To isolate the GPD and GPM regulatory sequences from the genes identified in Examples 1 and 2, a genome-walking technique (TOPO® Walker Kit, Invitrogen, Calif.) was utilized.

Briefly, genomic DNA of *Y. lipolytica* was digested with KpnI, SacI, SphI or PacI, and dephosphorylated with Calf Intestinal Alkaline Phosphatase (CIP), separately. Primer extension reactions were then carried out individually using the dephosphorylated DNA as template and one of the following oligonucleotides as primer: YL206 (SEQ ID NO:17) for GPD and YL196 (SEQ ID NO:18) for GPM. The primer extended products were linked with TOPO® linker and used as templates for the first PCR reactions using primers of LinkAmp Primer1 and a second appropriate oligonucleotide. Specifically, YL207 (SEQ ID NO:19) was used as the second primer targeted for the upstream promoter region of GPD and YL197 (SEQ ID NO:20) was used as the second primer for PCR reactions targeted to the upstream GPM promoter region. The PCR amplifications were carried out in a 50 μl total volume, comprising: PCR buffer (containing 10 mM KCl, 10 mM (NH$_4$)$_2$SO$_4$, 20 mM Tris-HCl (pH 8.75), 2 mM MgSO$_4$, 0.1% Triton X-100), 100 µg/mL BSA (final concentration), 200 µM each deoxyribonucleotide triphosphate, 10 pmole of each primer and 1 µl of Taq DNA polymerase (Epicentre Technologies). The thermocycler conditions were set for 35 cycles at 95° C. for 1 min, 56° C. for 30 sec, and 72° C. for 1 min, followed by a final extension at 72° C. for 10 min.

Second PCR reactions were then carried out using the first PCR product as template and primers of LinkAmp primer 2 and the appropriate oligo-nucleotide. Specifically, the first PCR product for GPD was used as template in a reaction comprising LinkAmp primer 2 and YL208 (SEQ ID NO:21); in contrast, the first PCR product for GPM was used as template in a reaction comprising LinkAmp primer 2 and YL198 (SEQ ID NO:22). The PCR amplifications were carried out as described above.

The PCR products comprising the 5' upstream regions of the gpd and gpm genes were each individually purified using a Qiagen PCR purification kit, followed by gel electrophoresis in 1% (w/v) agarose. Products were then cloned into the pGEM-T-easy vector (Promega, Madison, Wis.). The ligated DNA was used to transform E. coli DH5α and transformants were selected on LB agar containing ampicillin (100 µg/mL).

Analysis of the plasmid DNA from one transformant comprising the 5' upstream region of the gpd gene confirmed the presence of the expected plasmid, designated "pT-GPDP". Sequence analyses showed that pT-GPDP contained a fragment of 1848 bp (SEQ ID NO:23), which included 1525 bp of 5' upstream sequence from the nucleotide 'A' (designated as +1) of the translation initiation codon 'ATG' of the gpd gene. A complete assembly of overlapping SEQ ID NOs:23 and 11 yielded a single contig comprising 1525 bp upstream of the GPD initiation codon and 791 bp of the gene (SEQ ID NO:24; FIG. 4). Further analysis of the partial gene sequence (+1 to +791) revealed the presence of an intron (base pairs +49 to +194; SEQ ID NO:97). Thus, the partial cDNA sequence encoding the gpd gene in Y. lipolytica is only 645 bp in length (SEQ ID NO:25) and the corresponding protein sequence (SEQ ID NO:26) is 215 amino acids. The protein was compared via BLAST analysis for similarity to all publicly available protein sequences (as described in Example 1). Based on this analysis, it was determined that the partial GPD protein was most similar to the GPD of Cryotococcus cyrvatus (GenBank Accession No.s Q9Y796 and MD25080) (81% identical).

Analysis of the plasmid DNA from one transformant comprising the 5' upstream region of the gpm gene confirmed the presence of the expected plasmid, designated "pT-GPML". Sequence analyses showed that pT-GPML contained a fragment of 953 bp (SEQ ID NO:27). This clone possessed 875 bp of 5' upstream sequence from the translation initiation codon of the gpm gene. Assembly of DNA corresponding to overlapping SEQ ID NOs:27 and 15 yielded a single contig of DNA represented as SEQ ID NO:28 (FIG. 5). This contig therefore contained the −875 to +662 region of the gpm gene, wherein the 'A' position of the 'ATG' translation initiation codon was designated as +1.

Example 4

Isolation of a Fructose-Bisphosphate Aldolase Promoter from Y. lipolytica

The present Example describes the identification of a portion of the Yarrowia lipolytica gene encoding FBA1 and the isolation of the 5' upstream region of the gene using a genome-walking technique (as described in U.S. patent application Ser. No. 10/987,548 (filed Nov. 12, 2004)).

Identification of a Portion of the Yarrowia lipolytica Gene Encoding FBA1

A comparison of the various protein sequences encoding fba1 genes from Saccharomyces cerevisiae (GenBank Accession No. NP_012863), Schizosaccharomyces pombe (GenBank Accession No. NP_595692), Aspergillus oryzae (GenBank Accession No. BAB12232), Haemophilus influenzae (GenBank Accession No. NP_438682) and Pasteurella multocida (GenBank Accession No. NP_246800) showed that there were several stretches of conserved amino acid sequence between the 5 different organisms. Thus, two degenerate oligonucleotides (shown below), corresponding to the conserved 'AIPAVNV' (SEQ ID NO:29) and 'EMEIGIT' (SEQ ID NO:30) amino acid sequences, respectively, were designed and used to amplify a portion of the coding region of fba1 from Y. lipolytica:

```
Degenerate oligonucleotide YL214    (SEQ ID NO:31)
    GCYATYCCYGCYGTYAACGT

Degenerate oligonucleotide YL216    (SEQ ID NO:32)
    GTRATDCCRATCTCCATCTC
[Note: The nucleic acid degeneracy code used for
SEQ ID NOs:31 and 32 was as follows: R = A/G; Y =
C/T; and D = A/G/T.]
```

Based on the full-length sequences of the fba1 sequences, it was hypothesized that the Yarrowia lipolytica fba1 gene amplified as described above would be missing ~31 amino acids from its N-terminus and about ~180 amino acids from its C-terminus.

The PCR amplification was carried out in a 50 µl total volume comprising: PCR buffer (containing 10 mM KCl, 10 mM (NH$_4$)$_2$SO$_4$, 20 mM Tris-HCl (pH 8.75), 2 mM MgSO$_4$, 0.1% Triton X-100), 100 µg/mL BSA (final concentration), 200 µM each deoxyribonucleotide triphosphate, 10 pmole of each primer, 50 ng genomic DNA of Y. lipolytica (ATCC #76982) and 1 µl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The PCR products were purified using a Qiagen PCR purification kit (Valencia, Calif.) and then further purified following gel electrophoresis in 1% (w/v) agarose. Subequently, the PCR products were cloned into the pGEM-T-easy vector (Promega, Madison, Wis.). The ligated DNA was used to transform cells of E. coli DH10B and transformants were selected on LB (1% bacto-tryptone, 0.5% bacto-yeast extract and 1% NaCl) agar containing ampicillin (100 µg/mL). Analysis of the plasmid DNA from one transformant confirmed the presence of a plasmid of the expected size (designated as "pT-FBA1").

Sequence analyses showed that pT-FBA1 contained a 436 bp fragment (SEQ ID NO:33). Identity of this sequence was determined by conducting BLAST (supra) searches for similarity to sequences contained in the BLAST "nr" database. The sequence was analyzed for similarity to all publicly available DNA sequences contained in the "nr" database using the BLASTN algorithm provided by the NCBI. The DNA sequence was translated in all reading frames and compared for similarity to all publicly available protein sequences contained in the "nr" database, using the BLASTX algorithm (Gish, W. and States, D. J., supra) provided by the NCBI.

The results of the BLAST comparison revealed that SEQ ID NO:33, encoding an amino acid fragment of 145 codons (SEQ ID NO:34), had 77% identity and 86% similarity with the FBA protein sequence of *Saccharomyces cerevisiae* (GenBank Accession No. NP_012863), with an expectation value of 9e-54. "% Identity", "% Similarity", and "Expectation value" are defined as described in Example 1. The *Yarrowia* sequence possessed the 'AIPAVNV' (SEQ ID NO:29) and 'EMEIGIT' (SEQ ID NO:30) amino acid sequences (corresponding to the degenerate primers used to amplify the fragment) at its N- and C-termini.

Isolation of the 5' Upstream Regions of the fba1 Gene

Genomic DNA of *Y. lipolytica* was digested with KpnI, SacI, SphI or PacI and each digest was then dephosphorylated with Calf Intestinal Alkaline Phosphatase (CIP), separately. Primer extension reactions were carried out individually using the dephosphorylated DNA as the template and oligonucleotide YL217 (SEQ ID NO:35) as the primer. The primer extended products were linked with TOPO$^R$ linker and used as templates for the first PCR reactions using primers of LinkAmp Primer1 and YL218 (SEQ ID NO:36), according to the instructions within the TOPO$^R$ Walker Kit (Invitrogen, Carlsbad, Calif.) for genome walking. The PCR amplifications were carried out in a 50 µl total volume, using the components and conditions described above. The second PCR reaction was then carried out using the first PCR product as the template and primers LinkAmp primer 2 and YL219 (SEQ ID NO:37).

The PCR product comprising the 5' upstream region of the fba1 gene was purified using a Qiagen PCR purification kit, followed by gel electrophoresis in 1% (w/v) agarose. Products were then cloned into the pGEM-T-easy vector (Promega, Madison, Wis.). The ligated DNA was used to transform *E. coli* DH10B and transformants were selected on LB agar containing ampicillin (100 µg/mL).

Analysis of the plasmid DNA from one transformant comprising the 5' upstream region of the fba1 gene confirmed the presence of the expected plasmid, designated "pT-FBA1P". Sequence analyses showed that pT-FBA1P contained a fragment of 857 bp (SEQ ID NO:38), which included 520 bp of 5' upstream sequence (SEQ ID NO:39) from the nucleotide 'A' (designated as +1) of the putative translation initiation codon 'ATG' of the fba1 gene. A complete assembly of overlapping SEQ ID NOs:33 and 38 yielded a single contig comprising 520 bp upstream of the fba1 putative initiation codon and 633 bp coding region of the fba1 gene (SEQ ID NO:40; FIG. 6). Further analysis of the fba1 DNA sequence (+1 to +635) revealed the presence of an intron of 102 bp (base pairs +64 to +165). Thus, the isolated coding region of the fba1 gene in *Yarrowia lipolytica* is only 531 bp in length (SEQ ID NO:41) and the corresponding amino acid protein sequence (SEQ ID NO:42) is 177 amino acids. The amino acid sequence was compared via BLAST analysis for similarity to all publicly available protein sequences (as described above). Based on this analysis, it was determined that the *Yarrowia* FBA1 protein was most similar to the FBA1 of *Kluyveromyces lactis* (GenBank Accession No.CAC29023) with 73% identity.

The gene walking technique was repeated to obtain more of the upstream sequence of the fba1 gene, using the methodology described above. However, primers ODMW315, ODMW316 and ODMW317 (SEQ ID NOs:4345, respectively) were substituted for primers YL217, YL218 and YL219, respectively. Analysis of the plasmid DNA from one transformant comprising the 5' upstream region of the fba1 gene confirmed the presence of the expected plasmid, designated "pT-FBA1P2". Sequence analyses showed that pT-FBA1P2 contained a fragment of 1152 bp (SEQ ID NO:46), entirely upstream from the 5' sequence of the fba1 gene that was identified from the first round of gene walking. A complete assembly of overlapping SEQ ID NOs:33, 38 and 46 yielded a single contig of 2177 bp (SEQ ID NO:47) comprising 1542 bp (SEQ ID NO:48) upstream and 633 bp downstream of the putative initiation codon of the fba1 gene (FIG. 6).

Example 5

Synthesis of pY5-30

The present Example describes the synthesis of pY5-30, comprising a TEF::GUS::XPR chimeric gene. This was required for comparative studies investigating the promoter activity of TEF, FBA, FBAIN, GPD, GPDIN and GPM, wherein constructs comprising each promoter and a reporter gene were prepared (Examples 6 and 7), transformed (Example 8) and analyzed (Examples 9 and 10). Specifically, the reporter was the *E. coli* gene encoding β-glucuronidase (GUS; Jefferson, R. A. *Nature*. 342(6251):837-838 (1989)).

Amplification of the GUS Coding Region

The GUS coding region was amplified using pBI101 (Jefferson, R. A et al., *EMBO J.* 6:3901-3907 (1987)) as template and oligonucleotides YL33 and YL34 (SEQ ID NOs:49 and 50) as primers. The PCR amplification was carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec, 72° C. for 1 min, followed by a final extension at 72° C. for 10 min. The PCR products were digested with NcoI and PacI.

Synthesis of Plasmid pY5-30

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica*, as diagrammed in FIG. 7. The partially-digested 3598 bp EcoRI fragment containing the ARS18 sequence and LEU2 gene of pINA532 was subcloned into the EcoRI site of pBluescript (Strategene, San Diego, Calif.) to generate pY2.

The TEF promoter (Muller S., et al. Yeast, 14:1267-1283 (1998); SEQ ID NO:51) was amplified from *Y. lipolytica* genomic DNA by PCR using TEF5' and TEF3' (SEQ ID NOs:52 and 53) as primers. PCR amplification was carried out in a 50 µl total volume containing: 100 ng *Yarrowia* genomic DNA, PCR buffer (supra), 100 µg/mL BSA (final concentration), 200 µM each deoxyribonucleotide triphosphate, 10 pmole of each primer and 1 µl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' and XPR3' (SEQ ID NOs:54 and 55) as primers. The PCR amplification was carried out in a 50 μl total volume, using the components and conditions described above. The 179 bp PCR product was digested with SacII and then ligated into the SacII site of pY4 to generate pY5. Thus, pY5 (shown in FIG. 7) contained: a Yarrowia autonomous replication sequence (ARS18); a ColE1 plasmid origin of replication; an ampicillin-resistance gene (Amp$^R$) for selection in E. coli; a Yarrowia LEU2 gene encoding isopropylmalate isomerase, for selection in Yarrowia; the translation elongation promoter ("TEF P"), for expression of heterologous genes in Yarrowia; and the extracellular protease gene terminator (XPR2) for transcriptional termination of heterologous gene expression in Yarrowia.

Plasmid pY5-10 was constructed as a derivative of pY5. First, pY5-4 was constructed by three rounds of site-directed mutagenesis using pY5 as template. A NcoI site located inside the LEU2 reporter gene was eliminated from pY5 using oligonucleotides YL1 and YL2 (SEQ ID NOs:56 and 57) to generate pY5-1. A NcoI site was introduced into pY5-1 between the TEF promoter and XPR transcriptional terminator by site-directed mutagenesis using oligonucleotides YL3 and YL4 (SEQ ID NOs:58 and 59) to generate pY5-2. A PacI site was then introduced into pY5-2 between the TEF promoter and XPR transcriptional terminator using oligonucleotides YL23 and YL24 (SEQ ID NOs:60 and 61) to generate pY54. Finally, a SalI site was introduced into pY54 between the TEF promoter and the LEU2 gene by site-directed mutagenesis using oligonucleotides YL9 (SEQ ID NO:62) and YL10 (SEQ ID NO:63) as primers to generate pY5-10.

Plasmid pY5-30 (FIG. 7; SEQ ID NO:64), comprising a TEF::GUS::XPR chimeric gene, was synthesized by inserting the NcoI/PacI PCR product comprising the GUS coding region (supra) into NcoI/PacI digested pY5-10.

Example 6

Synthesis of pYZGDG, pDMW222 and pYZGMG Comprising the GPD, GPDIN and GPM Promoters The present Example describes the synthesis of pYZGDG (comprising a GPD promoter::GUS::XPR chimeric gene), pDMW222 (comprising a GPDIN promoter::GUS::XPR terminator chimeric gene, wherein GPDIN is the GPD promoter region along with a portion of the 5' coding region comprising the gpd intron) and pYZGMG (comprising a GPM promoter::GUS::XPR chimeric gene). Synthesis of these plasmids first required identification and amplification of the putative GPD, GPDIN and GPM promoter regions. Then, each putative promoter region was cloned into a derivative of pY5-30 (Example 5).

Identification and Amplification of Putative Promoter Regions

After the isolation of the 5' upstream sequence of the gpd and gpm genes by genome walking, the translation start site was identified by looking for the consensus motif around the translation initiation 'ATG' codon and by comparison of the translated coding region of the Yarrowia gpd and gpm genes with the gpd and gpm genes, respectively, from other organisms. Previous studies had determined that the consensus sequence around the 'ATG' initiation codon in Yarrowia lipolytica was 'MAMMATGNHS' (SEQ ID NO:65), wherein the nucleic acid degeneracy code used is as follows: M=A/C; S=C/G; H=A/C/T; and N=A/C/G/T). Thus, the region upstream of the genes' 'ATG' start site was used to identify putative promoter regions.

Thus, the nucleotide region between the −968 position and the 'ATG' translation initiation site of the gpd gene (wherein the 'A' nucleotide of the 'ATG' translation initiation codon was designated as +1) was determined to contain the putative promoter region ("GPDPro", provided as SEQ ID NO:66). A second promoter region comprising the gpd intron was identified as the nucleotide region between position −973 and +201 (wherein the gpd intron was located at position +49 to +194) and was designated as the GPDIN promoter ("GPDIN", provided as SEQ ID NO:70). In like manner, the nucleotide region between the −875 position and the 'ATG' translation initiation site of the gpm gene was determined to contain the putative promoter region ("GPMLPro", provided as SEQ ID NO:67).

The putative promoter regions identified above were amplified by PCR. Specifically, GPDPro was amplified with oligonucleotides YL211 (SEQ ID NO:68) and YL212 (SEQ ID NO:69) as primers and pT-GPDP (Example 3) as template. The GPDIN promoter was amplified with oligonucleotides YL211 (SEQ ID NO:68) and YL377 (SEQ ID NO:71) as primers and genomic DNA of Yarrowia lipolytica as template. And, GPMLPro was amplified with oligonucleotides YL203 (SEQ ID NO:72) and YL204 (SEQ ID NO:73) as primers and pT-GPML (Example 3) as template. The PCR amplifications were carried out in a 50 μl total volume, comprising: PCR buffer (containing 10 mM KCl, 10 mM (NH$_4$)$_2$SO$_4$, 20 mM Tris-HCl (pH 8.75), 2 mM MgSO$_4$, 0.1% Triton X-100), 100 μg/mL BSA (final concentration), 200 μM each deoxyribonucleotide triphosphate, 10 pmole of each primer and 1 μl of Pfu DNA polymerase (Stratagene, San Diego, Calif.). The thermocycler conditions were set for 35 cycles at 95° C. for 1 min, 56° C. for 30 sec, 72° C. for 1 min, followed by a final extension at 72° C. for 10 min.

The PCR products were then purified using a Qiagen PCR purification kit and subjected to the following restriction digestions and ligation reactions:

The GPDPro PCR product was completely digested with SalI and then partially digested with NcoI. The SalI/NcoI fragment was purified following gel electrophoresis in 1% (w/v) agarose and ligated to NcoI/SalI digested pY5-30 vector (Example 5) (wherein the NcoI/SalI digestion had excised the TEF promoter from the pY5-30 vector backbone).

A portion of the GPDIN PCR product was completely digested with SalI/PstI. The 652 bp SalI/PstI fragment was purified following gel electrophoresis in 1% (w/v) agarose. The remaining portion of the GPDIN PCR product was completely digested with PstI/NcoI, and the 521 bp PstI/NcoI fragment was purified following gel electrophoresis in 1% (w/v) agarose. The 652 bp SalI/PstI fragment and the 521 bp PstI/NcoI fragment were directionally ligated to SalI/NcoI digested pY5-30 vector (wherein the SalI/NcoI digestion had excised the TEF promoter from the pY5-30 vector backbone).

The GPMLPro PCR product was digested with NcoI and SalI for 1 hr at 37° C. and then purified following gel electrophoresis in 1% (w/v) agarose. The NcoI/SalII-digested PCR product was ligated to NcoI/SalI digested pY5-30 vector.

Ligated DNA from each reaction was then used to individually transform E. coli DH5α. Transformants were selected on LB agar containing ampicillin (100 μg/mL).

Figure 8A:
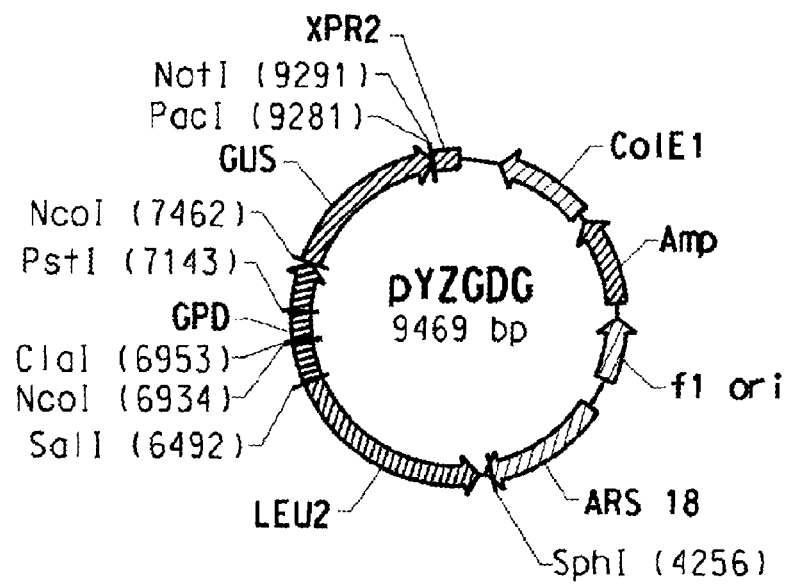

Analysis of the plasmid DNA from one transformant containing GPDPro confirmed the presence of the expected plasmid, designated "pYZGDG" (FIG. 8A). Thus, this plasmid contained a chimeric gene comprising a GPD promoter, GUS reporter gene and XPR terminator.

Figure 8B:
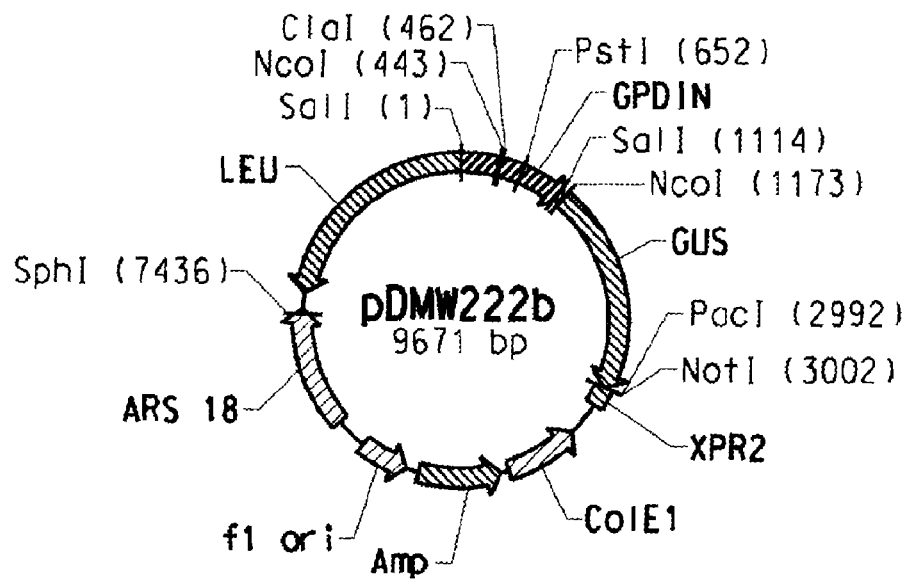

Analysis of the plasmid DNA from one transformant containing GPDIN confirmed the presence of the expected plasmid, designated pDMW222 (FIG. 8B). Thus, this plasmid contained a chimeric gene comprising a GPDIN promoter, GUS reporter gene and XPR terminator.

Figure 8C:
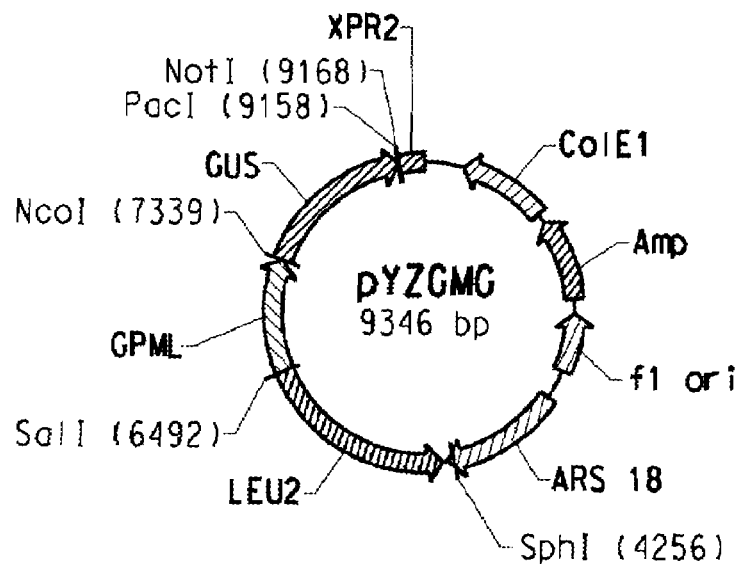

Analysis of the plasmid DNA from one transformant containing GPMLPro confirmed the presence of the expected plasmid, designated "pYZGMG", and comprising a GPM::GUS::XPR chimeric gene (FIG. 8C).

Example 7

Synthesis of pDMW212 and pDMW214 Comprising the FBA and FBAIN Promoters

The present Example describes the synthesis of pDMW212 (comprising a FBA promoter::GUS::XPR terminator chimeric gene) and pDMW214 (comprising a FBAIN promoter::GUS::XPR terminator chimeric gene, wherein FBAIN is the FBA promoter region along with a portion of the 5' coding region comprising the fba1 intron). Synthesis of these plasmids was conducted in a manner similar to that described in Example 6, wherein the promoter regions were identified, amplified and then cloned into a derivative of pY5-30 (Example 5).

The FBA promoter region (corresponding to the nucleotide region between position −832 to −1 bp of SEQ ID NO:74) was amplified with oligonucleotides ODMW314 (SEQ ID NO:75) and YL341 (SEQ ID NO:76) as primers and genomic DNA of Y. lipolytica as template. The FBAIN promoter region (exemplified by SEQ ID NO:77, and corresponding to the nucleotide region between position −826 bp to +169 bp around the putative translation initiation site) was amplified with oligonucleotides ODMW320 (SEQ ID NO:78) and ODMW341 (SEQ ID NO:79) as primers and genomic DNA of Y. lipolytica as template.

The individual PCR amplification reactions were carried out in a 50 μl total volume, comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer and 1 μl of Pfu DNA polymerase (Stratagene). The thermocycler conditions were set for 35 cycles at 95° C. for 1 min, 56° C. for 30 sec, 72° C. for 1 min, followed by a final extension at 72° C. for 10 min.

The individual PCR products were purified using a Qiagen PCR purification kit. The FBA promoter region and the FBAIN promoter region were then digested with NcoI and SalI for 1 hr at 37° C. and purified following gel electrophoresis in 1% (w/v) agarose. The NcoI/SalII-digested PCR products were ligated to NcoI/SalI digested pY5-30 vector. Ligated DNA from each reaction was then used to individually transform E. coli DH10B. Transformants were selected on LB agar containing ampicillin (100 μg/mL).

Figure 8D:
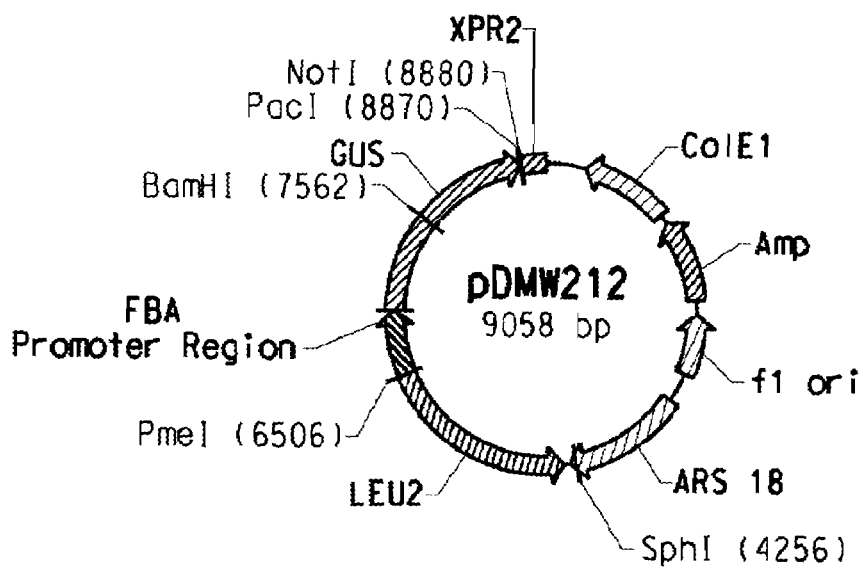

Analysis of the plasmid DNA from one transformant containing the FBA promoter region confirmed the presence of the expected plasmid, designated "pDMW212" (FIG. 8D). Thus, this plasmid contained a chimeric gene comprising a FBA promoter, GUS reporter gene and XPR terminator.

Figure 8E:
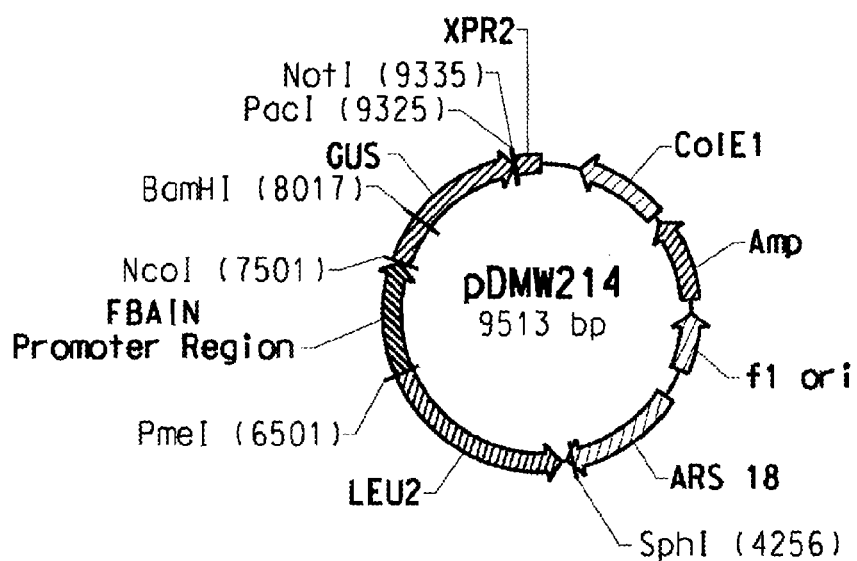

Analysis of the plasmid DNA from one transformant containing the FBAIN promoter confirmed the presence of the expected plasmid, designated "pDMW214", and comprising a FBA promoter region along with a portion of the 5' coding region that has an intron ("FBAIN"), a GUS reporter gene and XPR terminator (i.e., a FBAIN::GUS::XPR chimeric gene) (FIG. 8E).

Example 8

Transformation of Y. lipolytica with pY5-30, pYZGDG, pDMW222, pYZGMG, pDMW212 and pDMW214

The plasmids pY5-30 (Example 5; comprising a TEF::GUS::XPR chimeric gene), pYZGDG (Example 6; comprising a GPD::GUS::XPR chimeric gene), pDMW222 (Example 6; comprising a GPDIN::GUS::XPR chimeric gene), pYZGMG (Example 6; comprising a GPM::GUS::XPR chimeric gene), pDMW212 (Example 7; comprising a FBA::GUS::XPR chimeric gene) and pDMW214 (Example 7; comprising a FBAIN::GUS::XPR chimeric gene) were transformed separately into Y. lipolytica ATCC #76982 according to the method of Chen, D. C. et al. (Appl. Microbiol Biotechnol. 48(2):232-235 (1997)).

Briefly, a leucine auxotroph of Yarrowia was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. About 500 ng of plasmid DNA was incubated in 100 μl of resuspended cells, and maintained at 39° C. for 1 hr with vortex mixing at 15 min intervals. The cells were plated onto minimal media plates lacking leucine and maintained at 30° C. for 2 to 3 days.

Using this technique, transformants were obtained that contained pY5-30, pYZGDG, pDMW222, pYZGMG, pDMW212 and pDMW214, respectively.

Example 9

Comparative Analysis of the TEF, GPD and GPM Promoter Activities in Yarrowia lipolytica The activity of the TEF, GPD and GPM promoters was determined in Yarrowia lipolytica containing the pY5-30, pYZGDG and pYZGMG constructs, each of which possessed a GUS reporter gene and an XPR terminator. GUS activity in each expressed construct was measured by histochemical and fluorometric assays (Jefferson, R. A. Plant Mol. Biol. Reporter 5:387405 (1987)).

GUS Activities, Determined by Histochemical Assay

Specifically, two Y. lipolytica strains containing plasmid pY5-30, two Y. lipolytica strains containing plasmid pYZGDG and two Y. lipolytica strains containing plasmid pYZGMG were each grown from single colonies in 3 mL minimal media (20 g/L glucose, 1.7 g/L yeast nitrogen base without amino acids, 1 g/L L-proline, 0.1 g/L L-adenine, 0.1 g/L L-lysine, pH 6.1) at 30° C. to an $OD_{600}$ ~1.0. Then, 100 μl of cells were collected by centrifugation, resuspended in 100 μl of histochemical staining buffer and incubated at 30° C. [Staining buffer prepared by dissolving 5 mg of 5-bromo-4-chloro-3-indolyl glucuronide (X-Gluc) in 50 μl dimethyl formamide, followed by addition of 5 mL 50 mM $NaPO_4$, pH 7.0.]

The results of histochemical staining showed that the TEF promoter in construct pY5-30, the GPD promoter in construct pYZGDG and the GPM promoter in construct pYZGMG were all active. The GPD promoter appeared to be much stronger than the TEF promoter (FIG. 9A), while the GPM promoter was at least as strong as the TEF promoter (FIG. 9B).

GUS Activities, Determined by Fluorometric Assay

GUS activity was also assayed by fluorometric determination of the production of 4-methylumbelliferone from the corresponding substrate β-glucuronide (Jefferson, R. A., supra).

*Y. lipolytica* strains containing plasmids pY5-30, pYZGDG and pYZGMG, respectively, were grown from single colonies in 3 mL minimal media (as described above) at 30° C. to an $OD_{600}$~1.0. Then, the 3 mL cultures were each added to a 500 mL flask containing 50 mL minimal media and grown in a shaking incubator at 30° C. for about 24 hrs. The cells were collected by centrifugation, resuspended in Promega Cell Lysis Buffer and lysed using the BIO 101 Biopulverizer system (Vista, Calif.). After centrifugation, the supernatants were removed and kept on ice.

For each fluorometric assay, 100 μl of extract was added to 700 μl of GUS assay buffer (2 mM 4-methylumbelliferyl-β-D-glucuronide ("MUG") in extraction buffer) and placed at 37° C. Aliquots of 100 μl were taken at 0, 30 and 60 min time points and added to 900 μl of stop buffer (1 M $Na_2CO_3$). Each time point was read using a Fluorimeter (CytoFluor R Series 4000, Framingham, Mass.) set to an excitation wavelength of 360 nm and an emission wavelength of 455 nm. Total protein concentration of each sample was determined using 10 μl of extract and 200 μl of BioRad Bradford reagent (Bradford, M. M. *Anal. Biochem.* 72:248-254 (1976)). GUS activity was expressed as nmoles of 4-MU per minute per mg of protein.

Results of these fluorometric assays are shown in FIG. 9. Specifically, FIG. 9C showed that the GPD promoter was 3 times stronger than the TEF promoter in *Y. lipolytica*; in contrast, FIG. 9D showed that the GUS activity of the GPM promoter was about 110% as active as the TEF promoter.

Example 10

Quantitative Comparison of the Transcriptional Activities of the TEF, GPD, GPDIN, FBA and FBAIN Promoters in *Yarrowia lipolytica*

The transcriptional activities of the TEF, GPD, GPDIN, FBA and FBAIN promoters were determined in *Y. lipolytica* containing the pY5-30, pYZGDG, pDMW222, pDMW212 and pDMW214 constructs by quantitative PCR analyses. This required isolation of RNA and real time RT-PCR.

More specifically, *Y. lipolytica* strains containing each plasmid above were grown from single colonies in 6 mL of minimal media (supra, Example 9) in 25 mL Erlenmeyer flasks for 16 hrs at 30° C. Each of the 6 mL starter cultures was then added to individual 500 mL flasks containing 140 mL high glucose media (14 g/L $KH_2PO_4$, 4 g/L $K_2HPO_4$, 2 g/L $MgSO_4.7H_2O$, 80 g/L glucose, pH 6.5) and incubated at 30° C. for 4 days. In each interval of 24 hrs, 1 mL of each culture was removed from each flask to measure the optical density, 27 mL was removed and used for a fluorometric GUS assay (as described in Example 9), and two aliquots of 1.5 mL were removed for RNA isolation. The culture for RNA isolation was centrifuged to produce a cell pellet.

RNA Isolation

The RNA was isolated from *Yarrowia* strains according to the modified Qiagen RNeasy mini protocol (Qiagen, San Diego, Calif.). Briefly, at each time point for each sample, 340 μL of Qiagen's buffer RLT was used to resuspend each of the two cell pellets. The buffer RLT/cell suspension mixture from each of the two tubes was combined in a bead beating tube (Bio101, San Diego, Calif.). About 500 μL of 0.5 mL glass beads was added to the tube and the cells were disrupted with a BeadBeater (Biospec Products, Inc.). The disrupted cells were then pelleted by centrifugation at 14,000 rpm for 1 min and 350 μl of the supernatent was transferred to a new microcentrifuge tube. Ethanol (350 μL of 70%) was added to each homogenized lysate. After gentle mixing, the entire sample was added to a RNeasy mini column in a 2 mL collection tube. The sample was centrifuged for 15 sec at 10,000 rpm. Buffer RW1 (350 μL) was added to the RNeasy mini column and the column was centrifuged for 15 sec at 10,000 rpm to wash the cells. The eluate was discarded. Qiagen's DNase1 stock solution (10 μL) was added to 70 μl of Buffer RDD and gently mixed. This entire DNase solution was added to the RNeasy mini column and incubated at room temperature for 15 min. After the incubation step, 350 μL of Buffer RW1 was added to the mini column and the column was centrifuged for 15 sec at 10,000 rpm. The column was washed twice with 700 μL Buffer RW1. RNase-free water (50 μL) was added to the column. The column was centrifuged for 1 min at 10,000 rpm to elute the RNA.

Real Time RT-PCR Analysis

A two-step RT-PCR protocol was used, wherein total *Yarrowia* RNA was first converted to cDNA and then the cDNA was analyzed using Real Time PCR. The conversion to cDNA was performed using Applied Biosystems' High Capacity cDNA Archive Kit (PN #4322171; Foster City, Calif.) and Molecular Biology Grade water from MediaTech, Inc. (PN #46-000-Con; Holly Hill, Fla.). Total RNA from *Yarrowia* (100 ng) was converted to cDNA by combining it with 10 μl of RT buffer, 4 μl of 25×dNTPs, 10 μl 10× Random Hexamer primers, 5 μl Multiscribe Reverse Transcriptase and 0.005 μl RNase Inhibitor, and brought to a total reaction volume of 100 μl with water. The reactions were incubated in a thermocycler for 10 min at 25° C. followed by 2 hrs at 37° C. The cDNA was stored at −20° C. prior to Real Time analysis.

Real Time analysis was performed using the SYBR Green PCR Master Mix from Applied Biosystems (PN #4309155). The Reverse Transcription reaction (2 μl) was added to 10 μl of 2×SYBR PCR Mix, 0.2 μl of 100 μM Forward and Reverse primers for either URA (i.e., primers YL-URA-16F [SEQ ID NO:80] and YL-URA-78R [SEQ ID NO:81]) or GUS (i.e., primers GUS-767F [SEQ ID NO:82] and GUS-891R [SEQ ID NO:83]) and 7.2 μl water. The reactions were thermocycled for 10 min at 95° C. followed by 40 cycles of 95° C. for 5 sec and 60° C. for 1 min in an ABI 7900 Sequence Detection System instrument. Real time fluorescence data was collected during the 60° C. extension during each cycle.

Relative quantitation was performed using the ΔΔCT method as per User Bulletin #2: "Relative Quantitation of Gene Expression", Applied Biosystems, Updated 10/2001. The URA gene was used for normalization of GUS expression. In order to validate the use of URA as a normalizer gene, the PCR efficiency of GUS and URA were compared and they were found to be 1.04 and 0.99, respectively (where 1.00 equals 100% efficiency). Since the PCR efficiencies were both near 100%, the use of URA as a normalizer for GUS expression was validated, as was the use of the ΔΔCT method for expression quantitation. The normalized quantity is referred to as the ΔCT.

The GUS mRNA in each different strain (i.e., *Y. lipolytica* containing the pYZGDG, pDMW222, pDMW212 and pDMW214 constructs) was quantified to the mRNA level of the *Y. lipolytica* strain with pY5-30 (i.e., TEF::GUS). Thus, relative quantitation of expression was calculated using the mRNA level of the strain with TEF::GUS as the reference sample. The normalized value for GPD::GUS, GPDIN::GUS, FBA::GUS and FBAIN::GUS was compared to the normalized value of the TEF::GUS reference. This quantity is referred to as the ΔΔCT. The ΔΔCT values were then converted to absolute values by utilizing the formula $2^{-\Delta\Delta CT}$. These values refer to the fold increase in the mRNA level of GUS in the strains comprising the chimeric GPD::GUS, GPDIN::GUS, FBA::GUS and FBAIN::GUS genes, as compared to the chimeric TEF::GUS gene. Using this methodology, it was possible to compare the activity of the TEF promoter to the GPD, GPDIN, FBA and FBAIN promoters.

The results of the relative quantitation of mRNA for each GUS chimeric gene are shown in FIG. 10A. More specifically, the assay showed that after 24 hrs in high glucose media, the transcription activity of the FBA and FBAIN promoters was about 3.3 and 6 times stronger than the TEF promoter, respectively. Similarly, the transcription activity of the GPD and GPDIN promoters was about 2 and 4.4 times stronger than the TEF promoter, respectively. While the transcription activities of the chimeric FBA::GUS, FBAIN::GUS, GPD::GUS and GPDIN::GUS gene fusions decreased over the 4 day period of the experiment, the transcriptional activity of the FBAIN and GPDIN promoters was still about 3 and 2.6 times stronger than the TEF promoter in the final day of the experiment, respectively.

Example 11

Confirmation of the Presence of an Enhancer within the gpd Intron

The present Example describes construction of a chimeric promoter that was generated to drive expression of the GUS reporter gene, in order to confirm the presence of an enhancer located within the intron of the gpd gene (SEQ ID NO:97). This chimeric promoter thus consisted of a GPM::GPDIN promoter fusion.

The chimeric promoter is described below in Table 3 and is designated herein as "GPM::GPDIN". The chimeric promoter provided as SEQ ID NO:84 consisted of the complete GPM promoter, plus an additional component comprising the intron of the gpd gene.

TABLE 3

| Construction of A Chimeric Promoter | | | |
|---|---|---|---|
| Chimeric Promoter | Component 1 | Component 2 | SEQ ID NO |
| GPM::GPDIN | −1 to −843 region of GPM | +1 to +198 region of GPDIN, wherein the 146 bp intron is located from +49 to +194 | 84 |

The chimeric promoter was then positioned such that it drove expression of the GUS reporter gene in the pY5-30 vector backbone (wherein the TEF promoter had been removed). Specifically, pDMW225 (FIG. 10B) contained a chimeric gene comprising the chimeric GPM::GPDIN promoter, GUS and the XPR terminator.

The activity of the GPM::GPDIN promoter was compared with the TEF, FBAIN, GPDIN and GPM promoters by comparing the GUS activity in the *Y. lipolytica* strain comprising pDMW225 relative to the GUS activity in *Y. lipolytica* strains comprising pY5-30, pDMW214, pDMW222 and pYZGMG constructs, respectively. As in previous Examples, this direct comparison was possible, since each strain possessed a different promoter but the same GUS reporter gene and XPR terminator. GUS activity in each expressed construct was measured by histochemical assays (supra, Example 9).

Results of these histochemical assays are shown in FIG. 10C. As previously determined, the FBAIN promoter was the strongest promoter. However, the chimeric GPM::GPDIN promoter was much stronger than the GPM promoter and was equivalent to the GPDIN promoter. Thus, this confirmed the existence of an enhancer in the gpd intron (SEQ ID NO:97).

Example 12

Use of the GPD Promoter for Δ15 Desaturase Expression In *Yarrowia lipolytica*

The present Example describes the construction of a chimeric gene comprising a GPD promoter, fungal Δ15 desaturase and XPR terminator, and the expression of this gene in *Y. lipolytica*. Since transformed host cells were able to produce ALA (while wildtype *Y. lipolytica* do not possess any Δ15 desaturase activity), this confirmed the ability of the GPD promoter to drive expression of heterologous PUFA biosynthetic pathway enzymes in oleaginous yeast cells such as *Y. lipolytica*.

Construction of Plasmid DY34, Comprising a GPD::Fm1::XPR Chimeric Gene

First, plasmid pY5-13 was constructed as a derivative of pY5 (from Example 5). Specifically, pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:85 and 86) to generate pY5-5. A SalI site was introduced into pY5-5 between the LEU2 gene and the TEF promoter by site-directed mutagenesis using oligonucleotides YL9 and YL10 (SEQ ID NOs:62 and 63) to generate pY5-6. A PacI site was introduced into pY5-6 between the LEU2 gene and ARS18 using oligonucleotides YL7 and YL8 (SEQ ID NOs:87 and 88) to generate pY5-8. A NcoI site was introduced into pY5-8 around the translation start codon of the TEF promoter using oligonucleotides YL3 and YL4 (SEQ ID NOs:58 and 59) to generate pY5-9. The NcoI site inside the LEU2 gene of pY5-9 was eliminated using YL1 and YL2 oligonucleotides (SEQ ID NOs:56 and 57) to generate pY5-12. Finally, a BsiWI site was introduced into pY5-12 between the ColEI and XPR region using oligonucleotides YL61 and YL62 (SEQ ID NOs:89 and 90) to generate pY5-13.

A purified SalI/NcoI fragment comprising GPDPro (from Example 6) was ligated to NcoI/SalI digested pY5-13 vector (wherein the NcoI/SalI digestion had excised the TEF promoter from the pY5-13 vector backbone) to yield "pY5-13GPD". Thus, pY5-13GPD comprised a GPD promoter::XPR terminator expression cassette.

The Nco I site at the 3' end of the promoter fragment in pY5-13GPD was converted to a Not I site to yield "pY5-13GPDN". For this, the GPD promoter was re-amplified by PCR using GPDsense (SEQ ID NO:91) and GPDantisense (SEQ ID NO:92) primers with a Not I site. The resultant promoter fragment was digested with Sal I and Not I and cloned into the Sal/NotI site of pY5-13 (thus removing the TEF promoter) to produce pY5-13GPDN.

The ORF encoding the *Fusarium moniliforme* strain M-8114 Δ15 desaturase (SEQ ID NO:93; see co-pending U.S. patent application Ser. No. 10/985,254) was PCR amplified using the cDNA clone ffm1c.pK001.g23 (E.I. du Pont de Nemours and Co., Inc., Wilmington, Del.) containing the full-length cDNA as the template and using upper and lower primers P192 and P193 (SEQ ID NOs:95 and 96). The PCR was carried out in an Eppendorf Mastercycler Gradient Cycler using Pfu polymerase, per the manufacturer's recommendation. Amplification was carried out as follows: initial denaturation at 95° C. for 1 min, followed by 30 cycles of denaturation at 95° C. for 30 sec, annealing at 58° C. for 1 min, and elongation at 72° C. for 1 min. A final elongation cycle at 72° C. for 10 min was carried out, followed by reaction termination at 4° C.

The correct-sized (ca. 1240 bp) fragment was obtained, purified from an agarose gel using a Qiagen DNA purification kit, digested with Not I and cloned into the Not I site between the GPD promoter and XPR terminator of plasmid pY5-13GPDN. This resulted in creation of plasmid "pY34", which contained a GPD::Fm1::XPR chimeric gene.

Expression of Plasmid pY34 (GPD::Fm1::XPR) in *Yarrowia lipolytica* pY5 (vector alone control, from Example 5) and pY34 (GPDP::Fm1::XPR) were each individually transformed into wild type (WT) *Yarrowia lipolytica* ATCC #76892, using the transformation procedure described in Example 8, and selected on Bio101 DOB/CSM-Leu plates.

Single colonies of wild type and transformant cells were each grown in 3 mL minimal media (supra) at 30° C. to an $OD_{600}$~1.0. The cells were harvested, washed in distilled water, speed vacuum dried and subjected to direct transesterification and GC analysis. Specifically, for fatty acid analysis cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

The fatty acid profile of wildtype *Yarrowia* and the transformant are shown below in Table 4. Fatty acids are identified as 16:0 (palmitate), 16:1 (palmitoleic acid), 18:0, 18:1 (oleic acid), 18:2 (LA) and 18:3 (ALA) and the composition of each is presented as a % of the total fatty acids.

TABLE 4

| Expression of *Fusarium* Δ15 Desaturase In *Yarrowia lipolytica* | | | | | | |
|---|---|---|---|---|---|---|
| *Y. lipolytica* strain | % 16:0 | % 16:1 | % 18:0 | % 18:1 | % 18:2 | % ALA |
| WT | 12.1 | 9.1 | 0.8 | 33.8 | 44.2 | 0.0 |
| WT + GPD:Fm1:XPR | 10.0 | 10.5 | 1.3 | 37.0 | 7.2 | 31.0 |

The results above demonstrated that the GPD promoter is suitable to drive expression of the Δ15 desaturase, leading to production of ALA in *Yarrowia*.

What is claimed is:

1. An isolated nucleic acid molecule comprising the intron of the *Yarrowia* gpd gene as set forth in SEQ ID NO:97.

2. A plasmid comprising the gpd intron of claim 1.

* * * * *